(12) United States Patent
van den Oudenrijn et al.

(10) Patent No.: US 8,268,966 B2
(45) Date of Patent: Sep. 18, 2012

(54) BINDING MOLECULES FOR THE TREATMENT OF MYELOID CELL MALIGNANCIES

(75) Inventors: Sonja van den Oudenrijn, Uithoorn (NL); Marja van Meijer, Amsterdam (NL); Adrianus Q. Bakker, Abbekerk (NL); Alexander Berthold Hendrik Bakker, Hillegom (NL)

(73) Assignee: Crucell Holland B.V., Leiden (NL)

( * ) Notice: Subject to any disclaimer, the term of this patent is extended or adjusted under 35 U.S.C. 154(b) by 251 days.

(21) Appl. No.: 12/653,779

(22) Filed: Dec. 18, 2009

(65) Prior Publication Data

US 2010/0184671 A1 Jul. 22, 2010

Related U.S. Application Data

(60) Division of application No. 11/317,786, filed on Dec. 22, 2005, now Pat. No. 7,741,443, which is a continuation of application No. PCT/EP2004/051243, filed on Jun. 25, 2004.

(30) Foreign Application Priority Data

| Jun. 25, 2003 | (WO) | PCT/EP2003/050264 |
| Feb. 9, 2004 | (WO) | PCT/EP2004/050100 |
| Jun. 25, 2004 | (WO) | PCT/EP2004/051243 |

(51) Int. Cl.
*C07K 14/00* (2006.01)
*C12N 15/00* (2006.01)

(52) U.S. Cl. ...................... 530/350; 435/69.3

(58) Field of Classification Search .................. None
See application file for complete search history.

(56) References Cited

U.S. PATENT DOCUMENTS

| 4,885,172 | A | 12/1989 | Bally et al. |
| 5,059,421 | A | 10/1991 | Loughrey et al. |
| 5,171,578 | A | 12/1992 | Bally et al. |
| 5,316,771 | A | 5/1994 | Barenholz et al. |
| 5,380,531 | A | 1/1995 | Chakrabarti et al. |
| 5,945,589 | A | 8/1999 | Rao et al. |
| 6,265,150 | B1 | 7/2001 | Terstappen et al. |
| 6,416,973 | B1 * | 7/2002 | Bakker et al. .............. 435/69.1 |
| 6,534,631 | B1 | 3/2003 | Ruben et al. |
| 6,627,195 | B1 | 9/2003 | Paul |
| 6,953,843 | B2 | 10/2005 | Bakker et al. |
| 7,319,140 | B2 | 1/2008 | Bakker et al. |
| 2002/0022031 | A1 | 2/2002 | Goldenberg et al. |
| 2004/0053245 | A1 * | 3/2004 | Tang et al. ................ 435/6 |
| 2006/0247420 | A1 | 11/2006 | Coukos et al. |

FOREIGN PATENT DOCUMENTS

| WO | WO 98/15833 | 4/1998 |
| WO | WO 00/63403 | 10/2000 |
| WO | WO0157188 | * 8/2001 |
| WO | WO 0157188 | 9/2001 |
| WO | WO 01/73133 | 10/2001 |
| WO | WO 02/103012 A1 | 12/2002 |
| WO | WO 03/042367 | 5/2003 |
| WO | 2004022706 | * 3/2004 |
| WO | WO 2004067569 | 8/2004 |
| WO | WO 2005/000894 A1 | 1/2005 |

OTHER PUBLICATIONS

Suzuki et al, J Immun 156:128-135, 1996.*
Marshall et al, J. Biol. Chem. 279:14792-14802, Apr. 2004.*
Barten et al., The human Ly-49L gene, Immunogenetics, 1999, pp. 731-734, vol. 49 and database EMBL XP002305617.
Casset et al., BBRC 307, 2003, pp. 198-205.
Database EMBL Mar. 26, 2002, WP002305618 retrieved from EBI, Database accession No. AF247788, abstract.
Database WPI Week 200229, Derwent Publications Ltd., London, GB; XP-002305620, Dec. 12, 2001, abstract.
Han et al., KLRL1, a novel killer cell lectinlike receptor, inhibits natural killer cell cytotoxicity, Blood. Nov. 1, 2004, pp. 2858-2866, vol. 104, No. 9.
Hofer et al., The centromeric part of the human natural killer (NK) receptor complex: lectin-like receptor genes expressed in NK, dendritic and endothelial cells, Immunological reviews, Jun. 2001, pp. 5-19, vol. 181.
Marshall et al., Identification and characterization of a novel human myeloid inhibitory C-type lectin-like receptor (MICL) that is predominantly expressed on granulocytes and monocytes. The Journal of Biological Chemistry, Apr. 9, 2004, pp. 14792-14802, vol. 279, No. 15 and database EMBL Feb. 2, 2004, XP002305619.
Moretta et al., Human NK-cell receptors, Immunology Today, Sep. 1, 2000, pp. 420-422, vol. 21, No. 9, Elsevier Publications, Cambridge, GB.
Pascalis et al., The Journal of Immunology, 2002, pp. 3076-3084, vol. 169.
Paul, Fundamental Immunology, 3rd Edition, 1993, pp. 292-295.
PCT International Preliminary Examination Report, PCT/EP2004/051243, dated Sep. 29, 2005.
PCT International Search Report, PCT/EP2004/051243, dated May 2, 2005.

(Continued)

Primary Examiner — Lei Yao
(74) Attorney, Agent, or Firm — TraskBritt

(57) ABSTRACT

Provided is a human C-type lectin, binding molecules that specifically bind to the human C-type lectin, nucleic acid molecules encoding the binding molecules or the human C-type lectin, compositions comprising the binding molecules or the human C-type lectin and methods of identifying or producing the binding molecules. The human C-type lectin is specifically expressed on myeloid cells and binding molecules capable of specifically binding to the human C-type lectin can be used in the diagnosis, prevention and/or treatment of neoplastic disorders and diseases.

3 Claims, 21 Drawing Sheets

OTHER PUBLICATIONS

Rudikoff et al., Proc. Natl. Acad. Sci., USA, 1982, p. 1979, vol. 79.
Sequence search result for SEQ ID No. 13 (2009).
Office Action for U.S. Appl. No. 11/317,786 dated Jul. 23, 2009.
Office Action for U.S. Appl. No. 11/317,786 dated Aug. 12, 2008.
U.S. Appl. No. 61/278,358, filed Oct. 6, 2009, Beaumont et al, RSV-Specific Binding Molecule.
U.S. Appl. No. 12/383,330, filed Mar. 23, 2009, Bakker et al., Agonistic Binding Molecules to the Human OX40 Receptor.
U.S. Appl. No. 11/990,974, filed Feb. 21, 2008, Throsby et al., Method for Preparing Immunoglobulin Libraries.
U.S. Appl. No. 11/317,786, filed Dec. 22, 2005, van den Oudenrijn et al., Binding Molecules for the Treatment of Myeloid Cell Malignancies.
U.S. Appl. No. 11/387,997, filed Mar. 23, 2006, Throsby et al., Human Binding Molecule Against CDIA.
U.S. Appl. No. 11/978,742, filed Oct. 29, 2007, Bakker et al., Binding Molecules capable of Neutralizing Rabies Virus and Uses Thereof.
U.S. Appl. No. 11/980,237, filed Oct. 29, 2007, Bakker et al., Binding Molecules capable of Neutralizing Rabies Virus and Uses Thereof.
U.S. Appl. No. 12/459,661, filed Jul. 6, 2009, Bakker et al., Binding Molecules Capable of Neutralizing Rabies Virus and Uses Thereof.
U.S. Appl. No. 12/312,967, filed Jun. 2, 2009, Bakker et al., Liquid Anti-Rabies Antibody Formulations.

* cited by examiner

5' Cloning site of pPicZαB

```
                    KEK2
                  Cleavage
         XhoI      site              EcoRI         SfiI
         ~~~~~~     ↓              ~~~~~~      ~~~~~~~~~~~~~~~~~
         S   L   E   K   R   E   A   E   A   A   G   I   H   V   A   Q   P   A   (SEQ ID NO:42)
1181  TCTCTCGAGA AAAGAGAGGC TGAAGCTGCA GGAATTCACG TGGCCCAGCC GGCCG  (SEQ ID NO:36)
      AGAGAGCTCT TTTCTCTCCG ACTTCGACGT CCTTAAGTGC ACCGGGTCGG CCGGC  (SEQ ID NO:37)
```

5' Cloning site of pPicZFVH

```
                    KEK2
                  Cleavage
         XhoI      site    NcoI         EcoRI         SfiI
         ~~~~~~     ↓    ~~~~~~        ~~~~~~      ~~~~~~~~~~~~~~~~~
         S   L   E   K   R   A   M   E   A   A   G   I   H   V   A   Q   P   A   (SEQ ID NO:43)
      TCTCTCGAGA AAAGAGCCATGGAAGCTGCA GGAATTCACG TGGCCCAGCC GGCCG  (SEQ ID NO:38)
      AGAGAGCTCT TTTCTCGGTACCTTCGACGT CCTTAAGTGC ACCGGGTCGG CCGGC  (SEQ ID NO:39)
```

synthetic hinge fragment

```
                              Flexible upper              Cysteine residues
                              hinge region                available for
            NotI                                          disulphide bonding
            ~~~~~~~~                                      ↙       ↘
         A   A   A   P   K   P   S   T   P   P   G   S   S   C   P   P   C  .
1     GCGGCCGCGC CAAAGCCAAG TACCCCACCA GGTTCTTCAT GTCCACCATG
      CGCCGGCGCG GTTTCGGTTC ATGGGGTGGT CCAAGAAGTA CAGGTGGTAC
         Short linker              ClaI              XbaI
        ~~~~~~~~~~~~~~~~         ~~~~~~           ~~~~~~
       .  P   G   S   G   G   A   P   I   D   S   G   F   L   (SEQ ID NO:44)
51    TCCAGGCTCT GGCGGTGCGC CAATCGATAG CGGCTTTCTA GA         (SEQ ID NO:40)
      AGGTCCGAGA CCGCCACGCG GTTAGCTATC GCCGAAAGAT CT         (SEQ ID NO:41)
```

FIG. 15C

BINDING MOLECULES FOR THE TREATMENT OF MYELOID CELL MALIGNANCIES

CROSS-REFERENCE TO RELATED APPLICATIONS

This application is a divisional of U.S. patent application Ser. No. 11/317,786, filed Dec. 22, 2005, now U.S. Pat. No. 7,741,443 (Jun. 22, 2010), which application is a continuation of PCT International Patent Application No. PCT/EP2004/051243, filed on Jun. 25, 2004, designating the United States of America, and published, in English, as PCT International Publication No. WO 2005/000894 A2 on Jan. 6, 2005, which application claims priority to PCT International Patent Application No. PCT/EP04/050100, filed Feb. 9, 2004 and PCT International Patent Application No. PCT/EP03/50264, filed Jun. 25, 2003, the entire contents of each of the above-referenced applications are hereby incorporated herein by this reference.

STATEMENT ACCORDING TO 37 C.F.R. §1.52(e)(5)-SEQUENCE LISTING SUBMITTED ON COMPACT DISC

Pursuant to 37 C.F.R. §1.52(e)(1)(ii), a compact disc containing an electronic version of the Sequence Listing has been submitted concomitant with this application, the contents of which are hereby incorporated by reference. A second compact disc is submitted and is an identical copy of the first compact disc. The discs are labeled "copy 1" and "copy 2," respectively, and each disc contains one file entitled "sequence listings.txt" which is 73 KB and created on Dec. 9, 2008.

TECHNICAL FIELD

The invention relates generally to biotechnology and the field of medicine. The invention particularly relates to the identification of a new human C-type lectin, to binding molecules capable of specifically binding to the new human C-type lectin, to immunoconjugates comprising these binding molecules and to methods of obtaining the binding molecules. The invention further relates to the use of the binding molecules in medicine, in particular for the diagnosis, prevention and/or treatment of neoplastic diseases such as myeloid cell malignancies.

BACKGROUND

Cancer describes a class of disorders and diseases characterized by the uncontrolled growth of aberrant cells. Currently, cancer is one of the most deadly diseases with about 1.2 million new cases of cancer being diagnosed each year in the United States of America alone.

One form of cancer, accounting for about 3% of all cancers in the United States, is leukemia. This malignant disease is characterized by an abnormal proliferation of white blood cells which can be detected in the peripheral blood and/or bone marrow. Leukemia can be broadly classified into acute and chronic leukemia, which can be subclassified in a variety of ways, including morphology, cytochemistry, cell-surface markers, cytoplasmic markers, cytogenetics and oncogene expression. The most important distinction within acute and chronic leukemia is however between myeloid and lymphoid leukemia.

Acute myeloid leukemia ("AML") is the most common form of leukemia accounting for about 50% of all leukemia cases and even 85% of all acute leukemia cases involving adults. Conventional methods of treatment for patients diagnosed with AML include chemotherapeutic treatment with a combination of an anthracycline and cytarabine. For patients with AML in whom there is failure to achieve initial remission or in whom there is relapse after chemotherapy, a bone marrow transplantation presently offers the best chance for cure. Because complete remission rates, even after bone marrow transplantation, are low, novel therapies for AML have been developed. These include treatment with immunoconjugates comprising humanized antibodies against CD33 or CD45 conjugated to radioisotopes or drugs. As these immunoconjugates can only induce remission rates in a fraction of the patients suffering from AML, a need still exists for new and improved therapeutic compounds for the treatment of AML. A further disadvantage of the present immunoconjugates is that they contain humanized antibodies. A well known disadvantage of humanized antibodies is that such antibodies still retain some murine sequences and therefore still elicit an unwanted immune reaction, especially when administered for prolonged periods.

Chronic myeloid leukemia ("CML") has less of an incidence than AML, but still accounts for about 15% of all leukemia cases. Currently, the only unequivocally curative treatment for CML is allogeneic bone marrow transplantation. Unfortunately, for 60% of the patients this therapy may not be available either due to the lack of a suitable donor due to differences in human leukocyte antigens ("HLA") or the age of the recipient and therefore alternative forms of therapy such as chemotherapy must be employed. Conventional chemotherapy makes use of compounds, such as hydroxyurea, that are cytotoxic for actively dividing cells. Although effective, these agents are not selective for the leukemic clone and this is the cause of undesirable side effects. Moreover, as the disease progresses patients frequently become refractory to chemotherapy. The standard therapy for CML for newly diagnosed patients of CML is considered treatment with interferon such as human leukocyte interferon or recombinant alpha-interferon. A disadvantage of this standard therapy is that patients can become resistant or intolerant to interferon.

Recently, a new compound useful in the treatment of CML has been developed. This compound called imatinib, STI571 or GLEEVEC® is capable of inhibiting Bcr-Abl tyrosine kinase. Disadvantageously, therapy with this compound requires frequent and careful monitoring, particularly for myelosuppression, fluid retention and hepatotoxicity.

A further therapy for CML involves treatment with anti-NCA antibodies (see, US Patent Application No. 2002/0022031). A disadvantage of these antibodies is that the antigen they bind to, i.e., the non-specific cross-reacting antigen (NCA-antigen), is not exclusively expressed on myeloid cells. It can be found on granulocytes as well as on normal colonic mucosa and colonic adenocarcinoma. In view of the drawbacks of the current therapies, there is still a need for new and improved therapeutic compounds for the treatment of CML. In conclusion, there is a need for target molecules and therapeutic compounds specific for myeloid neoplastic diseases such as inter alia AML and CML.

Chinese patent application CN1325874 describes a protein called CLL-1 (C-type lectin like protein) encoded by the mRNA sequence with the Genbank accession number NM_138337. The deduced amino acid sequence of the protein contains 265 amino acids. In CN1325874 is suggested that CLL-1 is a natural killer (NK) cell receptor, i.e., a surface molecule expressed on NK cells, a lymphoid cell type. Furthermore, Northern blot analysis in CN1325874 revealed that CLL-1 is highly expressed in a broad range of tissues and cells, i.e., liver, spleen and peripheral blood cells.

DISCLOSURE OF INVENTION

Described is a human C-type lectin having an amino acid sequence of 275 amino acids. This human C-type lectin differs from the CLL-1 protein described in CN1325874, in that it contains an extra stretch of ten amino acids at its N-terminus, therewith adding a YXXM motif (SEQ ID NO:33), i.e., a motif suggested to be involved in internalization, to the protein (Chuang et al., 1997; Wu et al., 2003). Surprisingly, it was found that the human C-type lectin of the invention is exclusively expressed by myeloid cells and not expressed by lymphoid cells and other cell types. This finding, together with the fact that the human C-type lectin of the invention contains an internalization motif, makes the human C-type lectin a suitable target molecule for binding molecules, particularly immunoconjugates, in the diagnosis, prevention and/or treatment of myeloid neoplastic diseases such as inter alia AML and CML. So, in one aspect, described is a new human C-type lectin. In another aspect, also described are human binding molecules, such as human immunoconjugates, capable of specifically binding to the new human C-type lectin. These human binding molecules are particularly suitable for diagnosis, prevention and/or treatment of humans as they do not have the disadvantages and drawbacks of binding molecules having non-human sequences.

As described herein, a human C-type lectin specifically expressed by myeloid cells has been identified. Furthermore, several binding molecules capable of binding to the human C-type lectin have been identified and obtained by using phage display technology. Furthermore, methods of producing these binding molecules and the use of the binding molecules in diagnosis, prevention and treatment of neoplastic disorders and diseases have been described.

DESCRIPTION OF THE FIGURES

FIG. 15 shows the construction of the bivalent scFv expression vector pPICZbiFVH.

DETAILED DESCRIPTION OF THE INVENTION

Figure 1:
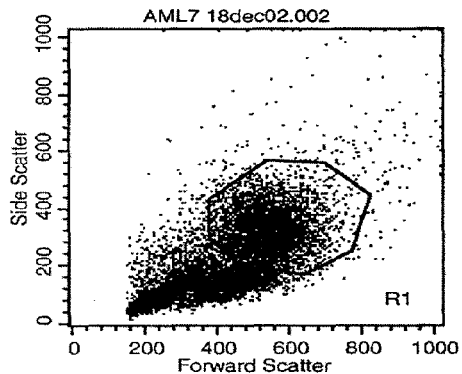
FIG. 1: Binding of the SC02-357 phage antibody and a control phage antibody to a set of four different primary AML blasts (FAB subtypes: AML7, FAB-M4; AML9, FAB-M1; AML10, FAB-M2; AML11, FAB-M0).
Figure 1:
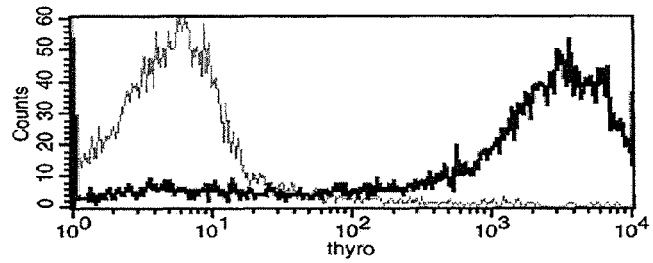
Figure 1:
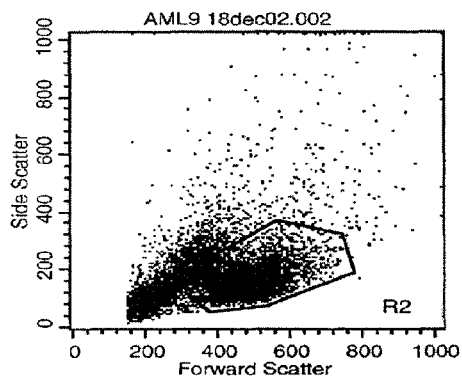
Figure 1:
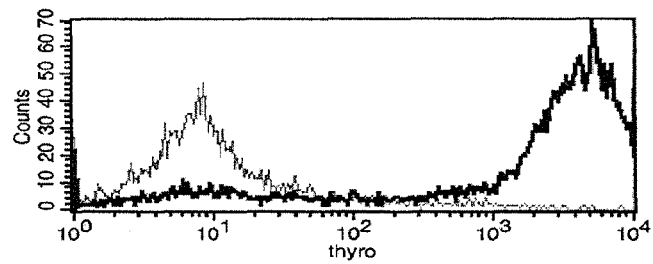
Figure 1:
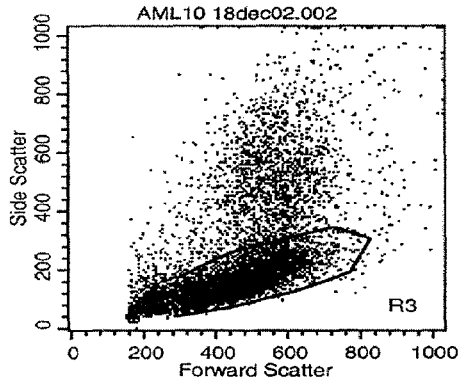
Figure 1:
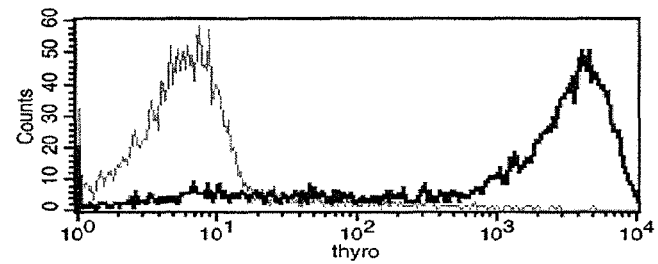
Figure 1:
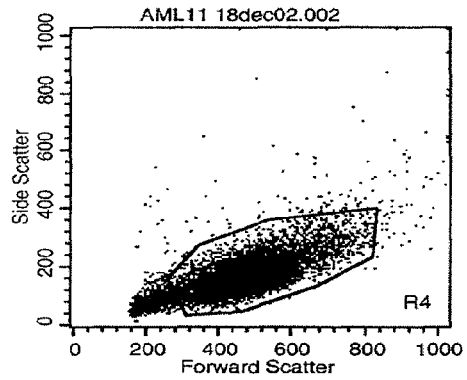
Figure 1:
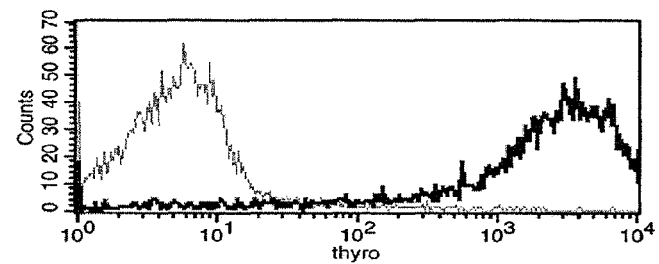

Acute myeloid leukemia. As used herein the term "acute myeloid leukemia" is characterized by an uncontrolled proliferation of—progenitor cells of myeloid origin including, but not limited to, myeloid progenitor cells, myelomonocytic progenitor cells, immature megakaryoblasts.

Amino acid sequence. The term "amino acid sequence" as used herein refers to naturally occurring or synthetic molecules and to a peptide, oligopeptide, polypeptide, or protein sequence.

Apoptosis. As used herein, the term "apoptosis" refers to any cell death, orderly or controlled, that results from the complex cascade of cellular events that occur at specific stages of cellular differentiation and in response to specific stimuli. Apoptosis is characterized and/or accompanied by one or more characteristic cell changes, including, but not limited to, condensation of cytoplasm, loss of plasma membrane microvilli, segmentation of the nucleus, degradation of chromosomal DNA or loss of mitochondrial function. Apoptosis can be determined and measured, for instance, by cell viability assays, FACS analysis or DNA electrophoresis, all of which are known in the art.

Binding molecule. As used herein the term "binding molecule" refers to an intact immunoglobulin including monoclonal antibodies, such as chimeric, humanized or human monoclonal antibodies, or to an antigen-binding and/or variable domain comprising fragment of an immunoglobulin that competes with the intact immunoglobulin for specific binding to the binding partner of the immunoglobulin, e.g., the human C-type lectin. Regardless of structure, the antigen-binding fragment binds with the same antigen that is recognized by the intact immunoglobulin. The term "binding molecule," as used herein also includes the immunoglobulin classes and subclasses known in the art. Depending on the amino acid sequence of the constant domain of their heavy chains, binding molecules can be divided into the five major classes of intact antibodies: IgA, IgD, IgE, IgG, and IgM, and several of these may be further divided into subclasses (isotypes), e.g., IgA1, IgA2, IgG1, IgG2, IgG3 and IgG4.

Antigen-binding fragments include, inter alia, Fab, F(ab'), F(ab')$_2$, Fv, dAb, Fd, complementarity determining region (CDR) fragments, single-chain antibodies (scFv), bivalent single-chain antibodies, diabodies, triabodies, tetrabodies, (poly)peptides that contain at least a fragment of an immunoglobulin that is sufficient to confer specific antigen binding to the (poly)peptide, etc. The above fragments may be produced synthetically or by enzymatic or chemical cleavage of intact immunoglobulins or they may be genetically engineered by recombinant DNA techniques. The methods of production are well known in the art and are described, for example, in *Antibodies: A Laboratory Manual*, edited by E. Harlow and D. Lane (1988), Cold Spring Harbor Laboratory, Cold Spring Harbor, N.Y., which is incorporated herein by reference. A binding molecule or antigen-binding fragment thereof may have one or more binding sites. If there is more than one binding site, the binding sites may be identical to one another or they may be different.

The binding molecule can be a naked or unconjugated binding molecule. A naked or unconjugated binding molecule is intended to refer to a binding molecule that is not conjugated, operatively linked or otherwise physically or functionally associated with an effector moiety or tag, such as inter alia a toxic substance, a radioactive substance, a liposome, an enzyme. It will be understood that naked or unconjugated binding molecules do not exclude binding molecules that have been stabilized, multimerized, humanized or in any other way manipulated, other than by the attachment of an effector moiety or tag. Accordingly, all post-translationally modified naked and unconjugated binding molecules are included herewith, including where the modifications are made in the natural binding molecule-producing cell environment, by a recombinant binding molecule-producing cell, and are introduced by the hand of man after initial binding molecule preparation. Of course, the term naked or unconjugated binding molecule does not exclude the ability of the binding molecule to form functional associations with effector cells and/or molecules after administration to the body, as some such interactions are necessary in order to exert a biological effect.

Biological sample. As used herein, the term "biological sample" encompasses a variety of sample types, including blood and other liquid samples of biological origin, solid tissue samples such as a biopsy specimen or tissue cultures, or cells derived therefrom and the progeny thereof. The term also includes samples that have been manipulated in any way after their procurement, such as by treatment with reagents, solubilization, or enrichment for certain components, such as proteins or polynucleotides. The term encompasses various kinds of clinical samples obtained from any species, and also includes cells in culture, cell supernatants and cell lysates.

Chronic myeloid leukemia. The term "chronic myeloid leukemia" as used herein is characterized by an uncontrolled proliferation of myelopoietic cells in the bone marrow and extramedullary sites in which the malignant myeloblast is able to differentiate and give rise to myelocytes, metamyelocytes, band cells and granulocytes.

Complementarity determining regions (CDR). The term "complementarity determining regions" as used herein means sequences within the variable regions of binding molecules, such as immunoglobulins, that generate the antigen binding site which is complementary in shape and charge distribution to the epitope recognized on the antigen. The CDR regions can be specific for linear epitopes, discontinuous epitopes, or conformational epitopes of proteins or protein fragments, either as present on the protein in its native conformation or, in some cases, as present on the proteins as denatured, e.g., by solubilization in SDS. Epitopes may also consist of post translational modifications of proteins.

C-type lectin. The term "C-type lectin" as used herein relates to a general class of lectins, i.e., proteins that specifically bind carbohydrates of various types and have the ability to agglutinate cells. Typical features of C-type lectins include a calcium-dependent-carbohydrate recognition domain and a set of conserved cysteines allowing intramolecular disulfide bridging. More specifically, six cysteines appear to be conserved in C-type lectins as meant herein. The six conserved cysteines generate three intrachain disulfide bonds that are typical of C-type lectins (see, Colonna et al., 2000, which is incorporated by reference herein). C-type lectins not having a calcium binding site in their carbohydrate recognition domain however also do exist and they are also contemplated as C-type lectins as defined herein as long as they do contain the set of conserved cysteines mentioned above.

Deletion. The term "deletion," as used herein, denotes a change in either amino acid or nucleotide sequence in which one or more amino acid or nucleotide residues, respectively, are absent as compared to the parent, often the naturally occurring, molecule.

Expression-regulating nucleic acid sequence. The term "expression-regulating nucleic acid sequence" as used herein refers to polynucleotide sequences necessary for and/or affecting the expression of an operably linked coding sequence in a particular host organism. When two nucleic acid sequences are operably linked, they usually will be in the same orientation and also in the same reading frame. They usually will be essentially contiguous, although this may not be required. The expression-regulating nucleic acid sequences, such as inter alfa appropriate transcription initiation, termination, promoter, enhancer sequences; repressor or activator sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion, can be any nucleic acid sequence showing activity in the host organism of choice and can be derived from genes encoding proteins, which are either homologous or heterologous to the host organism.

Functional variant. The term "functional variant," as used herein, refers to a binding molecule that comprises a nucleotide and/or amino acid sequence that is altered by one or more nucleotides and/or amino acids compared to the nucleotide and/or amino acid sequences of the parent binding molecule and that is still capable of competing for binding to the binding partner, e.g., a human C-type lectin, with the parent binding molecule. In other words, the modifications in the amino acid and/or nucleotide sequence of the parent binding molecule do not significantly affect or alter the binding characteristics of the binding molecule encoded by the nucleotide sequence or containing the amino acid sequence, i.e., the binding molecule is still able to recognize and bind its target. The functional variant may have conservative sequence modifications including nucleotide and amino acid substitutions, additions and deletions. These modifications can be introduced by standard techniques known in the art, such as site-directed mutagenesis and random PCR-mediated mutagenesis.

Conservative amino acid substitutions include the ones in which the amino acid residue is replaced with an amino acid residue having similar structural or chemical properties. Families of amino acid residues having similar side chains have been defined in the art. These families include amino acids with basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine, tryptophan), nonpolar side chains (e.g., alanine, valine, leucine, isoleucine, proline, phenylalanine, methionine), beta-branched side chains (e.g., threonine, valine, isoleucine) and aromatic side chains (e.g., tyrosine, phenylalanine, tryptophan, histidine). Furthermore, a variant may have non-conservative amino acid substitutions, e.g., replacement of an amino acid with an amino acid residue having different structural or chemical properties. Similar minor variations may also include amino acid deletions or insertions, or both. Guidance in determining which amino acid residues may be substituted, inserted, or deleted without abolishing immunological activity may be found using computer programs well known in the art.

A mutation in a nucleotide sequence can be a single alteration made at a locus (a point mutation), such as transition or transversion mutations, or alternatively, multiple nucleotides may be inserted, deleted or changed at a single locus. In addition, one or more alterations may be made at any number of loci within a nucleotide sequence. The mutations may be performed by any suitable method known in the art.

Host. The term "host," as used herein, is intended to refer to an organism or a cell into which a vector such as a cloning vector or an expression vector has been introduced. The organism or cell can be prokaryotic or eukaryotic. It should be understood that this terms is intended to refer not only to the particular subject organism or cell, but to the progeny of such an organism or cell as well. Because certain modifications may occur in succeeding generations due to either mutation or environmental influences, such progeny may not, in fact, be identical to the parent organism or cell, but are still included within the scope of the term "host" as used herein.

Human. The term "human," when applied to proteins such as for instance binding molecules as defined herein, refers to molecules that are either directly derived from a human or based upon a human sequence. When a protein is derived from or based on a human sequence and subsequently modified, it is still to be considered human as used throughout the specification. In other words, the term "human," when applied specifically to binding molecules is intended to include binding molecules having variable and constant regions derived from human germline immunoglobulin sequences based on variable or constant regions either or not occurring in a human or human lymphocyte or in modified form. Thus, the human binding molecules may include amino acid residues not encoded by human germline immunoglobulin sequences and/or comprise substitutions and/or deletions (e.g., mutations introduced by for instance random or site-specific mutagenesis in vitro or by somatic mutation in vivo). "Based on" as used herein also refers to the situation that a nucleic acid sequence may be exactly copied from a template, or with minor mutations, such as by error-prone PCR methods, or synthetically made matching the template exactly or with minor modifications. Semi-synthetic molecules based on human sequences are also considered to be human as used herein.

Immunoliposome. The term "immunoliposome" refers to a liposome bearing a binding molecule, as defined herein, that acts as a targeting moiety enabling the liposome to specifically bind to the binding partner of the binding molecule. The binding partner may be present in solution or may be bound to the surface of a cell.

Insertion. The term "insertion," also known as the term "addition," denotes a change in an amino acid or nucleotide sequence resulting in the addition of one or more amino acid or nucleotide residues, respectively, as compared to the parent, often the naturally occurring, molecule.

Internalizing binding molecule. The term "internalizing binding molecule" as used herein means a binding molecule as defined herein that is capable of being internalized within the target cells to which it binds. In other words, the binding molecule is taken up, i.e., transported from the outside (cell surface) of a target cell to the inside, e.g., into the endosomal compartment or other compartment or into the cytoplasm of the cell, by the target cells upon binding to the binding partner of the binding molecule.

Isolated. The term "isolated," when applied to proteins refers to proteins that are substantially free of other proteins or polypeptides and that are also substantially free of other cellular material and/or chemicals. In the specific case of binding molecules, the binding molecules should be particularly free of other binding molecules having different antigenic specificities. For example, when binding molecules are recombinantly produced, they are preferably substantially free of culture medium, and when binding molecules are produced by chemical synthesis, they are preferably substantially free of chemical precursors or other chemicals, i.e., they are separated from chemical precursors or other chemicals which are involved in the synthesis of the protein.

The term "isolated" when applied to nucleic acid molecules encoding proteins, is intended to refer to nucleic acid molecules in which the nucleotide sequences encoding the proteins are free of other nucleotide sequences. In case of nucleotide sequences encoding binding molecules as defined herein, the nucleotide sequences should be particularly free of nucleotide sequences encoding binding molecules that bind binding partners other than the human C-type lectin of the invention. Furthermore, the term "isolated" refers to nucleic acid molecules that are substantially separated from other cellular components that naturally accompany the native nucleic acid molecule in its natural host, e.g., ribosomes, polymerases, or genomic sequences with which it is naturally associated. Moreover, "isolated" nucleic acid molecules, such as a cDNA molecules, can be substantially free of other cellular material, or culture medium when produced by recombinant techniques, or substantially free of chemical precursors or other chemicals when chemically synthesized.

Liposome. The term "liposome" as used herein refers to a small vesicle bounded by a layer composed of various types of lipids, preferably amphipathic lipids, phospholipids and/or surfactants and made artificially from these molecules by techniques known in the art such as sonication or removal of detergent from phospholipid-detergent complexes. The layer typically is a bilayer formed by molecules that comprise a hydrophobic portion and a hydrophilic portion, wherein hydrophobic portions associate in an aqueous medium to form an internal part of the layer, whereas hydrophilic portions remain in contact with the medium. The layer surrounds and encloses an interior, which may contain, wholly or partially, an aqueous phase, a solid, a gel, a gas phase, or a non-aqueous fluid. Liposomes are useful for delivery of one or more molecules such as nucleic acid molecules, binding molecules, proteins, toxic substances and other material or compounds into cells such as animal cells by liposome fusion with the plasma membrane, a process also called lipofection. The molecules may be contained within the interior of the liposome, in the lipid layer, or attached to the outer surface of the lipid layer.

Monoclonal antibody. The term "monoclonal antibody" as used herein refers to a monoclonal antibody displaying a single binding specificity and affinity for a particular epitope.

Accordingly, the term "human monoclonal antibody" refers to an antibody displaying a single binding specificity that has variable and constant regions derived from human germline immunoglobulin sequences or derived from completely synthetic sequences.

Myelodysplastic syndrome. The term "myelodysplastic syndrome" as used herein encompasses a heterogeneous group of closely related clonal hematopoietic disorders that originate in an early blood-forming cell in the marrow. All disorders are characterized by a cellular marrow with impaired morphology and maturation (dysmyelopoiesis) and peripheral blood cytopenias, resulting from ineffective blood cell production. In other words, the maturing blood cells often die in the marrow before they reach full maturity and enter the blood, accounting for the low blood cell concentrations. In patients suffering from myelodysplastic syndrome there may also be an accumulation of very immature marrow cells, called leukemic blast cells.

Myeloid cells. The term "myeloid cells" refers to normal or neoplastic cells found in the blood, bone marrow, other hematopoietic or other non-hematopoietic compartments of the body. In particular, the term "myeloid cells" is used herein to mean the cell lineage originating from the bone marrow that includes polymorphonuclear neutrophils, eosinophils, basophils, and mast cells, as well as the monocyte/macrophage lineage and different dendritic cell lineages. Myeloid cells are not capable of differentiating into lymphoid cells (e.g., NK-, B- and T-lymphocytes). The term refers to cells of the myeloid lineages in all stages of their differentiation and therefore includes hematopoietic blast cells, i.e., hematopoietic cells that are committed to the myeloid cell lineage, but that are in early stages of differentiation. When stimulated with appropriate growth factors, hematopoietic blast cells divide to produce a large number of cells that are more differentiated than the blast stage of differentiation. Examples are inter alia myeloblasts.

Cells that are more differentiated than blasts but not yet fully differentiated are appended with the prefix "pro" and are also intended to fall under the definition of "myeloid cells." Examples are promyelocytes.

The term "myeloid cells" also includes myeloid progenitor cells, i.e., cell lineages, e.g., in the bone marrow, that are capable of differentiating in cells such as myelomonocytic progenitor cells, proerythroblasts or immature megakaryoblasts. Myeloid progenitor cells are not capable of giving rise to lymphoid cells.

The term "myeloid cells" does not include lympho-hematopoietic stem cells. Lympho-hematopoietic stem cells are defined as those cells that are capable of both self-renewal and differentiation into the two principle precursor components, the myeloid and lymphoid lines. Such stem cells are said to be totipotent. Stem cells that are less general but that can still differentiate into several lines are called pluripotent.

Myeloid leukemia. The term "myeloid leukemia" as used herein refers to leukemia characterized by proliferation of myeloid tissue and an abnormal increase in the number of granulocytes, myelocytes and myeloblasts in the circulating blood. This term is synonymous with the terms myelocytic leukemia, myelogenic leukemia, myelogenous leukemia and granulocytic leukemia.

The term "myeloid leukemia" represent, inter alia, acute and chronic myeloid leukemias (AML and CML), acute promyelocytic leukemia (APL), chronic myelomonocytic leukemia ("CMML"), myelodysplastic syndrome and juvenile myelomonocytic leukemia which involve the myeloid elements of the bone marrow (e.g., white cells, red cells and megakaryocytes) and includes all subtypes which are defined by morphological, histochemical and immunological techniques that are well known by those skilled in the art. Subtypes of AML include according to the FAB classification FAB-M0, FAB-M1, FAB-M2, FAB-M3, FAB-M4, FAB-M5, FAB-M6 and FAB-M7.

Naturally occurring. The term "naturally occurring" as used herein as applied to an object refers to the fact that an object can be found in nature. For example, a polypeptide or polynucleotide sequence that is present in an organism that can be isolated from a source in nature and which has not been modified by man in the laboratory is naturally occurring.

Neoplastic cells. The term "neoplastic cells" as used herein refers to cells that result from undesired autonomous new growth which has no apparent physiological function. A neoplastic cell further includes transformed cells and cancer cells including blood cancers (benign and malignant).

Nucleic acid molecule. The term "nucleic acid molecule" as used herein refers to a polymeric form of nucleotides and includes both sense and antisense strands of RNA, cDNA, genomic DNA, and synthetic forms and mixed polymers of the above. A nucleotide refers to a ribonucleotide, deoxynucleotide or a modified form of either type of nucleotide. The term also includes single- and double-stranded forms of DNA. In addition, a polynucleotide may include either or both naturally occurring and modified nucleotides linked together by naturally occurring and/or non-naturally occurring nucleotide linkages. The nucleic acid molecules may be modified chemically or biochemically or may contain non-natural or derivatized nucleotide bases, as will be readily appreciated by those of skill in the art. Such modifications include, for example, labels, methylation, substitution of one or more of the naturally occurring nucleotides with an analog, internucleotide modifications such as uncharged linkages (e.g., methyl phosphonates, phosphotriesters, phosphoramidates, carbamates, etc.), charged linkages (e.g., phosphorothioates, phosphorodithioates, etc.), pendent moieties (e.g., polypeptides), intercalators (e.g., acridine, psoralen, etc.), chelators, alkylators, and modified linkages (e.g., alpha anomeric nucleic acids, etc.) The above term is also intended to include any topological conformation, including single-stranded, double-stranded, partially duplexed, triplex, hairpinned, circular and padlocked conformations. Also included are synthetic molecules that mimic polynucleotides in their ability to bind to a designated sequence via hydrogen bonding and other chemical interactions. Such molecules are known in the art and include, for example, those in which peptide linkages substitute for phosphate linkages in the backbone of the molecule. A reference to a nucleic acid sequence encompasses its complement unless otherwise specified. Thus, a reference to a nucleic acid molecule having a particular sequence should be understood to encompass its complementary strand, with its complementary sequence. The complementary strand is also useful, e.g., for antisense therapy, hybridization probes and PCR primers.

Operably linked. The term "operably linked" refers to two or more nucleic acid sequence elements that are physically linked and are in a functional relationship with each other. For instance, a promoter is operably linked to a coding sequence if the promoter is able to initiate or regulate the transcription or expression of a coding sequence, in which case the coding sequence should be understood as being "under the control of" the promoter. Generally, when two nucleic acid sequences are operably linked, they will be in the same orientation and usually also in the same reading frame. They usually will be essentially contiguous, although this may not be required.

Pharmaceutically acceptable excipient. By "pharmaceutically acceptable excipient" is meant any inert substance that is combined with an active molecule such as a drug, agent, or binding molecule for preparing an agreeable or convenient dosage form. The "pharmaceutically acceptable excipient" is an excipient that is non-toxic to recipients at the dosages and concentrations employed and is compatible with other ingredients of the formulation comprising the drug, agent, or binding molecule.

Specifically Binding. The term "specifically binding," as used herein, in reference to the interaction of a binding molecule, e.g., an antibody, and its binding partner, e.g., an antigen, means that the interaction is dependent upon the presence of a particular structure, e.g., an antigenic determinant or epitope, on the binding partner. In other words, the antibody preferentially binds or recognizes the binding partner even when the binding partner is present in a mixture of other molecules. The binding may be mediated by covalent or non-covalent interactions or a combination of both.

Substitutions. A "substitution," as used herein, denotes the replacement of one or more amino acids or nucleotides by different amino acids or nucleotides, respectively.

Therapeutically effective amount. The term "therapeutically effective amount" refers to an amount of the binding molecule as defined herein that is effective for preventing, treating a disorder or disease wherein the human C-type lectin molecules play a role or are associated with, or ameliorating a condition associated with the disease or disorder.

Treatment. The term "treatment" refers to therapeutic treatment as well as prophylactic or preventative measures. Those in need of treatment include those already with the disease or disorder wherein the human C-type lectin molecule plays a role or is associated with as well as those in which the disease or disorder is to be prevented.

Vector. The term "vector" denotes a nucleic acid molecule into which a second nucleic acid molecule can be inserted for introduction into a host where it will be replicated, and in some cases expressed. In other words, a vector is capable of carrying a second nucleic acid molecule to which it has been linked. Cloning as well as expression vectors are contemplated by the term "vector," as used herein. Vectors include, but are not limited to, plasmids, cosmids, bacterial artificial chromosomes (BAC) and yeast artificial chromosomes (YAC) and vectors derived from bacteriophages or plant or animal (including human) viruses. Vectors comprise an origin of replication recognized by the proposed host and in case of expression vectors, promoter and other regulatory regions recognized by the host. A vector containing a second nucleic acid molecule is introduced into a cell by transformation, transfection, or by making use of viral entry mechanisms. Certain vectors are capable of autonomous replication in a host into which they are introduced (e.g., bacterial vectors having a bacterial origin of replication). Other vectors can be integrated into the genome of a host upon introduction into the host, and thereby are replicated along with the host genome.

The invention pertains to a new human C-type lectin. The human C-type lectin of the invention comprises the amino acid sequence YX$_1$X$_2$M (SEQ ID NO:33), wherein X$_1$ and X$_2$ may be any amino acid residue and wherein X$_1$ and X$_2$ may be the same or different from one another. Preferably, X$_1$ and X$_2$ are S. This amino acid motif is deemed to be involved in internalization.

Besides this motif, typical features of C-type lectins include a calcium-dependent or calcium-independent-carbohydrate recognition domain and a set of conserved cysteines allowing intramolecular disulfide bridging. The human C-type lectin of the invention comprises six conserved cysteines within its carbohydrate recognition domain that generate three intrachain disulfide bonds that are typical of C-type lectins (for an alignment of several C-type lectins see Colonna et al., 2000, which is incorporated by reference herein). The six conserved cysteine residues can be found in the amino acid sequence presented in SEQ ID NO:2 at the positions 143, 154, 171, 237, 250 and 258. Next to the six cysteine residues, the human C-type lectins of the invention might contain at least one of the following conserved amino acids which can also be found within the carbohydrate recognition domain: tryptophan (see, position 147 of the amino acid sequence of SEQ ID NO:2), tryptophan (see, position 164 of the amino acid sequence of SEQ ID NO:2), leucine (see, position 178 of the amino acid sequence of SEQ ID NO:2), phenylalanine (see, position 189 of the amino acid sequence of SEQ ID NO:2), tryptophan (see, position 200 of the amino acid sequence of SEQ ID NO:2), glycine-leucine (see, positions 202 and 203 of the amino acid sequence of SEQ ID NO:2, respectively) and aspartic acid (see, position 216 of the amino acid sequence of SEQ ID NO:2).

In a preferred embodiment the human C-type lectin of the invention comprises an amino acid sequence comprising the amino acid residues 1-10 of SEQ ID NO:2.

The human C-type lectin of the invention is exclusively expressed by myeloid cells including, but not limited to, monocytes, granulocytes, mature and precursor peripheral blood myeloid dendritic cells. The human C-type lectin of the invention is also expressed by neoplastic myeloid cells including, but not limited to, myeloid cells of a patient having a disease or disorder selected from the group consisting of acute myeloid leukemia, chronic myeloid leukemia, chronic myelomonocytic leukemia, acute promyelocytic leukemia, myelodysplastic syndrome, juvenile myelomonocytic leukemia, and Langerhans cell histiocytosis.

In certain embodiments, the human C-type lectin of the invention comprises an amino acid sequence having a homology of at least 97% with the amino acid sequence of SEQ ID NO:2. Preferably, the human C-type lectin of the invention comprises an amino acid sequence having a homology of at least 98% with the amino acid sequence of SEQ ID NO:2. More preferably, the human C-type lectin of the invention comprises an amino acid sequence having a homology of at least 99% with the amino acid sequence of SEQ ID NO:2. In a particularly preferred embodiment the human C-type lectin of the invention comprises an amino acid sequence having the amino acid sequence of SEQ ID NO:2. The human C-type lectin of the invention is a type-II transmembrane protein having an intracellular region of 53 amino acids, a transmembrane region of 23 amino acids and an extracellular domain of 199 amino acids. In addition, the cytoplasmic domain of the human C-type lectin contains an I/VX$_1$YX$_2$X$_3$L (SEQ ID NO:34) immunotyrosine-based inhibition motif ("ITIM"), wherein X$_1$, X$_2$ and X$_3$ may be any amino acid residue and wherein X$_1$, X$_2$ and X$_3$ may be the same or different from one another. Phosphorylation of ITIM-containing receptors on a variety of cells can lead to inhibition of activation pathways via recruitment of the protein tyrosine phosphatases SHP-1, SHP-2 and SHIP.

The YX$_1$X$_2$M (SEQ ID NO:33) motif present in the human C-type lectin of the invention can encompass a potential SH2 domain-binding site for the p85 subunit of the PI-3 kinase, an enzyme implicated in cellular activation pathways. Besides its role in PI-3 kinase recruitment, the YX$_1$X$_2$M (SEQ ID NO:33) motif has been demonstrated to function as an internalization motif (Chuang et al. 1997; Wu et al. 2003). Therefore, this motif might be responsible for the observed internalization of the human C-type lectin upon antibody-mediated cross-linking.

In a specific embodiment, the human C-type lectin may be used as a marker for myeloid diseases and/or disorders and may also be used to obtain binding molecules capable of specifically binding to it.

Also encompassed are binding molecules capable of specifically binding to the human C-type lectin of the invention. The binding molecules are also capable of binding, particularly specifically binding, to a fragment of the human C-type lectin of the invention, the fragment at least comprising the antigenic determinant of the human C-type lectin.

A human C-type lectin comprising naturally occurring truncated or secreted forms, naturally occurring variant forms (e.g., alternatively spliced forms) and naturally occurring allelic variants of the human C-type lectin of the invention, particularly the human C-type lectin containing an amino acid sequence as shown in SEQ ID NO:2, are also a part of the invention. Binding molecules of the invention may also be capable of specifically binding to non-naturally occurring variants or analogues of the human C-type lectin of the invention, particularly the human C-type lectin containing the amino acid sequence of SEQ ID NO:2, as long as the modifications do not abolish the binding of the binding molecules to the C-type lectin.

The nucleotide sequence of the human C-type lectin comprises a nucleotide sequence encoding an amino acid sequence as mentioned above, preferably an amino acid sequence as shown in SEQ ID NO:2. More preferably, the nucleotide sequence encoding the human C-type lectin comprises the nucleotide sequence as shown in SEQ ID NO:1. In a specific embodiment the nucleic acid molecule encoding the human C-type lectin of the invention may be used as a vaccine or for making a vaccine.

The binding molecules according to the invention are preferably human binding molecules. They can be intact immunoglobulin molecules such as polyclonal or monoclonal antibodies, in particular human monoclonal antibodies, or the binding molecules can be antigen-binding fragments including, but not limited to, Fab, F(ab'), F(ab')$_2$, Fv, dAb, Fd, complementarity determining region (CDR) fragments, single-chain antibodies (scFv), bivalent single-chain antibodies, diabodies, triabodies, tetrabodies, and peptides or polypeptides ("(poly)peptides") that contain at least a fragment of an immunoglobulin that is sufficient to confer specific antigen binding to the (poly)peptides. The binding molecules of the invention can be used in non-isolated or isolated form. Furthermore, the binding molecules of the invention can be used alone or in a mixture comprising at least one binding molecule (or variant or fragment thereof). In other words, the binding molecules can be used in combination, e.g., as a pharmaceutical composition comprising two or more binding molecules or fragments thereof. For example, binding molecules having different, but complementary, activities can be combined in a single therapy to achieve a desired therapeutic or diagnostic effect, but alternatively, binding molecules having identical activities can also be combined in a single therapy to achieve a desired therapeutic or diagnostic effect. The mixture may further comprise at least one other therapeutic agent. Typically, binding molecules according to the invention can bind to their binding partners, i.e., a human C-type lectin of the invention, with an affinity constant (Kd-value) that is lower than $0.2*10^{-4}$ M, $1.0*10^{-5}$ M, $1.0*10^{-6}$ M, $1.0*10^{-7}$ M, preferably lower than $1.0*10^{-8}$ M, more preferably lower than $1.0*10^{-9}$ M, more preferably lower than $1.0*10^{-10}$ even more preferably lower than $1.0*10^{-11}$ M, and in particular lower than $1.0*10^{-12}$ M. The affinity constants can vary for antibody isotypes. For example, affinity binding for an IgM isotype refers to a binding affinity of at least about $1.0*10^{-7}$ M. Affinity constants can be measured using surface plasmon resonance, i.e., an optical phenomenon that allows for the analysis of real-time biospecific interactions by detection of alterations in protein concentrations within a biosensor matrix, for example, using the BIAcore® system (Pharmacia Biosensor AB, Uppsala, Sweden).

The binding molecules herein may bind to a human C-type lectin of the invention in soluble form or may bind to a human C-type lectin of the invention bound or attached to a carrier or substrate, e.g., microtiter plates, membranes and beads, etc. Carriers or substrates may be made of glass, plastic (e.g., polystyrene), polysaccharides, nylon, nitrocellulose, or TEFLON®, etc. The surface of such supports may be solid or porous and of any convenient shape. Furthermore, the binding molecules may bind to the human C-type lectin in purified or non-purified form and/or in isolated or non-isolated form. Preferably, the binding molecules are capable of specifically binding to the human C-type lectin associated with cells, such as a human C-type lectin-positive cells, e.g., myeloid cells or cells transfected with the human C-type lectin of the invention, or portions or parts of these cells comprising the human C-type lectin or a fragment thereof. As the human C-type lectin according to the invention is specifically expressed by myeloid cells as defined herein, the binding molecules according to the invention can be used to selectively target myeloid cells.

In certain embodiments, the myeloid cells are neoplastic cells, preferably neoplastic myeloid cells such as myeloid leukemia cells. Myeloid leukemia cells according to the invention include, but are not limited to, acute myeloid leukemia cells, myelodysplastic syndrome cells, chronic myeloid leukemia cells, chronic myelomonocytic leukemia cells, acute promyelocytic leukemia cells, juvenile myelomonocytic leukemia cells, Langerhans cell histiocytosis cells and combinations thereof. Preferably, the myeloid leukemia cells comprise acute myeloid leukemia cells, myelodysplastic syndrome cells or a combination thereof. Particularly preferred myeloid leukemia cells comprise acute myeloid leukemia cells.

In certain embodiments, the binding molecules of the invention which stay bound to the surface upon binding to the human C-type lectin present on the surface of target cells, such as myeloid cells, preferably neoplastic myeloid cells, may be used in the format of naked binding molecules to support possible effector functions of antibody-dependent cellular cytotoxicity (ADCC) and complement-dependent cytotoxicity (CDC). ADCC refers to a cell-mediated reaction in which nonspecific cytotoxic cells that express Fc receptors (FcRs) (e.g., Natural Killer (NK) cells, neutrophils, and macrophages) recognize the so-called Fc portion of binding molecules while the latter bind to a target cell and subsequently cause lysis of the target cell. CDC refers to the ability of a molecule to lyse a target in the presence of complement. The complement activation pathway is initiated by the binding of the first component of the complement system (C1q) to a binding molecule complexed with a cognate antigen. To distinguish cell death induced by antibody-dependent cell-mediated/cellular cytotoxicity (ADCC) or complement-dependent cytotoxicity (CDC), cell death may be determined in vitro in the absence of complement and immune effector cells. The assay for cell death may for instance be performed using heat inactivated serum (i.e., in the absence of complement) and in the absence of immune effector cells. To determine whether the binding molecule is able to induce cell death, loss of membrane integrity as evaluated by uptake of propidium iodide (PI), trypan blue or 7AAD can be assessed relative to untreated cells.

Naked antibodies according to the invention may also induce apoptosis of target cells in another way than by means of ADCC or CDC. Target cells include, but are not limited to, human C-type lectin-positive cells such as myeloid cells, preferably neoplastic myeloid cells. Methods of measuring apoptosis are known to a skilled artisan and include, but are not limited to, FACS analysis using Annexin V staining, DNA electrophoresis, uptake of propidium iodide (PI), trypan blue or 7AAD.

In a preferred embodiment, the binding molecules internalize upon binding to the human C-type lectin of the invention present on the surface of target cells. Internalization of binding molecules can be assayed by known techniques that include, but are not limited to, specifically tracing internalized binding molecules capable of binding the human C-type lectin of the invention that are labeled with a fluorochrome using flow cytometry or confocal scanning laser microscopy.

In case the binding molecules as defined in the invention are slowly internalizing and, before internalization, stay bound to the surface of target cells for a prolonged period of time, they may even be useful, similarly as binding molecules that do not internalize at all, in therapies which make use of ADCC, CDC, apoptosis or ADEPT.

In another embodiment, provided are binding molecules that upon binding/interaction with the human C-type lectin of the invention exert a similar effect or trigger/activate a similar downstream process as the molecule normally binding to the human C-type lectin of the invention. In other words, the binding molecules may be capable, when combined with the human C-type lectin of the invention on a cell, of binding to the human C-type lectin of the invention and activating/starting a downstream process that is similar to or the same as that activated/started by the C-type lectins natural ligand. The binding molecules are preferably against epitopes within the extracellular domain of the human C-type lectin of the invention. Such binding molecules cover inter alia human anti-human C-type lectin monoclonal antibodies or parts thereof and human anti-human C-type lectin compositions with polyepitopic specificity.

In a preferred embodiment, the binding molecules comprise at least a CDR3 region, preferably a heavy chain CDR3 region, comprising the amino acid sequence selected from the group consisting of SEQ ID NO:3 (VSTGGFFDY), SEQ ID NO:4 (SSSGGFFDY) and SEQ ID NO:5 (QTTAGSFDY).

In yet another embodiment, the binding molecules comprise a heavy chain comprising an amino acid sequence selected from the group consisting of SEQ ID NO:7, SEQ ID NO:9 and SEQ ID NO:11.

In a further embodiment, the binding molecules comprise a heavy chain comprising the amino acid sequence shown in SEQ ID NO:7 and a light chain comprising the amino acid sequence of SEQ ID NO:13, a heavy chain comprising the amino acid sequence shown in SEQ ID NO:9 and a light chain comprising the amino acid sequence of SEQ ID NO:13 or a heavy chain comprising the amino acid sequence shown in SEQ ID NO:11 and a light chain comprising the amino acid sequence of SEQ ID NO:13. Plasmids comprising DNA encoding the heavy chain or light chain of human IgG1 antibodies directed against the human C-type lectin (the antibodies being called 357, 378 and 161), the plasmids being called pcDNA-SY-HC357, pcDNA-SY-HC378, pcDNA-SY-HC161 and pcDNA-SY-LC-Vκ1, were deposited at the European Collection of Cell Cultures (ECACC), CAMR, Salisbury, Wiltshire SP4 OJG, Great Britain on 24 Jun. 2003, under provisional accession numbers 03062402, 03062403, 03062401 and 03062404, respectively.

Another aspect of the invention includes functional variants of binding molecules or fragments thereof as defined herein. Molecules are considered to be functional variants of a binding molecule, if the variants are capable of competing for specifically binding to the human C-type lectins of the invention, particularly the human C-type lectin comprising the amino acid sequence as shown in SEQ ID NO:2, preferably competing for the same binding site on the human C-type lectin, with the parent binding molecules. In other words, when the functional variants are still capable of binding to the human C-type lectin or a portion thereof. Functional variants include, but are not limited to, derivatives that are substantially similar in primary structural sequence, but which contain e.g., in vitro or in vivo modifications, chemical and/or biochemical, that are not found in the parent binding molecule. Such modifications include inter alia acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent cross-links, formation of cysteine, formation of pyroglutamate, formylation, gamma-carboxylation, glycosylation, GPI-anchor formation, hydroxylation, iodination, methylation, myristoylation, oxidation, pegylation, proteolytic processing, phosphorylation, prenylation, racemization, selenoylation, sulfation, transfer-RNA-mediated addition of amino acids to proteins such as arginylation, ubiquitination, and the like.

Alternatively, functional variants can be binding molecules as defined in the invention comprising an amino acid sequence containing substitutions, insertions, deletions or combinations thereof of one or more amino acids compared to the amino acid sequences of the parent binding molecules. Furthermore, functional variants can comprise truncations of the amino acid sequence at either or both the amino or carboxy termini. Functional variants according to the invention may have the same or different, either higher or lower, binding affinities compared to the parent binding molecule but are still capable of binding to the human C-type lectins of the invention present on, e.g., a cell. For instance, functional variants according to the invention may have increased or decreased binding affinities for the human C-type lectins of the invention compared to the parent binding molecules. Preferably, the amino acid sequences of the variable regions, including, but not limited to, framework regions, hypervariable regions, in particular the CDR3 regions, are modified. Generally, the light chain and the heavy chain variable regions comprise three hypervariable regions, comprising three CDRs, and more conserved regions, the so-called framework regions (FRs). The hypervariable regions comprise amino acid residues from CDRs and amino acid residues from hypervariable loops. Functional variants intended to fall within the scope of the invention have at least about 50% to about 99%, preferably at least about 60% to about 99%, more preferably at least about 70% to about 99%, even more preferably at least about 80% to about 99%, most preferably at least about 90% to about 99%, in particular at least about 95% to about 99%, and, in particular, at least about 97% to about 99% amino acid sequence homology with the parent binding molecules as defined herein. Computer algorithms such as inter alia Gap or Bestfit known to a person skilled in the art can be used to optimally align amino acid sequences to be compared and to define similar or identical amino acid residues.

Functional variants can be obtained by altering the parent binding molecules or parts thereof by general molecular biology methods known in the art including, but not limited to, error-prone PCR, oligonucleotide-directed mutagenesis and site-directed mutagenesis.

In yet a further aspect, the invention includes immunoconjugates, i.e., molecules comprising at least one binding molecule as defined herein and further comprising at least one tag, such as a therapeutic moiety that inhibits or prevents the function of cells and/or causes destruction of cells. Also contemplated in the invention are mixtures of immunoconjugates according to the invention or mixtures of at least one immunoconjugates according to the invention and another molecule, such as a therapeutic agent or another binding molecule or immunoconjugate. In a further embodiment, the immunoconjugates of the invention may comprise more than one tag. These tags can be the same or distinct from each other and can be joined/conjugated non-covalently to the binding molecules. The tags can also be joined/conjugated directly to the binding molecules through covalent bonding, including, but not limited to, disulfide bonding, hydrogen bonding, electrostatic bonding, recombinant fusion and conformational bonding. Alternatively, the tags can be joined/conjugated to the binding molecules by means of one or more linking compounds. Techniques for conjugating tags to binding molecules, are well known, see, e.g., Arnon et al., "Monoclonal Antibodies For Immunotargeting Of Drugs In Cancer Therapy," p. 243-256 in *Monoclonal Antibodies And Cancer Therapy* (1985), edited by Reisfeld et al., A. R. Liss, Inc.; Hellstrom et al., "*Antibodies For Drug Delivery,*" *p.* 623-653 in *Controlled Drug Delivery,* 2nd edition (1987), edited by Robinson et al., Marcel Dekker, Inc.; Thorpe, "Antibody Carriers Of Cytotoxic Agents," p. 475-506 *In Cancer Therapy: A Review, in Monoclonal Antibodies* 84: *Biological And Clinical Applications* (1985), edited by Pinchera et al.; "Analysis, Results, And Future Prospective Of The Therapeutic Use Of Radiolabeled Antibody In Cancer Therapy," p. 303-316 in *Monoclonal Antibodies For Cancer Detection And Therapy* (1985), edited by Baldwin et al., Academic Press.

Tags include, but are not limited to, toxic substances, radioactive substances, liposomes, enzymes, polynucleotide sequences, plasmids, proteins, peptides or combinations thereof. Toxic substances include, but are not limited to, cytotoxic agents, such as small molecule toxins or chemotherapeutic agents, or enzymatically active toxins of bacterial, fungal, plant or animal origin, or fragments thereof. Examples of cytotoxic agents include, but are not limited to, alkylating agents such as thiotepa and cyclophosphamide; alkyl sulfonate such as busulfan, improsulfan and piposulfan; aziridines such as benzodopa, carboquone, meturedopa, and uredopa; ethylenimines and methylamelamines such as altretamine, triethylenemelamine, trietylenephosphoramide, triethylenethiophosphoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembiehin, phenesterine, prednimustine, trofosfamide, uracil mustard; nitrosoureas such as carmustine, chlorozotocin, fotemustine, lomustine, nimustine, ranimustine; antibiotics such as aclacinomysins, actinomycin, authramycin, azaserine, bleomycin, cactinomycin, calicheamicin, carabicin, caminomycin, carzinophilin, chromoinycins, dactinomycin, daunorubicin, detorubicin, 6-diazo-5-oxo-L-norleucine, doxorubicin, epirubicin, esorubicin, idarubicin, marcellomycin, mitomycin, mycophenolic acid, nogalamycin, olivomycin, peplomycin, potfiromycin, puromycin, quelamycin, rodorubicin, streptonigrin, streptozocin, tubercidin, ubenimex, zinostatin, zorubicin; macrolide antibiotics such as geldanamicin and maytansin, anti-metabolites such as methotrexate and 5-fluorouracil; folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; platinum analogs such as cisplatin and carboplatin; triazenes; epipodophyllotoxins; platinum coordination complexes; maytansinoids; and taxoids, such as paclitaxel and doxetaxel. Pharmaceutically acceptable salts, acids or derivatives of any one of the above are also included in the invention. In general, suitable chemotherapeutic agents are described in *Remington's Pharmaceutical Sciences,* 18th edition (1990), edited by A. R. Gennaro, Mack Publishing Co., Philadelphia, and in Goodman and Gilman's *The Pharmacological Basis of Therapeutics,* 7th edition (1985), edited by A. G. Gilman, L. S. Goodman, T. W. Rall and F. Murad. MacMillan Publishing Co., New York. Suitable chemotherapeutic agents that are still in the experimental phase are known to those of skill in the art and might also be used as toxic substances in the invention.

Examples of enzymatically active toxins of bacterial, fungal, plant or animal origin include, but are not limited to, ricin A chain, modeccin A chain, abrin A chain, *Pseudomonas* exotoxin and endotoxin A chain, shiga toxin A, anthrax toxin lethal factor, diphteria A chain, nonbinding active fragments of diphtheria toxin, staphylococcal enterotoxin A, the human ribonuclease angiogenin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, tricothecenes, saporin, alpha-sarcin, and fragments or derivatives thereof. Fusion proteins comprising enzymatically active toxins and binding molecules of the immunoconjugate of the invention can be produced by methods known in the art such as, e.g., recombinantly by constructing nucleic acid molecules comprising nucleotide sequences encoding the binding molecules in frame with nucleotide sequences encoding the enzymatically active toxin and then expressing the nucleic acid molecules. Alternatively, fusion proteins can be produced chemically by conjugating, directly or indirectly via for instance a linker, binding molecules as defined herein to enzymatically active toxins.

Immunoconjugates comprising enzymes may be useful in antibody-directed enzyme-prodrug therapy (ADEPT). In this technique enzymes are conjugated to binding molecules. This conjugation converts the enzymes into inactive prodrugs. The binding molecule-enzyme conjugates are then administered and bind to the binding partner of the binding molecule. After clearance of the conjugates from the circulation, prodrugs are administered, which are converted into active drugs by the enzyme of the conjugates. Passive uptake of the active drugs into the target cells will then occur.

Also contemplated are binding molecules of the immunoconjugate of the invention that are labeled with radionuclides. Suitable radionuclides include, but are not limited to, radionuclides that emit alpha radiation such as inter alia $^{212}$bismuth, $^{213}$bismuth and $^{211}$astatine; radionuclides that emit beta radiation such as inter alia $^{131}$iodine, $^{90}$yttrium, $^{186}$rhodium and $^{188}$rhodium; and radionuclides that emit gamma radiation such as inter alia $^{131}$iodine, $^{186}$rhodium and $^{188}$rhodium. Suitable radionuclides further include, but are not limited to, Auger-electron-emitting radionuclides such as inter alia $^{123}$iodine, $^{124}$iodine, $^{125}$iodine, $^{129}$iodine, $^{131}$iodine, $^{111}$indium, $^{77}$bromine, and other radiolabeled halogens. The skilled person will appreciate that other suitable radionuclides can also be identified as suitable in the invention. The choice of radionuclide will be dependent on many factors such as, e.g., the type of disease to be treated, the stage of the disease to be treated, the patient to be treated and the like. Binding molecules can be attached to radionuclides directly or indirectly via a chelating agent by methods well known in the art.

In another embodiment, the binding molecules of the immunoconjugate of the invention can be conjugated to liposomes to produce so-called immunoliposomes. A liposome may be conjugated to one or more binding molecules, the binding molecules being either the same or different. A variety of methods are available for preparing liposomes. These methods are well known in the art and include, but are not limited to, sonication, extrusion, high pressure/homogenization, microfluidization, detergent dialysis, calcium-induced fusion of small liposome vesicles, and ether-infusion methods. The liposomes may be multilamellar vesicles, but preferably the liposomes are unilamellar vesicles such as small unilamellar (200-500 Å) or large unilamellar vesicles (500-5000 Å). After preparation, the liposomes which have not been sized during formation may be sized by methods known in the art to achieve a desired size range and relatively narrow distribution of liposome sizes. The methods of loading drugs into liposomes are well known to those of skill in the art. The most common methods include the encapsulation technique and the transmembrane potential loading method. In the encapsulation technique, the drugs and liposome components are dissolved in an organic solvent or mixture of solvents in which all species are miscible, and then concentrated to a dry film. A buffer is then added to the dried film and liposomes are formed having the drugs incorporated into the vesicle walls. This method has been described in detail in U.S. Pat. Nos. 4,885,172, 5,059,421, and 5,171,578, the contents of which are incorporated herein by reference. The transmembrane potential loading method has been described in detail in U.S. Pat. Nos. 4,885,172, 5,059,421, 5,171,578, 5,316,771, and 5,380,531, the contents of which are also incorporated herein by reference. As will be understood, the loading techniques are not limited to these two general loading techniques.

The drugs that can be loaded into liposomes include, but are not limited to, the toxic substances mentioned above. Liposomes having loaded different drugs and different liposomes, each liposome having loaded one kind of drug, may be alternative embodiments of liposomes that can be used and these embodiments are therefore also contemplated in the invention. Binding molecules of the invention may be attached at the surface of the liposomes or to the terminus of polymers such as polyethylene glycol that are grafted at the surface of the liposomes using conventional chemical-coupling techniques. An advantage of immunoliposomes is the ability to deliver several tens of thousands of drug molecules with a few tens of binding molecules per liposome resulting in high drug to binding molecule ratios. Following binding of the immunoliposomes to the target cells the drug can either, in case of binding molecules that are slowly internalized or not internalized at all, be gradually released from the immunoliposomes and taken up by the cells as a free drug using standard uptake mechanisms or, in case of binding molecules that are rapidly internalized, the immunoliposomes themselves are taken up by the target cells by receptor-mediated endocytosis and the drugs are gradually released within the cells.

In yet another embodiment, the binding molecules may be linked to water-soluble, biodegradable polymers, such as for instance polymers of hydroxypropylmethacrylamine (HPMA). The polymers have toxic substances linked on separate sites of the polymers with the use of appropriate degradable spacers to allow for release of the toxic substances. The above described polymers are also called immunopolymers.

In another aspect, the binding molecules may be conjugated/attached to one or more antigens. Preferably, these antigens are antigens which are recognized by the immune system of a subject to which the binding molecule-antigen conjugate is administered. The antigens may be identical but may also be different. Conjugation methods for attaching the antigens and binding molecules are well known in the art and include, but are not limited to, the use of cross-linking agents. The binding molecules will bind to the cells comprising the human C-type lectin and the antigens attached to the binding molecules will initiate a powerful T-cell attack on the conjugate which will eventually lead to the destruction of the cell.

Alternatively, the binding molecules as described herein can be conjugated to tags and be used for detection and/or analytical and/or diagnostic purposes. The tags used to label the binding molecules for those purposes depend on the specific detection/analysis/diagnosis techniques and/or methods used such as inter alia immunohistochemical staining of tissue samples, flow cytometric detection, scanning laser cytometric detection, fluorescent immunoassays, enzyme-linked immunosorbent assays (ELISAs), radioimmunoassays (RIAs), bioassays (e.g., growth inhibition assays), Western blotting applications, etc. For immunohistochemical staining of tissue samples preferred labels are enzymes that catalyze production and local deposition of a detectable product. Enzymes typically conjugated to binding molecules to permit their immunohistochemical visualization are well known and include, but are not limited to, alkaline phosphatase, P-galactosidase, glucose oxidase, horseradish peroxidase, and urease. Typical substrates for production and deposition of visually detectable products include, but are not limited to, o-nitrophenyl-beta-D-galactopyranoside (ONPG), o-phenylenediamine dihydrochloride (OPD), p-nitrophenyl phosphate (PNPP), p-nitrophenyl-beta-D-galactopryanoside (PNPG), 3', 3'diaminobenzidine (DAB), 3-amino-9-ethylcarbazole (AEC), 4-chloro-1-naphthol (CN), 5-bromo-4-chloro-3-indolyl-phosphate (BCIP), ABTS, BluoGal, iodonitrotetrazolium (INT), nitroblue tetrazolium chloride (NBT), phenazine methosulfate (PMS), phenolphthalein monophosphate (PMP), tetramethyl benzidine (TMB), tetranitroblue tetrazolium (TNBT), X-Gal, X-Gluc, and X-glucoside. Other substrates that can be used to produce products for local deposition are luminescent substrates. For example, in the presence of hydrogen peroxide, horseradish peroxidase can catalyze the oxidation of cyclic diacylhydrazides such as luminol. The binding molecules of the immunoconjugate of the invention can also be labeled using colloidal gold or they can be labeled with radioisotopes, such as $^{33}$P, $^{32}$P, $^{35}$S, $^{3}$H, and $^{125}$I. When the binding molecules of the invention are used for flow cytometric detections, scanning laser cytometric detections, or fluorescent immunoassays, they can usefully be labeled with fluorophores. A wide variety of fluorophores useful for fluorescently labeling the binding molecules of the invention include, but are not limited to, Alexa Fluor and Alexa Fluor and commat dyes, BODIPY dyes, Cascade Blue, Cascade Yellow, Dansyl, lissamine rhodamine B, Marina Blue, Oregon Green 488, Oregon Green 514, Pacific Blue, rhodamine 6G, rhodamine green, rhodamine red, tetramethylrhodamine, Cy2, Cy3, Cy3.5, Cy5, Cy5.5, Cy7, fluorescein isothiocyanate (FITC), allophycocyanin (APC), R-phycoerythrin (PE), peridinin chlorophyll protein (PerCP), Texas Red, fluorescence resonance energy tandem fluorophores such as PerCP-Cy5.5, PE-Cy5, PE-Cy5.5, PE-Cy7, PE-Texas Red, and APC-Cy7. When the binding molecules of the invention are used for secondary detection using labeled avidin, streptavidin, captavidin or neutravidin, the binding molecules may be labeled with biotin.

The binding molecules may be conjugated to photoactive agents or dyes such as fluorescent and other chromogens or dyes to use the so obtained immunoconjugates in photoradiation, phototherapy, or photodynamic therapy. The photoactive agents or dyes include, but are not limited to, Photofrin®, synthetic diporphyrins and dichlorins, phthalocyanines with or without metal substituents, chloroaluminum phthalocyanine with or without varying substituents, O-substituted tetraphenyl porphyrins, 3,1-meso tetrakis (o-propionamido phenyl) porphyrin, verdins, purpurins, tin and zinc derivatives of octaethylpurpurin, etiopurpurin, hydroporphyrins, bacteriochlorins of the tetra(hydroxyphenyl) porphyrin series, chlorins, chlorin $e_6$, mono-1-aspartyl derivative of chlorin $e_6$, di-1-aspartyl derivative of chlorin $e_6$, tin(IV) chlorin $e_6$, meta-tetrahydroxyphenylchlorin, benzoporphyrin derivatives, benzoporphyrin monoacid derivatives, tetracyanoethylene adducts of benzoporphyrin, dimethyl acetylenedicarboxylate adducts of benzoporphyrin, Diels-Adler adducts, monoacid ring "a" derivative of benzoporphyrin, sulfonated aluminum PC, sulfonated AlPc, disulfonated, tetrasulfonated derivative, sulfonated aluminum naphthalocyanines, naphthalocyanines with or without metal substituents and with or without varying substituents, anthracenediones, anthrapyrazoles, aminoanthraquinone, phenoxazine dyes, phenothiazine derivatives, chalcogenapyrylium dyes, cationic selena and tellurapyrylium derivatives, ring-substituted cationic PC, pheophorbide derivative, naturally occurring porphyrins, hematoporphyrin, ALA-induced protoporphyrin IX, endogenous metabolic precursors, 5-aminolevulinic acid benzonaphthoporphyrazines, cationic imminium salts, tetracyclines, lutetium texaphyrin, tin-etio-purpurin, porphycenes, benzophenothiazinium and combinations thereof.

When the immunoconjugates are used for in vivo diagnostic use, the binding molecules can also be made detectable by conjugation to, e.g., magnetic resonance imaging (MRI) contrast agents, such as gadolinium diethylenetriaminepentaacetic acid, to ultrasound contrast agents or to X-ray contrast agents, or by radioisotopic labeling.

Furthermore, the binding molecules or immunoconjugates of the invention can also be attached to solid supports, which are particularly useful for immunoassays or purification of the binding partner. Such solid supports might be porous or nonporous, planar or nonplanar and include, but are not limited to, glass, cellulose, polyacrylamide, nylon, polystyrene, polyvinyl chloride or polypropylene supports. The binding molecules can also, for example, usefully be conjugated to filtration media, such as NHS-activated Sepharose or CNBr-activated Sepharose for purposes of immunoaffinity chromatography. They can also usefully be attached to paramagnetic microspheres, typically by biotin-streptavidin interaction. The microspheres can be used for isolation of cells that express or display the human C-type lectin or fragments thereof. As another example, the binding molecules of the invention can usefully be attached to the surface of a microtiter plate for ELISA.

Another aspect of the invention concerns nucleic acid molecules as defined herein encoding binding molecules of the invention. In yet another aspect, provided is nucleic acid molecules encoding at least the binding molecules specifically binding to the human C-type lectin. In a preferred embodiment, the nucleic acid molecules are isolated or purified.

Functional variants of the nucleic acid molecules of the invention are also intended to be a part of the invention. Functional variants are nucleic acid sequences that can be directly translated, using the standard genetic code, to provide an amino acid sequence identical to that translated from the parent nucleic acid molecules. Preferably, the nucleic acid molecules encode binding molecules comprising a CDR3 region, preferably a heavy chain CDR3 region, comprising an amino acid sequence selected from the group consisting of SEQ ID NO:3, SEQ ID NO:4 and SEQ ID NO:5. Even more preferably, the nucleic acid molecules encode binding molecules comprising a heavy chain comprising an amino acid sequence selected from the group consisting of SEQ ID NO:7, SEQ ID NO:9 and SEQ ID NO:11. In yet another embodiment, the nucleic acid molecules encode binding molecules comprising a heavy chain comprising the amino acid sequence of SEQ ID NO:7 and a light chain comprising the amino acid sequence of SEQ ID NO:13, or they encode a heavy chain comprising the amino acid sequence of SEQ ID NO:9 and a light chain comprising the amino acid sequence of SEQ ID NO:13, or they encode a heavy chain comprising the amino acid sequence of SEQ ID NO:11 and a light chain comprising the amino acid sequence of SEQ ID NO:13. In a specific embodiment of the invention the nucleic acid molecules encoding the binding molecules of the invention comprise a nucleotide sequence selected from the group consisting of SEQ ID NO:6, SEQ ID NO:8 and SEQ ID NO:10. In yet another specific embodiment of the invention, the nucleic acid molecules encoding the binding molecules of the invention comprise the nucleotide sequence of SEQ ID NO:6 and SEQ ID NO:12, the nucleotide sequence of SEQ ID NO:8 and SEQ ID NO:12 or the nucleotide sequence of SEQ ID NO:10 and SEQ ID NO:12.

It is another aspect of the invention to provide vectors, i.e., nucleic acid constructs, comprising one or more nucleic acid molecules according to the invention. Vectors can be derived from plasmids such as inter alia F, R1, RP1, Col, pBR322, TOL, Ti, etc; cosmids; phages such as lambda, lambdoid, M13, Mu, P1, P22, Qβ, T-even, T-odd, T2, T4, T7, etc; plant viruses such as inter alia alfalfa mosaic virus, bromovirus, capillovirus, carlavirus, carmovirus, caulivirus, closterovirus, comovirus, cryptovirus, cucumovirus, dianthovirus, fabavirus, fijivirus, furovirus, geminivirus, hordeivirus, ilarvirus, luteovirus, machlovirus, marafivirus, necrovirus, nepovirus, phytorepvirus, plant rhabdovirus, potexvirus, potyvirus, sobemovirus, tenuivirus, tobamovirus, tobravirus, tomato spotted wilt virus, tombusvirus, tymovirus, etc.; or animal viruses such as inter alia adenovirus, arenaviridae, baculoviridae, birnaviridae, bunyaviridae, calciviridae, cardioviruses, coronaviridae, corticoviridae, cystoviridae, Epstein-Barr virus, enteroviruses, filoviridae, flaviviridae, Foot-and-Mouth disease virus, hepadnaviridae, hepatitis viruses, herpesviridae, immunodeficiency viruses, influenza virus, inoviridae, iridoviridae, orthomyxoviridae, papovaviruses, paramyxoviridae, parvoviridae, picornaviridae, poliovirus, polydnaviridae, poxyiridae, reoviridae, retroviruses, rhabdoviridae, rhinoviruses, Semliki Forest virus, tetraviridae, togaviridae, toroviridae, vaccinia virus, vescular stomatitis virus, etc. Vectors can be used for cloning and/or for expression of the binding molecules of the invention and might even be used for gene therapy purposes. Vectors comprising one or more nucleic acid molecules according to the invention operably linked to one or more expression-regulating nucleic acid molecules are also covered by the invention. The choice of the vector is dependent on the recombinant procedures followed and the host used. Introduction of vectors in host cells can be effected by inter alia calcium phosphate transfection, virus infection, DEAE-dextran-mediated transfection, lipofectamin transfection or electroporation. Vectors may be autonomously replicating or may replicate together with the chromosome into which they have been integrated. Preferably, the vectors contain one or more selection markers. The choice of the markers may depend on the host cells of choice, although this is not critical to the invention as is well known to persons skilled in the art. They include, but are not limited to, kanamycin, neomycin, puromycin, hygromycin, zeocin, thymidine kinase gene from Herpes simplex virus (HSV-TK), dihydrofolate reductase gene from mouse (dhfr). Vectors comprising one or more nucleic acid molecules encoding the binding molecules as described above operably linked to one or more nucleic acid molecules encoding proteins or peptides that can be used to isolate the binding molecules are also covered by the invention. These proteins or peptides include, but are not limited to, glutathione-S-transferase, maltose binding protein, metal-binding polyhistidine, green fluorescent protein, luciferase and beta-galactosidase.

Hosts containing one or more copies of the vectors mentioned above are an additional subject of the invention. Preferably, the hosts are host cells. Host cells include, but are not limited to, cells of mammalian, plant, insect, fungal or bacterial origin. Bacterial cells include, but are not limited to, cells from Gram-positive bacteria such as several species of the genera *Bacillus, Streptomyces* and *Staphylococcus* or cells of Gram-negative bacteria such as several species of the genera *Escherichia* and *Pseudomonas*. In the group of fungal cells preferably yeast cells are used. Expression in yeast can be achieved by using yeast strains such as inter alia *Pichia pastoris, Saccharomyces cerevisiae* and *Hansenula polymorpha*. Furthermore, insect cells such as cells from *Drosophila* and Sf9 can be used as host cells. Besides that, the host cells can be plant cells such as inter alia cells from crop plants such as forestry plants, or cells from plants providing food and raw materials such as cereal plants, or medicinal plants, or cells from ornamentals, or cells from flower bulb crops. Transformed (transgenic) plants or plant cells are produced by known methods, for example, *Agrobacterium*-mediated gene transfer, transformation of leaf discs, protoplast transformation by polyethylene glycol-induced DNA transfer, electroporation, sonication, microinjection or ballistic gene transfer. Additionally, a suitable expression system can be a baculovirus system. Expression systems using mammalian cells such as Chinese Hamster Ovary (CHO) cells, COS cells, BHK cells or Bowes melanoma cells are preferred in the invention. Mammalian cells provide expressed proteins with posttranslational modifications that are most similar to natural molecules of mammalian origin. Since the invention deals with molecules that may have to be administered to humans, a completely human expression system would be particularly preferred. Therefore, even more preferably, the host cells are human cells. Examples of human cells are inter alia HeLa, 911, AT1080, A549, 293 and HEK293T cells. In preferred embodiments, the human producer cells comprise at least a functional part of a nucleic acid sequence encoding an adenovirus E1 region in expressible format. In even more preferred embodiments, the host cells are human retina cells and immortalized with nucleic acids comprising adenoviral E1 sequences such as 911 cells or the cell line deposited at the European Collection of Cell Cultures (ECACC), CAMR, Salisbury, Wiltshire SP4 OJG, Great Britain on 29 Feb. 1996 under number 96022940 and marketed under the trademark PER.C6® (PER.C6 is a registered trademark of Crucell Holland B. V.). For the purposes of this application "PER.C6" refers to cells deposited under number 96022940 or ancestors, passages up-stream or downstream as well as descendants from ancestors of deposited cells, as well as derivatives of any one of the foregoing.

Production of recombinant proteins in host cells can be performed according to methods well known in the art. The use of the cells marketed under the trademark PER.C6® as a production platform for proteins of interest has been described in WO 00/63403 the disclosure of which is incorporated herein by reference in its entirety.

Also provided are methods of producing binding molecules or functional variants thereof, preferably human binding molecules or functional variants thereof according to the invention. Such a method comprises a) culturing a host as described above under conditions conducive to the expression of the binding molecules, and b) optionally, recovering the expressed binding molecules. The expressed binding molecules can be recovered from the cell free extract, but preferably they are recovered from the culture medium. Methods to recover proteins, such as binding molecules, from cell free extracts or culture medium are well known to the man skilled in the art. Binding molecules as obtainable by the above-described method are also a part hereof.

Alternatively, next to the expression in hosts, such as host cells, the binding molecules of the invention can be produced synthetically by conventional peptide synthesizers or in cell-free translation systems using RNAs derived from DNA molecules according to the invention. Binding molecule as obtainable by the above described synthetic production methods or cell-free translation systems are also a part of the invention.

In addition, the above-mentioned methods of producing binding molecules can also be used to produce the human C-type lectins of the invention.

In yet another alternative embodiment, binding molecules according to the invention, preferably human binding molecules specifically binding to the human C-type lectins of the invention or fragments thereof, may be generated by transgenic non-human mammals, such as for instance transgenic mice or rabbits, that express human immunoglobulin genes. Preferably, the transgenic non-human mammals have a genome comprising a human heavy chain transgene and a human light chain transgene encoding all or a portion of the human binding molecules as described above. The transgenic non-human mammals can be immunized with a purified or enriched preparation of the human C-type lectins of the invention or fragments thereof and/or cells expressing the human C-type lectins of the invention. Protocols for immunizing non-human mammals are well established in the art. See *Using Antibodies: A Laboratory Manual*, edited by E. Harlow, D. Lane (1998), Cold Spring Harbor Laboratory, Cold Spring Harbor, N.Y., and *Current Protocols in Immunology*, edited by J. E. Coligan, A. M. Kruisbeek, D. H. Margulies, E. M. Shevach, W. Strober (2001), John Wiley & Sons Inc., New York, the disclosures of which are incorporated herein by reference. Immunization protocols often include multiple immunizations, either with or without adjuvants such as Freund's complete adjuvant and Freund's incomplete adjuvant, but may also include naked DNA immunizations. In another embodiment, the human binding molecules are produced by B-cells or plasma cells derived from the transgenic animals. In yet another embodiment, the human binding molecules are produced by hybridomas which are prepared by fusion of B-cells obtained from the above described transgenic non-human mammals to immortalized cells. B-cells, plasma cells and hybridomas as obtainable from the above described transgenic non-human mammals and human binding molecules as obtainable from the above described transgenic non-human mammals, B-cells, plasma cells and hybridomas are also a part of the invention. In yet another embodiment, human binding molecules of the invention can also be produced in transgenic, non-human, mammals such as inter alia rabbits, goats or cows, and secreted into for instance the milk thereof.

Also provided are methods of identifying binding molecules, preferably human binding molecules, e.g., human monoclonal antibodies or fragments thereof, according to the invention or nucleic acid molecules according to the invention and comprises the steps of a) contacting a phage library of binding molecules, preferably human binding molecules, with material comprising the human C-type lectins of the invention or a part thereof, b) selecting at least once for a phage binding to the material comprising the human C-type lectins of the invention or a part thereof, and c) separating and recovering the phage binding to the material comprising the human C-type lectins of the invention or a part thereof. The selection step may be performed in the presence of at least part of the human C-type lectins of the invention, e.g., cells transfected with the human C-type lectin expression plasmids, isolated human C-type lectin, the extracellular part thereof, fusion proteins comprising such, and the like. Phage display methods for identifying and obtaining binding molecules, e.g., antibodies, are by now well-established methods known by the person skilled in the art. They are, e.g., described in U.S. Pat. No. 5,696,108; Burton and Barbas, 1994; and de Kruif et al., 1995b. For the construction of phage display libraries, collections of human monoclonal antibody heavy and light chain variable region genes are expressed on the surface of bacteriophage, preferably filamentous bacteriophage, particles in, for example, single chain Fv (scFv) or in Fab format (see, de Kruif et al., 1995b). Large libraries of antibody fragment-expressing phages typically contain more than $1.0*10^9$ antibody specificities and may be assembled from the immunoglobulin V regions expressed in the B-lymphocytes of immunized- or non-immunized individuals. Alternatively, phage display libraries may be constructed from immunoglobulin variable regions that have been partially assembled in vitro to introduce additional antibody diversity in the library (semi-synthetic libraries). For example, in vitro assembled variable regions contain stretches of synthetically produced, randomized or partially randomized DNA in those regions of the molecules that are important for antibody specificity, e.g., CDR regions. Antigen specific phage antibodies can be selected from the library by immobilizing target antigens such as the human C-type lectins of the invention or fragments thereof on a solid phase and subsequently exposing the target antigens to a phage library to allow binding of phages expressing antibody fragments specific for the solid phase-bound antigen. Non-bound phages are removed by washing and bound phages eluted from the solid phase for infection of Escherichia coli (E. coli) bacteria and subsequent propagation. Multiple rounds of selection and propagation are usually required to sufficiently enrich for phages binding specifically to the target antigen. Phages may also be selected for binding to complex antigens such as complex mixtures of proteins or whole cells such as cells transfected with the human C-type lectin expression plasmids or cells naturally expressing the human C-type lectin of the invention. Selection of antibodies on whole cells has the advantage that target antigens are presented in their native configuration, i.e., unperturbed by possible conformational changes that might have been introduced in the case where an antigen is immobilized to a solid phase. Antigen specific phage antibodies can be selected from the library by incubating a cell population of interest, expressing known and unknown antigens on their surface, with the phage antibody library to let, for example, the scFv or Fab part of the phage bind to the antigens on the cell surface. After incubation and several washes to remove unbound and loosely attached phages, the cells of interest are stained with specific fluorescent labeled antibodies and separated on a Fluorescent Activated Cell Sorter (FACS). Phages that have bound with their scFv or Fab part to these cells are eluted and used to infect Escherichia coli to allow amplification of the new specificity. Generally, one or more selection rounds are required to separate the phages of interest from the large excess of non-binding phages. Monoclonal phage preparations can be analyzed for their specific staining patterns and allowing identification of the antigen being recognized (De Kruif et al., 1995a). The phage display method can be extended and improved by subtracting non-relevant binders during screening by addition of an excess of non-target molecules that are similar, but not identical, to the target, and thereby strongly enhance the chance of finding relevant binding molecules (This process is referred to as the Mabstract® process. Mabstract® is a registered trademark of Crucell Holland B. V., see also U.S. Pat. No. 6,265,150 incorporated herein by reference).

In yet a further aspect, provided is a method of obtaining a binding molecule, preferably a human binding molecule or a nucleic acid molecule according to the invention, wherein the method comprises the steps of a) performing the above described method of identifying binding molecules, preferably human binding molecules such as human monoclonal antibodies or fragments thereof according to the invention, or nucleic acid molecules according to the invention, and b) isolating from the recovered phage the human binding molecule and/or the nucleic acid encoding the human binding molecule. Once a new monoclonal phage antibody has been established or identified with the above mentioned method of identifying binding molecules or nucleic acid molecules encoding the binding molecules, the DNA encoding the scFv or Fab can be isolated from the bacteria or phages and combined with standard molecular biological techniques to make constructs encoding bivalent scFvs or complete human immunoglobulins of a desired specificity (e.g., IgG, IgA or IgM). These constructs can be transfected into suitable cell lines and complete human monoclonal antibodies can be produced (see, Huls et al., 1999; Boel et al., 2000).

In a further aspect, provided are compositions comprising at least one binding molecule, at least one functional variant or fragment thereof, at least one immunoconjugate according to the invention or a combination thereof. In another aspect, also provided are compositions comprising the new human C-type lectin of the invention. In addition to that, the compositions may comprise inter alia stabilizing molecules, such as albumin or polyethylene glycol, or salts. Preferably, the salts used are salts that retain the desired biological activity of the binding molecules and do not impart any undesired toxicological effects. Examples of such salts include, but are not limited to, acid addition salts and base addition salts. Acid addition salts include, but are not limited to, those derived from nontoxic inorganic acids, such as hydrochloric, nitric, phosphoric, sulfuric, hydrobromic, hydroiodic, phosphorous and the like, as well as from nontoxic organic acids such as aliphatic mono- and dicarboxylic acids, phenyl-substituted alkanoic acids, hydroxy alkanoic acids, aromatic acids, aliphatic and aromatic sulfonic acids and the like. Base addition salts include, but are not limited to, those derived from alkaline earth metals, such as sodium, potassium, magnesium, calcium and the like, as well as from nontoxic organic amines, such as N,N'-dibenzylethylenediamine, N-methylglucamine, chloroprocaine, choline, diethanolamine, ethylenediamine, procaine and the like. If necessary, the binding molecules of the invention may be coated in or on a material to protect them from the action of acids or other natural or non-natural conditions that may inactivate the binding molecules.

In yet a further aspect, provided are compositions comprising at least one nucleic acid molecule as defined in the invention. The compositions may comprise aqueous solutions such as aqueous solutions containing salts (e.g., NaCl or salts as described above), detergents (e.g., SDS) and/or other suitable components.

Furthermore, the invention pertains to pharmaceutical compositions comprising at least one binding molecule according to the invention, at least one functional variant or fragment thereof, at least one immunoconjugate according to the invention, at least one composition according to the invention, or combinations thereof. The invention also provides a pharmaceutical composition comprising the human C-type lectin of the invention. The pharmaceutical composition of the invention further comprises at least one pharmaceutically acceptable excipient. A pharmaceutical composition according to the invention can further comprise at least one other therapeutic, prophylactic and/or diagnostic agent.

Typically, pharmaceutical compositions must be sterile and stable under the conditions of manufacture and storage. The binding molecules, variant or fragments thereof, immunoconjugates, nucleic acid molecules or compositions of the invention can be in powder form for reconstitution in the appropriate pharmaceutically acceptable excipient before or at the time of delivery. In the case of sterile powders for the preparation of sterile injectable solutions, the preferred methods of preparation are vacuum drying and freeze-drying (lyophilization) that yield a powder of the active ingredient plus any additional desired ingredient from a previously sterile-filtered solution thereof.

Alternatively, the binding molecules, variant or fragments thereof, immunoconjugates, nucleic acid molecules or compositions of the invention can be in solution and the appropriate pharmaceutically acceptable excipient can be added and/or mixed before or at the time of delivery to provide a unit dosage injectable form. Preferably, the pharmaceutically acceptable excipient used in the invention is suitable to high drug concentration, can maintain proper fluidity and, if necessary, can delay absorption.

The choice of the optimal route of administration of the pharmaceutical compositions will be influenced by several factors including the physico-chemical properties of the active molecules within the compositions, the urgency of the clinical situation and the relationship of the plasma concentrations of the active molecules to the desired therapeutic effect. For instance, if necessary, the binding molecules of the invention can be prepared with carriers that will protect them against rapid release, such as a controlled release formulation, including implants, transdermal patches, and microencapsulated delivery systems. Biodegradable, biocompatible polymers can inter alia be used, such as ethylene vinyl acetate, polyanhydrides, polyglycolic acid, collagen, polyorthoesters, and polylactic acid. Furthermore, it may be necessary to coat the binding molecules with, or co-administer the binding molecules with, a material or compound that prevents the inactivation of the binding molecules. For example, the binding molecules may be administered to a subject in an appropriate carrier, for example, liposomes, or a diluent.

The routes of administration can be divided into two main categories, oral and parenteral administration. The preferred administration route is intravenous.

Oral dosage forms can be formulated inter alia as tablets, troches, lozenges, aqueous or oily suspensions, dispersable powders or granules, emulsions, hard capsules, soft gelatin capsules, syrups or elixirs, pills, dragees, liquids, gels, or slurries. These formulations can contain pharmaceutically excipients including, but not limited to, inert diluents such as calcium carbonate, sodium carbonate, lactose, calcium phosphate or sodium phosphate; granulating and disintegrating agents such as corn starch or alginic acid; binding agents such as starch, gelatin or acacia; lubricating agents such as calcium stearate, glyceryl behenate, hydrogenated vegetable oils, magnesium stearate, mineral oil, polyethylene glycol, sodium stearyl, fumarate, stearic acid, talc, zinc stearate; preservatives such as n-propyl-p-hydroxybenzoate; coloring, flavoring or sweetening agents such as sucrose, saccharine, glycerol, propylene glycol or sorbitol; vegetable oils such as arachis oil, olive oil, sesame oil or coconut oil; mineral oils such as liquid paraffin; wetting agents such as benzalkonium chloride, docusate sodium, lecithin, poloxamer, sodium lauryl sulfate, sorbitan esters; and thickening agents such as agar, alginic acid, beeswax, carboxymethyl cellulose calcium, carageenan, dextrin or gelatin.

The pharmaceutical compositions can also be formulated for parenteral administration. Formulations for parenteral administration can be inter alia in the form of aqueous or non-aqueous isotonic sterile non-toxic injection or infusion solutions or suspensions. Preferred parenteral administration routes include intravenous, intraperitoneal, epidural, intramuscular and intratumoral injection, or infusion. The solutions or suspensions may comprise agents that are non-toxic to recipients at the dosages and concentrations employed such as 1,3-butanediol, Ringer's solution, Hank's solution, isotonic sodium chloride solution, oils, e.g., synthetic mono- or diglycerides or fatty acids, e.g., oleic acid, local anesthetic agents, preservatives, buffers, viscosity or solubility increasing agents, water-soluble antioxidants, e.g., ascorbic acid, cysteine hydrochloride, sodium bisulfate, sodium metabisulfite, sodium sulfite and the like, oil-soluble antioxidants, e.g., ascorbyl palmitate, butylated hydroxyanisole (BHA), butylated hydroxytoluene (BHT), lecithin, propyl gallate, alpha-tocopherol, and the like, and metal chelating agents, e.g., citric acid, ethylenediamine tetraacetic acid (EDTA), sorbitol, tartaric acid, phosphoric acid, and the like.

The binding molecules, preferably the human binding molecules such as human monoclonal antibodies according to the invention, the variants or fragments thereof, the immunoconjugates according to the invention, the nucleic acid molecules according to the invention, the compositions according to the invention or the pharmaceutical compositions according to the invention can be used as medicaments. They can inter alia be used in the diagnosis, prevention, treatment, or combination thereof, of a neoplastic disorder or disease. The human C-type lectin of the invention or fragments thereof can also be used as medicaments. Preferably, they are used in the diagnosis, treatment, or combination thereof, of a neoplastic disorder or disease. Preferably, the neoplastic disorder or disease is selected from the group consisting of acute myeloid leukemia, chronic myeloid leukemia, chronic myelomonocytic leukemia, acute promyelocytic leukemia, myelodysplastic syndrome, juvenile myelomonocytic leukemia, and Langerhans cell histiocytosis. The binding molecules of the invention are suitable for treatment of yet untreated patients suffering from any of the above disorders and diseases, patients who have been or are treated and are in remission or are not in remission, and patients with a recurrent/refractory diseases or disorders. The binding molecules of the invention may even be used in the prophylaxis of any one of the above mentioned disorders or diseases.

The above-mentioned molecules or compositions may be employed in conjunction with other molecules useful in diagnosis and/or treatment. They can be used in vitro, ex vivo or in vivo. The molecules are typically formulated in the compositions and pharmaceutical compositions of the invention in a therapeutically or diagnostically effective amount. Dosage regimens can be adjusted to provide the optimum desired response (e.g., a therapeutic response). For example, a single bolus may be administered, several divided doses may be administered over time or the dose may be proportionally reduced or increased as indicated by the exigencies of the therapeutic situation. The molecules and compositions according to the invention are preferably sterile. Methods to render these molecules and compositions sterile are well known in the art. The other molecules useful in diagnosis and/or treatment can be administered in a similar dosage regimen as proposed for the binding molecules of the invention. If the other molecules are administered separately, they may be administered to a subject with a neoplastic disorder or disease prior (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks before) to, concomitantly with, or subsequent (e.g., 2 minutes, 5 minutes, 10 minutes, 15 minutes, 30 minutes, 45 minutes, 60 minutes, 2 hours, 4 hours, 6 hours, 8 hours, 10 hours, 12 hours, 14 hours, 16 hours, 18 hours, 20 hours, 22 hours, 24 hours, 2 days, 3 days, 4 days, 5 days, 7 days, 2 weeks, 4 weeks or 6 weeks after) to the administration of one or more of the binding molecules or pharmaceutical compositions of the invention. The dosing regimen is usually sorted out during clinical trials in human patients.

Human binding molecules and pharmaceutical compositions comprising the human binding molecules are particularly useful, and often preferred, when to be administered to human beings as in vivo diagnostic or therapeutic agents, since recipient immune response to the administered antibody will often be substantially less than that occasioned by administration of a monoclonal murine, chimeric or humanized binding molecule.

Alternatively, cells that are genetically engineered to express the binding molecules of the invention are administered to patients in vivo. Such cells may be obtained from an animal or patient or an MHC-compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the nucleic acid molecules of the invention into the cells. Preferably, the binding molecules are secreted from the cells. The engineered cells which express and preferably secrete the binding molecules as described herein can be introduced into the patient, for example, systemically, e.g., in the circulation, or intraperitoneally. In other embodiments, the cells can be incorporated into a matrix or can be encapsulated and implanted in the body. In a gene therapy setting the binding molecules may be administered in the form of a vector capable of infecting cells of the host, coding for a binding molecule according to the invention.

In another aspect, the invention concerns the use of binding molecules, preferably human binding molecules, e.g., human monoclonal antibodies, fragments or variants thereof, immunoconjugates, nucleic acid molecules, compositions or pharmaceutical compositions according to the invention in the preparation of a medicament for the diagnosis, prophylaxis, treatment, or combination thereof, of a neoplastic disorder or disease. The neoplastic disease or disorder may be selected from the group described above.

Kits comprising at least one binding molecule, preferably human binding molecule such as human monoclonal antibody according to the invention, at least one variant or fragment thereof, at least one immunoconjugate according to the invention, at least one nucleic acid molecule according to the invention, at least one composition according to the invention, at least one pharmaceutical composition according to the invention, at least one vector according to the invention, at least one host according to the invention or a combination thereof are also a part of the invention. Optionally, the above-described kits also comprise the human C-type lectin of the invention. Optionally, the above described components of the kits of the invention are packed in suitable containers and labeled for diagnosis and/or treatment of the indicated conditions. The above-mentioned components may be stored in unit or multi-dose containers, for example, sealed ampules, vials, bottles, syringes, and test tubes, as an aqueous, preferably sterile, solution or as a lyophilized, preferably sterile, formulation for reconstitution. The containers may be formed from a variety of materials such as glass or plastic and may have a sterile access port (for example, the container may be an intravenous solution bag or a vial having a stopper pierceable by a hypodermic injection needle). The kit may further comprise more containers comprising a pharmaceutically acceptable buffer, such as phosphate-buffered saline, Ringer's solution and dextrose solution. It may further include other materials desirable from a commercial and user standpoint, including other buffers, diluents, filters, needles, syringes, culture medium for one or more of the suitable hosts. Associated with the kits can be instructions customarily included in commercial packages of therapeutic or diagnostic products, that contain information about, for example, the indications, usage, dosage, manufacture, administration, contraindications and/or warnings concerning the use of such therapeutic or diagnostic products.

In a further aspect, provided are methods of detecting the human C-type lectin of the invention, particularly the human C-type lectin comprising the amino acid sequence as shown in SEQ ID NO:2 or a variant or part thereof, wherein the method comprises the steps of (a) contacting a sample with a diagnostically effective amount of a binding molecule of the invention or a functional variant or fragment thereof, and (b) determining whether the binding molecule or functional variant or fragment thereof specifically binds to a compound of the sample. Methods of detection are known in the art and include, but are not limited to, Western Blot, RIA, ELISA, and immunohistochemical methods.

Furthermore, the invention is directed to a method of screening a binding molecule or a functional variant or fragment thereof for specific binding to the same epitope of a human C-type lectin of the invention, preferably a human C-type lectin comprising the amino acid sequence as shown in SEQ ID NO:2 or fragment thereof, as the epitope bound by the binding molecule according to the invention, wherein the method comprises the steps of (a) contacting a binding molecule (or a functional variant or fragment thereof) to be screened, a binding molecule (or functional fragment or variant thereof) according to the invention and the human C-type lectin comprising the amino acid sequence as shown in SEQ ID NO:2 (or a fragment thereof comprising the antigenic determinant), (b) measure if the binding molecule (or functional variant or fragment thereof) to be screened is capable of competing for specifically binding to the human C-type lectin comprising the amino acid sequence as shown in SEQ ID NO:2 (or fragment thereof comprising the antigenic determinant) with the binding molecule of the invention. In this screening method, “specifically binding to the same epitope” also contemplates specific binding to substantially or essentially the same epitope as the epitope bound by the binding molecules of the invention. The capacity to block, or compete with, the binding of the binding molecules of the invention to the human C-type lectin typically indicates that a binding molecule to be screened binds to an epitope or binding site on the human C-type lectin that structurally overlaps with the binding site on the human C-type lectin that is immunospecifically recognized by the binding molecules of the invention. Alternatively, this can indicate that a binding molecule to be screened binds to an epitope or binding site which is sufficiently proximal to the binding site immunospecifically recognized by the binding molecules of the invention to sterically or otherwise inhibit binding of the binding molecules of the invention to the human C-type lectin.

In general, competitive inhibition is measured by means of an assay, wherein an antigen composition, i.e., a composition comprising a human C-type lectin of the invention, is admixed with reference binding molecules, i.e., the binding molecules of the invention, and binding molecules to be screened. Usually, the binding molecules to be screened are present in excess. Protocols based upon ELISAs and Western blotting are suitable for use in such simple competition studies. In certain embodiments, one may pre-mix the reference binding molecules with varying amounts of the binding molecules to be screened (e.g., 1:10, 1:20, 1:30, 1:40, 1:50, 1:60, 1:70, 1:80, 1:90 or 1:100) for a period of time prior to applying to the antigen composition. In other embodiments, the reference binding molecules and varying amounts of binding molecules to be screened can simply be admixed during exposure to the antigen composition. In any event, by using species or isotype secondary antibodies one will be able to detect only the bound reference binding molecules, the binding of which will be reduced by the presence of a binding molecule to be screened that recognizes substantially the same epitope. In conducting a binding molecule competition study between a reference binding molecule and any binding molecule to be screened (irrespective of species or isotype), one may first label the reference binding molecule with a detectable label, such as, e.g., biotin or an enzymatic (or even radioactive) label to enable subsequent identification. In these cases, one would pre-mix or incubate the labeled reference binding molecules with the binding molecules to be screened at various ratios (e.g., 1:10, 1:20, 1:30, 1:40, 1:50, 1:60, 1:70, 1:80, 1:90 or 1:100) and (optionally after a suitable period of time) then assay the reactivity of the labeled reference binding molecules and compare this with a control value in which no potentially competing binding molecule was included in the incubation. The assay may again be any one of a range of immunological assays based upon antibody hybridization, and the reference binding molecules would be detected by means of detecting their label, e.g., using streptavidin in the case of biotinylated reference binding molecules or by using a chromogenic substrate in connection with an enzymatic label (such as 3,3'5,5'-tetramethylbenzidine (TMB) substrate with peroxidase enzyme) or by simply detecting a radioactive label. A binding molecule to be screened that binds to the same epitope as the reference binding molecule will be able to effectively compete for binding and thus will significantly reduce reference binding molecule binding, as evidenced by a reduction in bound label. The reactivity of the (labeled) reference binding molecule in the absence of a completely irrelevant binding molecule would be the control high value. The control low value would be obtained by incubating the labeled reference binding molecule with unlabelled reference binding molecules of exactly the same type, when competition would occur and reduce binding of the labeled reference binding molecule. In a test assay, a significant reduction in labeled reference binding molecule reactivity in the presence of a binding molecule to be screened is indicative of a binding molecule that recognizes the same epitope, i.e., one that “cross-reacts” with the labeled reference binding molecule.

Binding molecules identified by these competition assays (“competitive binding molecules” or “cross-reactive binding molecules”) include, but are not limited to, antibodies, antibody fragments and other binding agents that bind to an epitope or binding site bound by the reference binding molecule, i.e., a binding molecule of the invention, as well as antibodies, antibody fragments and other binding agents that bind to an epitope or binding site sufficiently proximal to an epitope bound by the reference binding molecule for competitive binding between the binding molecules to be screened and the reference binding molecule to occur. Preferably, competitive binding molecules will, when present in excess, inhibit specific binding of a reference binding molecule to a selected target species by at least 10%, preferably by at least 25%, more preferably by at least 50%, and most preferably by at least 75%-90% or greater. The identification of one or more competitive binding molecules that bind to about, substantially, essentially or at the same epitope as the binding molecules of the invention is a straightforward technical matter. As the identification of competitive binding molecules is determined in comparison to a reference binding molecule, i.e., a binding molecule of the invention, it will be understood that actually determining the epitope to which the reference binding molecule and the competitive binding molecule bind is not in any way required in order to identify a competitive binding molecule that binds to the same or substantially the same epitope as the reference binding molecule.

In yet a further aspect, provided is a method for selecting myeloid cells comprising the steps of (a) contacting a sample comprising myeloid cells with a binding molecule capable of specifically binding to a human C-type lectin of the invention, preferably a human C-type lectin comprising the amino acid sequence as shown in SEQ ID NO:2 or a fragment thereof, (b) separating the cells that bind to the binding molecule from the cells that do not bind to the binding molecule, and (c) recovering the cells which are bound by the binding molecule. Preferably, binding molecules capable of specifically binding to a human C-type lectin comprising the amino acid sequence as shown in SEQ ID NO:2 are binding molecules of the invention or variants or fragments thereof. The step of separating the cells that bind to the binding molecule from the cells that do not bind to the binding molecule can inter alia be performed by affinity separation to provide a substantially pure population of cells. Techniques for affinity separation may include magnetic separation, using binding molecule-coated magnetic beads, affinity chromatography, cytotoxic agents joined to a monoclonal antibody or used in conjunction with a monoclonal antibody, e.g., complement and cytotoxins, and “panning” with binding molecules attached to a solid matrix, e.g., plate, or other convenient technique. Techniques providing accurate separation include fluorescence activated cell sorters, which can have varying degrees of sophistication, such as multiple color channels, low angle and obtuse light scattering detecting channels, impedance channels, etc. The cells may be selected against dead cells by employing dyes associated with dead cells (e.g., propidium iodide). Any technique may be employed which is not unduly detrimental to the viability of the selected cells.

In an embodiment, the binding molecules can be used to target, e.g., myeloid cells, e.g., for labeling such cells. For such use, the binding molecules can be linked to a molecule that can be detected. Thus, provided is methods for localizing myeloid cells ex vivo or in vitro or in vivo. This may be useful for diagnostic or scientific purposes. The detectable label can be, e.g., a radioisotope, a fluorescent compound, an enzyme, or an enzyme co-factor. Alternatively, the labels include magnetic beads, which allow for direct separation. Methods for detecting the presence of myeloid cells in a sample, or measuring the amount of myeloid cells, comprises contacting the sample, and a control sample, with a binding molecule of the invention or variant or fragment thereof. These molecules specifically bind to myeloid cells under conditions that allow for formation of a complex between the binding molecules and myeloid cells. The formation of a complex is then detected, wherein a difference complex formation between the sample compared to the control sample is indicative the presence of myeloid cells in the sample. Methods for detecting the presence or quantifying the amount of myeloid cells in vivo comprise (a) administering to a subject a binding molecule of the invention or a variant or fragment thereof, conjugated to a detectable marker, (b) exposing the subject to a means for detecting the detectable marker to identify areas containing myeloid cells.

Further encompassed are methods for selecting non-myeloid cells comprising (a) contacting a sample comprising myeloid cells with a binding molecule capable of specifically binding to a human C-type lectin of the invention, preferably a human C-type lectin comprising the amino acid sequence as shown in SEQ ID NO:2 or a fragment thereof, (b) separating the cells that bind to the binding molecule from the cells that do not bind to the binding molecule, and (c) recovering the cells which are not bound by the binding molecule. Preferably, binding molecules capable of specifically binding to a human C-type lectin comprising the amino acid sequence as shown in SEQ ID NO:2 are binding molecules of the invention or variants or fragments thereof.

Compositions highly enriched for myeloid cells or non-myeloid cells are achieved in this manner. Preferably, the myeloid cells or non-myeloid cells will be at or about 90% or more of the cell composition, and preferably be at or about 95% or more of the cell composition. The enriched cell composition may be used immediately, or may be frozen at liquid nitrogen temperatures and stored for long periods of time, being thawed and capable of being reused.

The methods of selecting myeloid cells and non-myeloid cells can further comprise the step of contacting the sample comprising the myeloid cells, preferably a sample comprising a heterogeneous cell population with among others myeloid cells, before, concomitant or after contact with a binding molecule capable of specifically binding to a human C-type lectin of the invention, preferably a human C-type lectin comprising the amino acid sequence as shown in SEQ ID NO:2 or a fragment thereof, with at least a second binding molecule, wherein the second binding molecule binds to an antigen other than the human C-type lectin comprising the amino acid sequence as shown in SEQ ID NO:2. The second binding molecule can bind to another antigen on myeloid cells or can bind to an antigen on non-myeloid cells. In a specific embodiment the second binding molecule binds to another antigen on myeloid cells, wherein the antigen is specific for a subset of myeloid cells. This way, a specific subset of myeloid cells can be separated from other subsets. Examples of suitable second binding molecules include, but are definitely not limited to, binding molecules binding CD13, CD14, CD33, CD34, CD36, CD38, CD71, CD117, CD133, MPO and HLA-DR. Preferably, the binding molecules capable of specifically binding to a human C-type lectin comprising the amino acid sequence as shown in SEQ ID NO:2 or a fragment thereof, preferably the binding molecules of the invention, are labeled with a detectable label. More preferably, the second binding molecule is also labeled with a detectable label. Most preferably, the labels of the binding molecules of the invention and the second binding molecules are different. Detectable labels include, but are not limited to, fluorescent molecules and radioisotopes.

In yet another embodiment, the binding molecules of the invention can be used to detect a myeloid neoplastic disorder or disease. In general, neoplastic cells in the blood, bone marrow, other hematopoietic or other non-hematopoietic compartments of the body can be selected based on their specific pattern in for instance FACS analysis. After this selection, the cells can be further selected by means of the binding molecules of the invention. As the binding molecules of the invention bind exclusively to myeloid cells, the selection subdivides neoplastic cells into myeloid neoplastic cells and non-myeloid neoplastic cells.

EXAMPLES

To illustrate the invention, the following examples are provided. These examples are not intended to limit the scope of the invention.

Example 1

Selection of Phages Carrying Single Chain Fv Fragments Specifically Recognizing Human Acute Myeloid Leukemia Cells Antibody fragments were selected using antibody phage display libraries, general phage display technology and Mabstract® technology, essentially as described in U.S. Pat. No. 6,265,150 and in WO 98/15833 (both of which are incorporated by reference herein). Furthermore, the methods and helper phages as described in WO 02/103012 (incorporated by reference herein) were used in the invention. For identifying phage antibodies recognizing AML tumor cells phage selection experiments were performed using the AML tumor cell line HL60 and primary AML tumor cells that were obtained from bone marrow aspirates of AML patients.

An aliquot of a phage library (500 µl, approximately $10^{13}$ cfu, amplified using CT helper phage (see, WO 02/103012)) was blocked and presubtracted by mixing the library with 10 ml of RPMI 1640 medium with 10% FBS containing $230*10^6$ peripheral blood leukocytes (PBL). The obtained mixture was rotated at 4° C. for 1.5 hours. Hereafter, the cells were pelleted and the supernatant containing the phage library was transferred to a new tube containing a fresh pellet of $230*10^6$ PBL. The cells were resuspended in the phage library supernatant and the mixture was again rotated at 4° C. for 1.5 hours. This procedure was repeated once more and eventually 10 ml of supernatant containing the blocked phage library which was three times subtracted with PBL was transferred to a new tube and was kept overnight at 4° C. The next day $4*10^6$ cells of the AML cell line called HL60 were pelleted in a separate 15 ml tube and the cells were resuspended in 1 ml of RPMI 1640 medium with 10% FBS. To the tube 3.3 ml of the presubtracted blocked phage library and 5 ml of RPMI 1640 medium with 10% FBS was added and the mixture was rotated at 4° C. for two hours. Hereafter, the obtained mixture was transferred to a 50 ml tube and washed five times with 30 ml RPMI 1640 medium with 10% FBS. To the pelleted cells 0.8 ml of 50 mM glycine-HCl pH 2.2 was added, mixed well and left at room temperature for ten minutes to elute the attached phages. After that, 0.4 ml of 1 M Tris-HCl pH 7.4 was added for neutralization. Then, the cells were pelleted again and the supernatant was used to infect 5 ml of an XL1-Blue *E. coli* culture that had been grown at 37° C. to an OD600 nm of approximately 0.3. The phages were allowed to infect the XL1-Blue bacteria for 30 minutes at 37° C. Subsequently, the mixture was centrifuged for ten minutes, at 3200*g at room temperature and the bacterial pellet was resuspended in 1 ml 2-trypton yeast extract (2TY) medium. The obtained bacterial suspension was divided over a 2TY agar plate supplemented with tetracyclin, ampicillin and glucose. After incubation overnight of the plates at 37° C., the colonies were scraped from the plates and used to prepare an enriched phage library, essentially as described by de Kruif et al. (1995a) and WO 02/103012. Briefly, scraped bacteria were used to inoculate 2TY medium containing ampicillin, tetracycline and glucose and grown at a temperature of 37° C. to an OD600 nm of ~0.3. CT helper phages were added and allowed to infect the bacteria after which the medium was changed to 2TY containing ampicillin, tetracycline and kanamycin. Incubation was continued overnight at 30° C. The next day, the bacteria were removed from the 2TY medium by centrifugation after which the phages in the medium were precipitated using polyethylene glycol (PEG) 6000/NaCl. Finally, the phages were dissolved in 2 ml of phosphate buffered saline (PBS) with 1% bovine serum albumin (BSA), filter-sterilized and used for the next round of selection. To this purpose, a 500 µl aliquot of the HL-60-derived amplified sublibrary was blocked with 2 ml of RPMI 1640 medium with 10% FBS for 30 minutes at 4° C. To the blocked sublibrary $5 \times 10^6$ thawed primary AML blasts (90% CD33+ CD34+ blasts, FAB type M0) were added that previously had been stained with a PE-labeled anti-CD34 antibody (Becton Dickinson). The obtained mixture rotated at 4° C. for 2.5 hours. Hereafter, the mixture was transferred to a 50 ml tube, washed three times with 30 ml cold RPMI 1640 medium with 10% FBS. Subsequently, the mixture was passed over a 70 micron cell strainer and was subjected to flow cytometry. Cell sorting was performed using a FACSVantage flow cytometer (Becton Dickinson). Cells were gated on the basis of low sideward scatter (SSC) combined with CD34-PE staining. Approximately $9*10^5$ cells were sorted. The sorted cells were spun down, the supernatant was saved and the bound phages were eluted from the cells by resuspending the cells in 800 µl 50 mM glycin-HCl pH 2.2 followed by incubation for five minutes at room temperature. The obtained mixture was neutralized with 400 µl M Tris-HCl pH 7.4 and added to the rescued supernatant. The eluted phages were used to re-infect XL1-Blue *E. coli* cells as described supra. After the second round of selection, individual *E. coli* colonies were used to prepare monoclonal phage antibodies. Essentially, individual colonies were grown to log-phase in 96-well plate format and infected with CT helper phages after which phage antibody production was allowed to proceed overnight. The produced phage antibodies were PEG/NaCl-precipitated and filter-sterilized and tested using flow cytometry (FACSCalibur, Becton Dickinson) for binding to both the HL-60 AML cell line as well as to the primary AML blasts (that were used for the second round selection). From the selection a large panel of phage antibodies was obtained that demonstrated binding to HL-60 AML cells and AML blasts as well as to various subsets of peripheral blood leukocytes. One of the selected phage antibodies, called SC02-357, bound particularly well to both the primary AML tumor blasts as well as to HL-60 AML cells and was analyzed in further detail (see, examples below).

Example 2

Characterization of scFv SC02-357 and Related scFvs

Plasmid DNA was obtained from the selected scFv clone SC02-357 according to standard techniques known in the art. Thereafter, the nucleotide sequence of scFv clone SC02-357 was determined according to standard techniques well known to a person skilled in the art. Alignment analysis in a database of previously selected phage antibodies recognizing unknown targets revealed two other scFvs, called SC02-378 and SC02-161, sharing high homology in both heavy chain framework as well as CDR3 regions and sharing an identical light chain, indicating that these phage antibodies most likely recognized the same target antigen.

The nucleotide sequences of the scFvs called SC02-357, SC02-378 and SC02-161 are listed in Table 1 and have the SEQ ID NOS:14, 16 and 18, respectively. The amino acid translation of the nucleotide sequences of the scFvs SC02-357, SC02-378 and SC02-161 are also listed in Table 1 and have the SEQ ID NOS:15, 17 and 19, respectively. The VH and VL gene identity and amino acid sequence of the heavy chain CDR3 regions (see, SEQ ID NOS:3, 4 and 5, respectively) of the scFvs called SC02-357, SC02-378 and SC02-161 are also depicted in Table 1.

Example 3

Expression of the Antigen Recognized By SC02-357 on Primary AML Samples, Tumor Cell Lines and Normal Hematopoetic Cells The distribution of the target antigen recognized by the SC02-357 phage antibody was analyzed by flow cytometry using primary AML samples, tumor cell lines and normal hematopoetic cells derived from bone marrow and peripheral blood. For flow cytometry analysis, phage antibodies were first blocked in an equal volume of PBS, 4% milk protein (MPBS) for 15 minutes at 4° C. prior to the staining of the various cells. The binding of the phage antibodies to the cells was visualized using a biotinylated anti-M13 antibody (Santa Cruz Biotechnology) followed by addition of streptavidin-allophycocyanin or streptavidin-phycoerythrin (Caltag).

Analysis of a set of four different primary AML blasts (FAB subtypes: AML7, FAB-M4; AML9, FAB-M1; AML10, FAB-M2; AML11, FAB-M0) showed strong binding of the SC02-357 phage antibody to all AML patient samples as compared to a control phage antibody (see, FIG. 1).

Analysis of a panel of tumor cell lines of both hematopoetic and non-hematopoetic origin revealed that expression of the antigen recognized by SC02-357 was restricted to a subset of tumor cell lines of myeloid origin: HL-60, THP-1 and U937 (see, Table 2).

Figure 2:
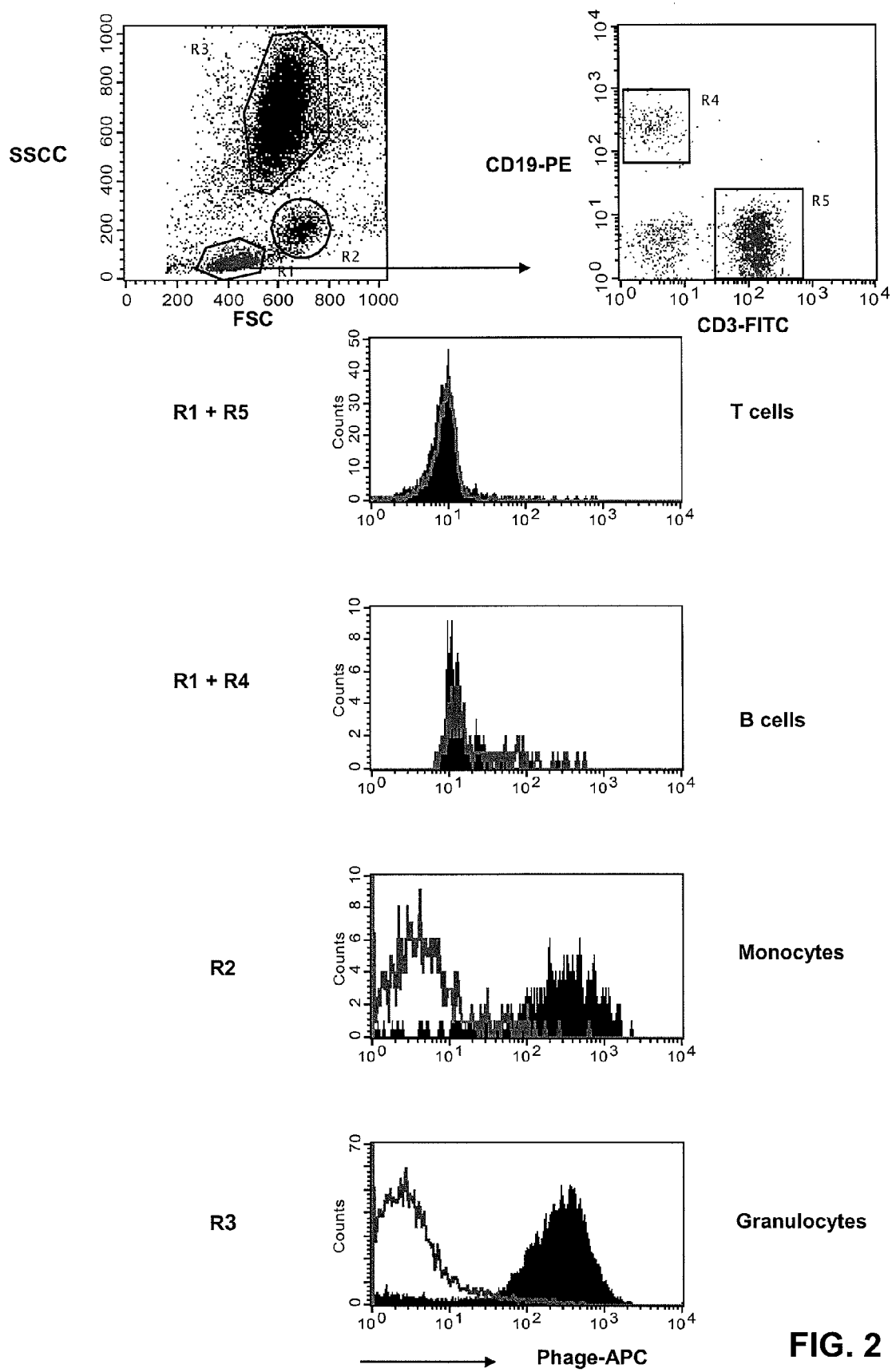
FIG. 2: Binding of the SC02-357 phage antibody to subpopulations of peripheral blood leukocytes.

Within peripheral blood leukocytes the SC02-357 phage antibody specifically recognized granulocytes and monocytes (FIG. 2). Flow cytometric analysis was performed by gating the lymphocyte-, monocyte- and granulocyte subpopulations on the basis of their forward- and side-scatter characteristics. The lymphocytes were further divided in B-cells and T-cells by staining the sample with a PE-conjugated anti-CD19 antibody (Becton Dickinson) and a FITC-conjugated anti-CD3 antibody (Pharmingen).

Figure 3A:
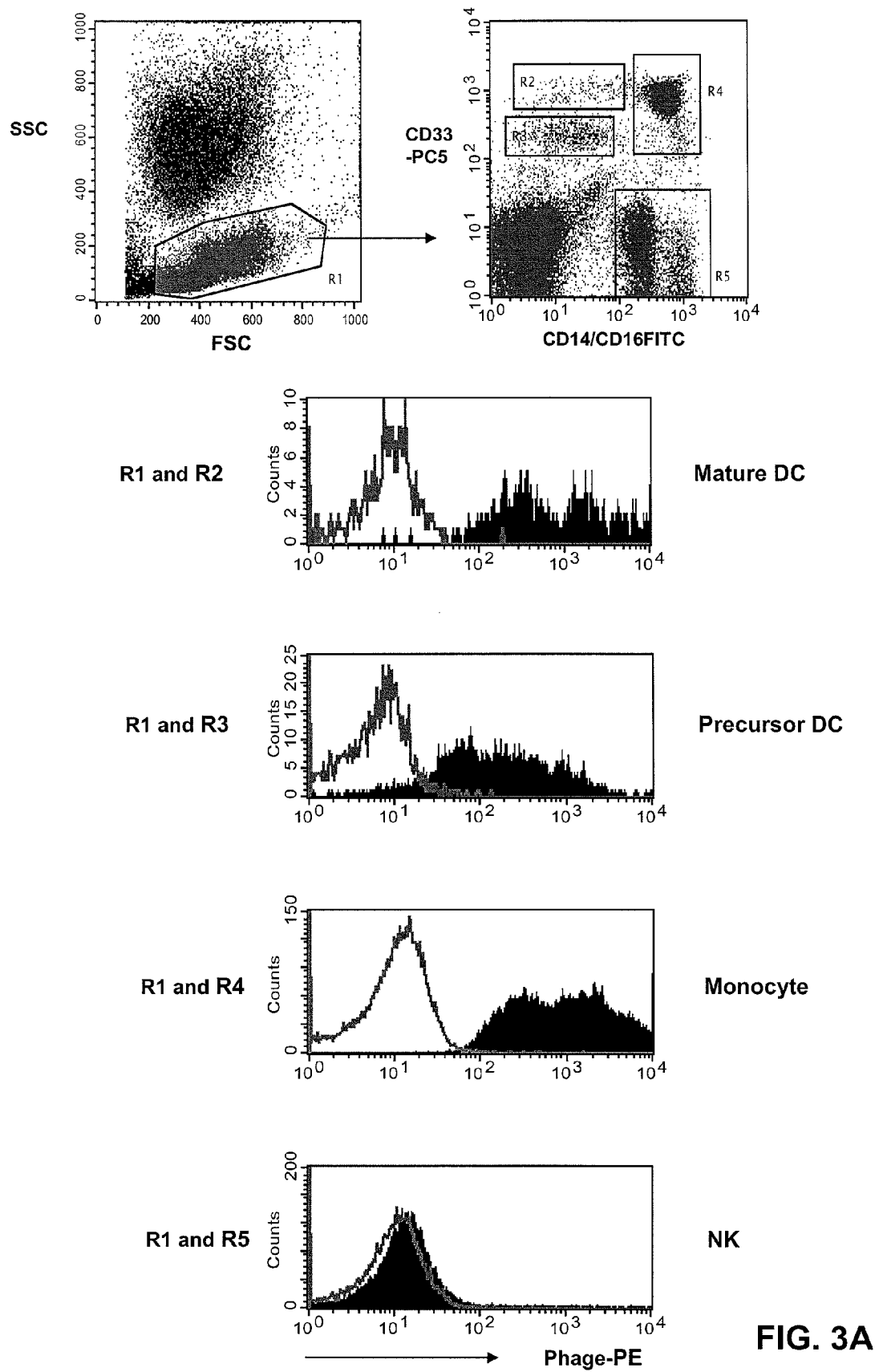
FIG. 3: Binding of the SC02-357 phage antibody to subpopulations of peripheral blood (FIG. 3A). Binding of the SC02-357 phage antibody to subsets of dendritic cells within peripheral blood (FIG. 3B).

Within peripheral blood, subsets of dendritic cells were analyzed by staining with antibodies recognizing the cell surface antigens CD14 (FITC-labeled, Becton Dickinson), CD16 (FITC-labeled, Pharmingen) and CD33 (PC5-labeled, Immunotech) (FIG. 3A). Accordingly, a more mature dendritic cell population can be distinguished as a CD33brightCD14$^-$CD16$^-$ population, while a precursor dendritic cell population can be seen as a CD33dimCD14$^-$CD16$^-$ population. As shown in FIG. 3A SC02-357 stains both the mature and the precursor dendritic cell subsets within peripheral blood. In contrast, the CD16$^+$ NK cells are clearly negative for the antigen recognized by the phage antibody SC02-357.

Figure 3B:
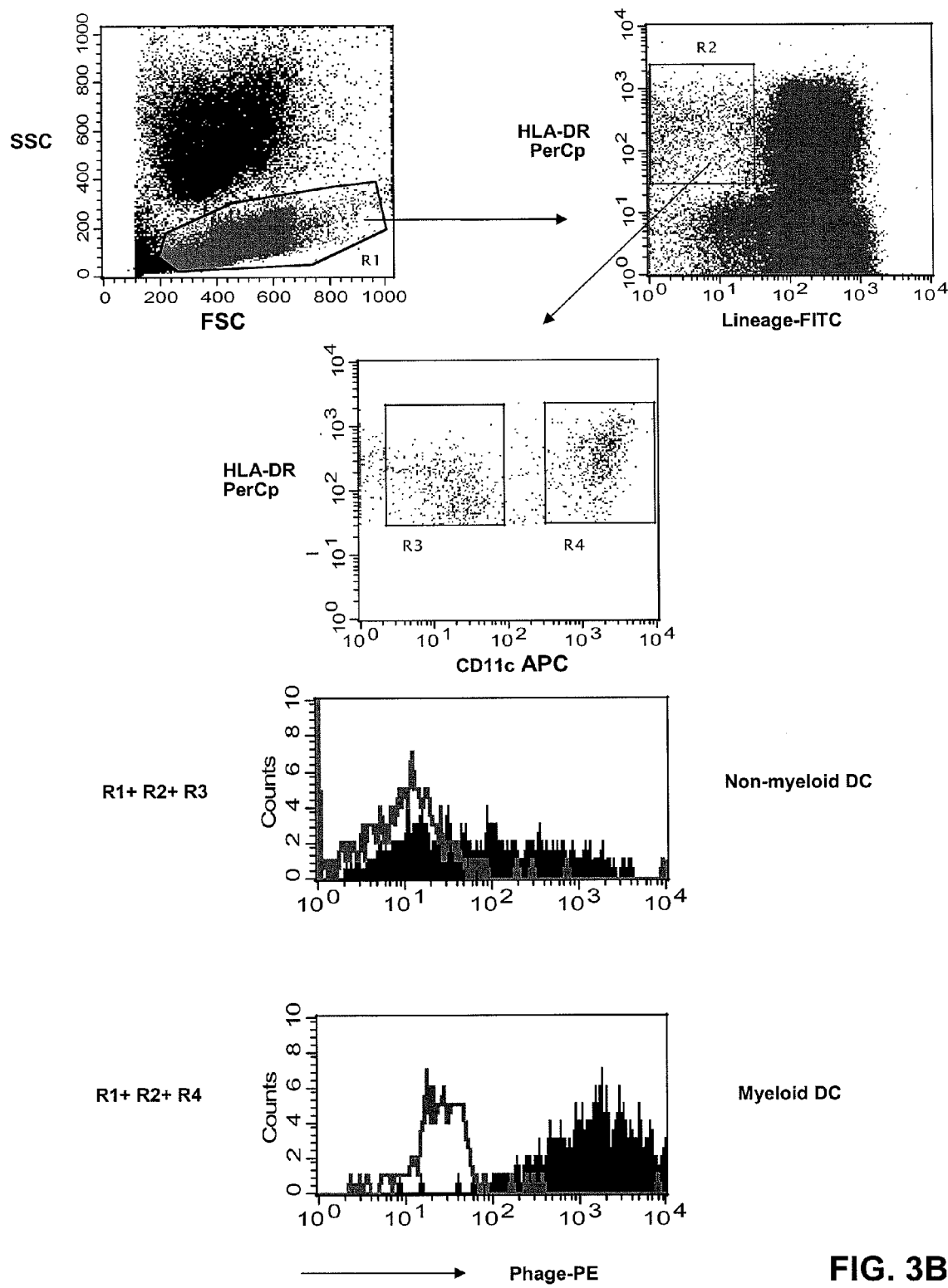

Alternatively, dendritic cell subsets can be distinguished based on the presence of the CD11c antigen. In this type of analysis dendritic cells are gated as a HLA-DR$^+$ (PerCP, Becton Dickinson), lineage marker-negative (lin-FITC, Becton Dickinson) population (FIG. 3B), which can subsequently be subdivided in CD11c$^-$ non-myeloid dendritic cells and CD11c$^+$ myeloid dendritic cells (anti-CD11c-allophycocyanin, Becton Dickinson). SC02-357 strongly stained the CD11c$^+$ myeloid dendritic cells, while it did not exclusively stain the fraction of the CD11c$^-$ non-myeloid dendritic cells (phage antibody binding was visualized in this case using streptavidin-PE (Caltag)).

Analysis further indicated that erythrocytes and platelets were not stained by the phage antibody SC02-357 (data not shown).

Figure 4:
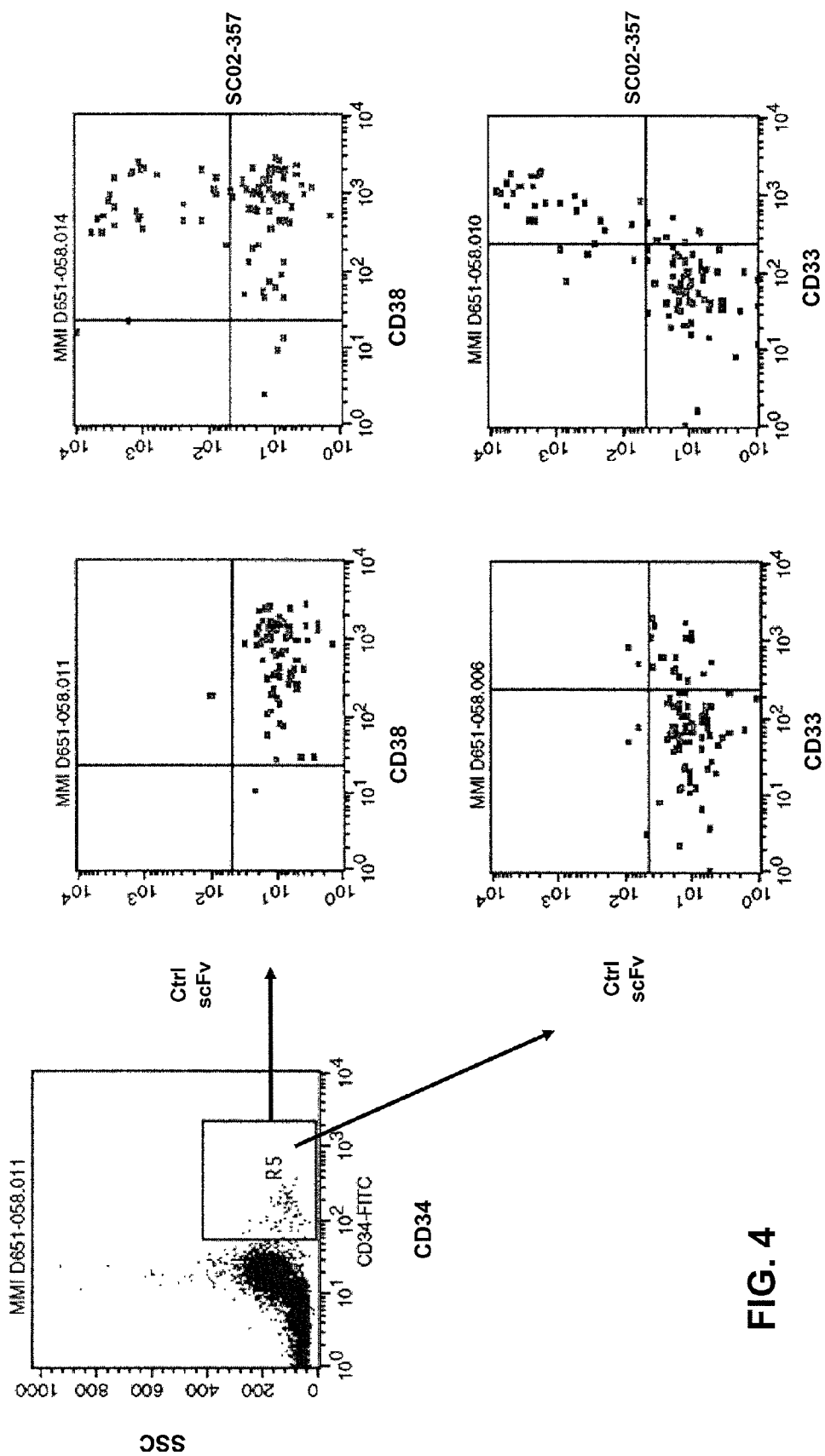
FIG. 4: Binding of the SC02-357 phage antibody to CD34$^+$ cells within normal bone marrow.

Within normal bone marrow, lymphoid and myeloid subpopulations were segregated on the basis of side scatter properties and CD33 staining (anti-CD33, PE-conjugated, Pharmingen). Granulocyte precursors (CD33dim, SSChigh) as well as monocyte precursors (CD33high, SSCdim) were stained by SC02-357, thus mirroring the staining profile in peripheral blood. CD34-expressing progenitor cells were tested for SC02-357 reactivity by initially gating the CD34$^+$ cells and subsequently co-analyzing phage antibody staining and CD38 (anti-CD38, PE-conjugated Becton Dickinson) or CD33 (anti-CD33, PE-conjugated, Pharmingen) reactivity. FIG. 4 shows that only a fraction of the CD34$^+$ cells displayed reactivity with SC02-357. More specifically, the SC02-357 reactive CD34$^+$ cells strongly co-expressed both CD38 and CD33. This indicated expression of the antigen recognized by SC02-357 is present on CD34$^+$ progenitor cells that have differentiated towards the myeloid lineage, while the uncommitted CD34$^+$ progenitor cells lack the antigen.

From these combined expression data we concluded that the antigen recognized by SC02-357 is a pan myeloid antigen that is not expressed on uncommitted CD34$^+$ progenitor cells and lymphoid cells. The expression data generated using the phage antibody were confirmed using a phycoerythrin-conjugated human antibody that was generated from SC02-357 as described in Example 6 below.

Example 4

Identification of a Human C-Type Lectin as the Antigen Recognized by SC02-357

Figure 5:
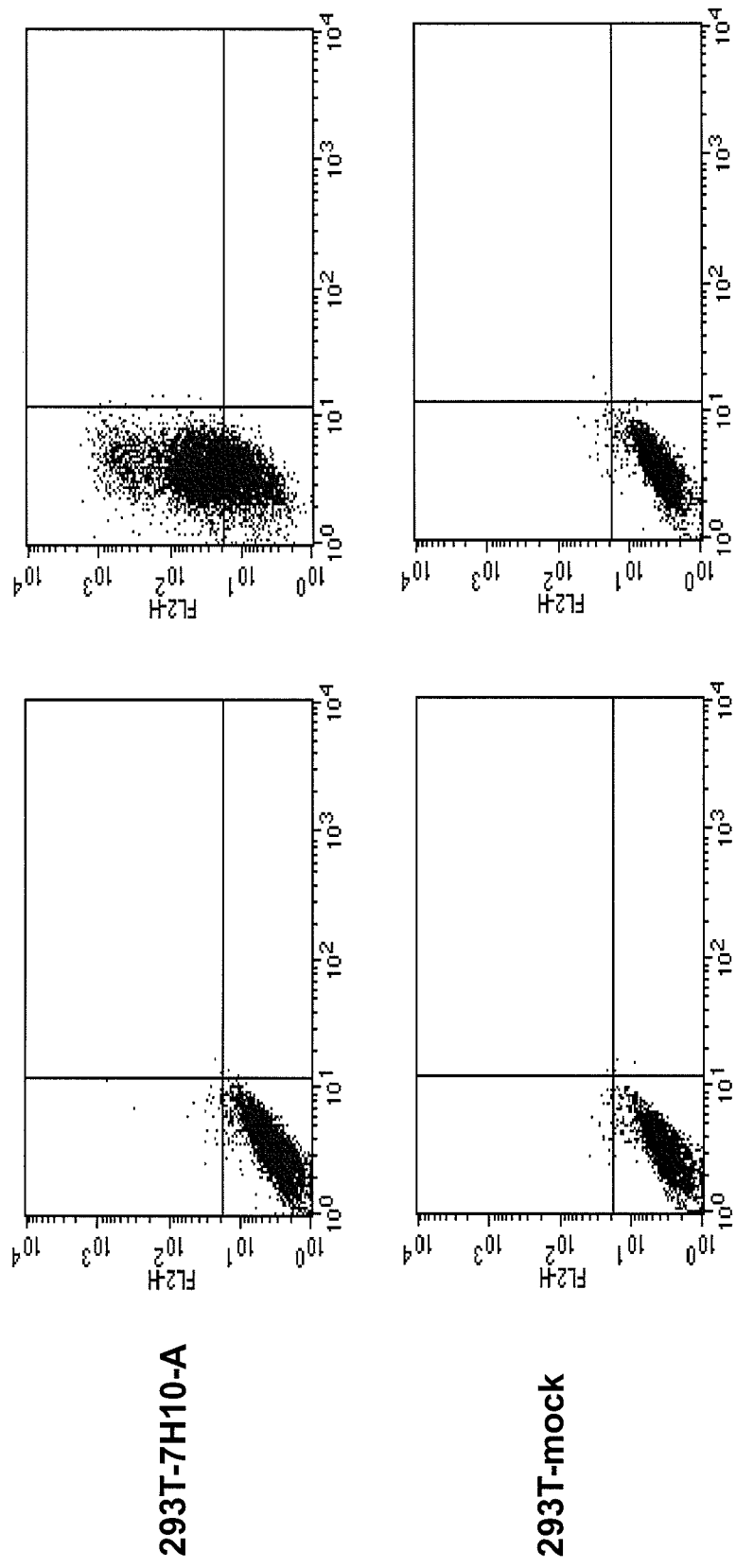
FIG. 5: Binding of the SC02-357 phage antibody to 293T cells transfected with control plasmid or with plasmid 7H10-A.

The expression cloning strategy as described by Aruffo et al., 1987 and Lanier et al., 1994 was used mutatis mutandis to identify the antigen recognized by SC02-357. A cDNA library prepared from human bone marrow (Invitrogen) was transfected into 293T cells using the lipofectamine (Life Technologies) or fugene (Roche) reagent according to protocols provided by the manufacturer. Forty-eight hours after transfection the cells were harvested using PBS containing 1 mM EDTA and were stained with a saturating amount of SC02-357 phage antibody as described in Example 3 supra. To avoid the selection of 293T cells expressing Fc-receptor-encoding cDNAs, the transiently transfected cells were co-stained with FITC-conjugated antibodies recognizing CD16, CD32 and CD64 (Pharmingen). Prior to cell sorting the stained cell suspension was passed over a 70 micron cell strainer and propidium iodide (PI) was added to the mixture to a final concentration of 0.25 µg/ml to allow the exclusion of dead cells. Cell sorting was performed using a FACSVantage flow cytometer (Becton Dickinson). Viable cells were gated based on forward and sideward scatter combined with a lack PI staining. Approximately 104 cells displaying bright SC02-357 staining (vizualized with streptavidin-PE) and no staining with CD16, CD32 and CD64 were sorted and collected in a total volume of 0.4 ml 0.6% SDS, 10 mM EDTA in H$_2$O. The obtained mixture was left at room temperature for 30 minutes, 0.1 ml of 5 M NaCl was added and the mixture was mixed thoroughly. Next, the mixture was left at 4° C. for minimally three hours. Upon centrifugation (five minutes at 12,000*g at 4° C.) the supernatant was transferred to a 1.5 ml tube and was extracted twice with an equal volume of phenol/chloroform/isoamylalcohol (25:24:1) and once with an equal volume of chloroform. The aqueous phase was transferred to a new tube to which 40 µg glycogen (Roche) was added and $\frac{1}{10}^{th}$ volume of 3 M NaAc pH 5.3 and 2.5 volumes of 96% ethanol. After precipitation for minimally 20 minutes at −20° C., the plasmid DNA was pelleted (15 minutes at 12,000*g at 4° C.), washed with 75% ethanol, dried and resuspended in 10 µl H$_2$O. Part of the DNA was used to transform ElectroMAX® DH10B-T1res electrocompetent *E. coli* cells (Life Technologies) using standard protocols known to a skilled person in the art. The transformed cells were used to inoculate LB agar plates supplemented with ampicillin and were incubated overnight at 37° C. The next day the colonies were scraped from the plates and plasmid DNA was extracted using standard technology to prepare a plasmid cDNA sublibrary. The above-mentioned procedure was repeated three times and resulted in 10-15% of SC02-357 reactive 293T cells upon transfection of the 3$^{rd}$ plasmid cDNA sublibrary. Hereafter, pools of colonies and subsequently single colonies were used to transfect 293T cells, resulting in the identification of a plasmid called 7H10-A with a 1.5 kb cDNA insert that was able to confer SC02-357 reactivity. As shown in FIG. 5, 293T cells transfected with the 7H10-A plasmid displayed bright staining by flow cytometry with SC02-357, while control 293T cells that had been transfected with an irrelevant plasmid cDNA were not recognized. Transfection of 293T cells with the 7H10-A plasmid also conferred reactivity with the scFvs SC02-378 and SC02-161. This demonstrates that these phage antibodies also recognize the same protein (data not shown).

Figure 6:
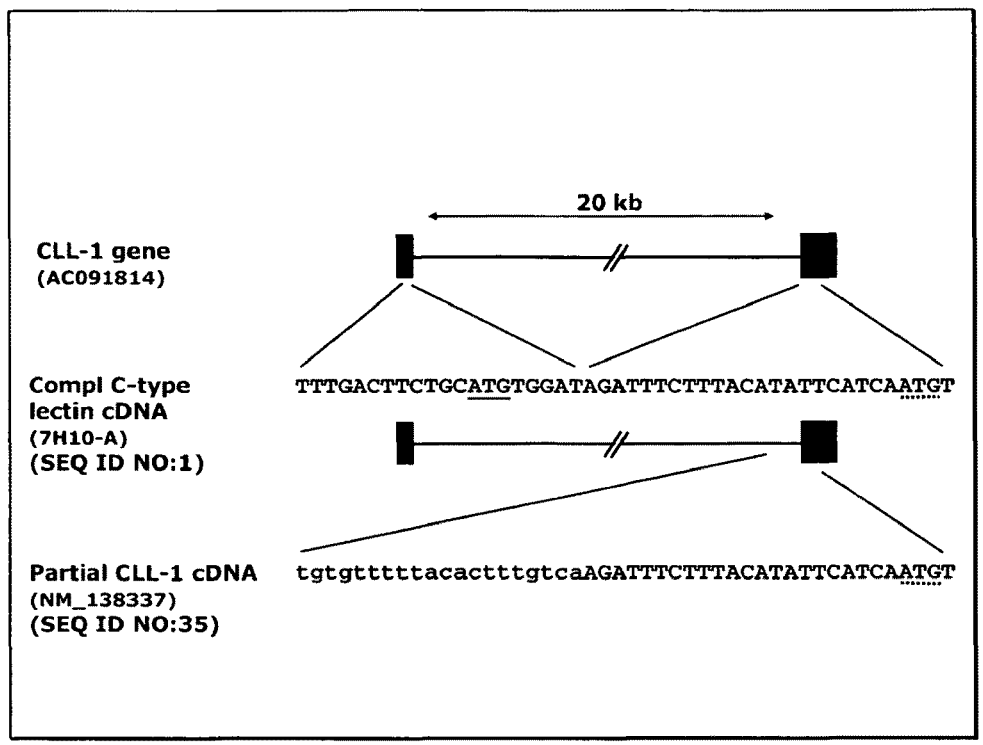
FIG. 6: Chromosomal organization of part of the gene (from base pair 20 to 65) encoding the human C-type lectin (SEQ ID NO:1). The start codon of the human C-type lectin is underlined. The start codon of the CLL-1 protein is underlined with a dotted line (SEQ ID NO:35).

The nucleotide sequence of the cDNA insert of the plasmid 7H10-A was determined according to standard techniques known to the skilled artisan. A GenBank search revealed that the 1492 bp 7H10-A cDNA insert (SEQ ID NO:1) was nearly identical to a mRNA sequence encoding the human C type lectin-like (CLL-1) protein (Acc. No. NM_138337). Some small differences with the deposited CLL-1 sequence were observed. Apart from the first stretch of 39 nucleotides, full homology was observed between 7H10-A and the described CLL-1 mRNA with the proviso that three single nucleotide substitutions were found: one silent substitution at position 256, C (in 7H10-A) vs T (in CLL-1); one substitution at position 791, A (in 7H10-A) vs T (in CLL-1), resulting in an amino acid change from glutamine to lysine; and a silent substitution at position 879, T (in 7H 10-A) vs G (in CLL-1). The latter substitution has been recognized as an allelic single nucleotide polymorphism (see, Genbank NM_138337). The CLL-1 gene is localized within the NK gene complex on the telomeric region of chromosome 12. Alignment of the 7H10-A cDNA clone with a bacterial artificial chromosome (BAC) containing a part of human chromosome 12 (Acc. No. AC091814) explained the difference between the 7H10-A cDNA and the deposited CLL-1 mRNA (Acc. No. NM_138337). The first stretch of nucleotides of the 7H10-A cDNA that did not match the deposited CLL-1 mRNA was identical to one region in the BAC clone whereas the subsequent nucleotide sequence of the cDNA annealed to another region that was separated by 20 kb of non-homologous intronic DNA (FIG. 6). Since the 5' region of the deposited CLL-1 cDNA (NM_138337) that does not match 7H10-A is completely homologous to this second intron-exon boundary in the BAC clone, it is clear that the deposited cDNA clone still contains intronic DNA and therefore reflects a partially or alternatively spliced mRNA. The 7H10-A cDNA obtains an ORF encoding a 275 amino acid long type II transmembrane protein (SEQ ID NO:2). The predicted polypeptide has an intracellular region of 53 amino acids, a 23 amino acid long transmembrane region, and a 199 amino acid long extracellular domain. The presence of several characteristic structural motifs in the extracellular region indicates that this protein is a member of the C-type lectin superfamily. Interestingly, the 7H10-A cDNA contains an open reading frame that extends the deposited CLL-1 protein with an extra ten amino acids at its N-terminus, adding a $YX_1X_2M$ motif (SEQ ID NO:33) to the intracellular domain of CLL-1. In addition, the cytoplasmic domain contains an $I/VX_1YX_2X_3L$ (SEQ ID NO:34) immunotyrosine-based inhibition motif (ITIM).

Example 5

Expression of mRNA of the Human C-Type Lectin in Human Tissues

In order to determine mRNA expression of the human C-type lectin in human tissues including heart, brain, placenta, lung, liver, skeletal muscle, kidney, pancreas, spleen, thymus, prostate, testis, ovary, small intestine, colon and PBL, a PCR strategy was developed to specifically detect the mRNA of the human C-type lectin. Therefore, the following primers were designed: forward primer 5'-GTGATGATGTC-CAAACATGGC-3' (SEQ ID NO:20), reverse primer 5'-GAT-TGATGCCTCATGCCTCC-3' (SEQ ID NO:21) (Proligo Primers & Probes), which yields a PCR product of 365 base pairs. The primers for beta-actin were: forward primer 5'-GGCATCGTGATGGACTCCG-3' (SEQ ID NO:22), reverse primer 5'-GCTGGAAGGTGGACAGCGA-3' (SEQ ID NO:23) (Proligo Primers & Probes), resulting in a 612 base pair PCR product. PCR was performed with TITANIUM Taq PCR Kit (Becton Dickinson) according to the instructions. Five μl of each human tissue cDNA (Becton Dickinson) was used as template in a 50 μl PCR reaction containing 1 μl 50 X dNTPs (10 mM each), 5 μl of 10× TITANIUM Taq PCR buffer, 1 μl of 50× TITANIUM Taq Polymerase, and 1 μl of each primer (10 μM). PCR reactions were carried out in a Biometra T3 thermocycler by incubating reactions for one minute at 94° C., followed by 25 cycles of (30 seconds at 94° C., one minute at 60° C.), and a five-minute extension time at 68° C. Ten μl of each reaction product was analyzed on a 1% TAE agarose gel.

Figure 7:
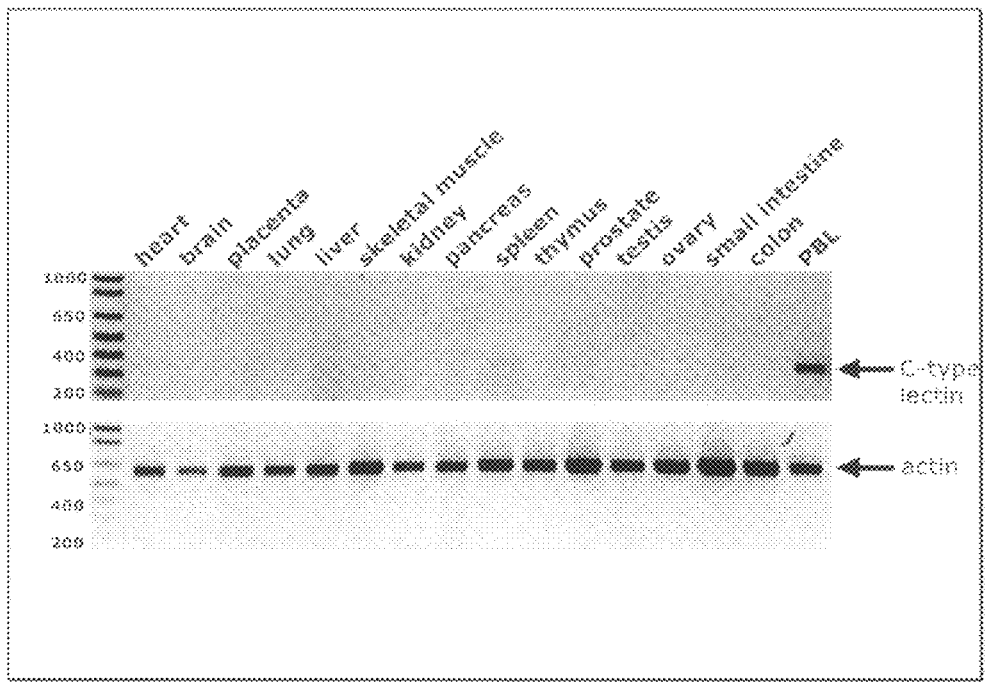
FIG. 7: mRNA expression of the human C-type lectin in human tissues.

As shown in FIG. 7, expression of mRNA of the human C-type lectin could only be detected in peripheral blood leukocytes, which is in agreement with results from FIG. 2 showing specific staining of SC02-357 on granulocytes, dendritic cells, and monocytes, three subsets within peripheral blood leukocytes. A very faint band was visible in spleen, which can be explained by the presence of myeloid cells within this tissue.

Example 6

Generation of 357, 378, and 161 IgG1 Molecules

Figure 8:
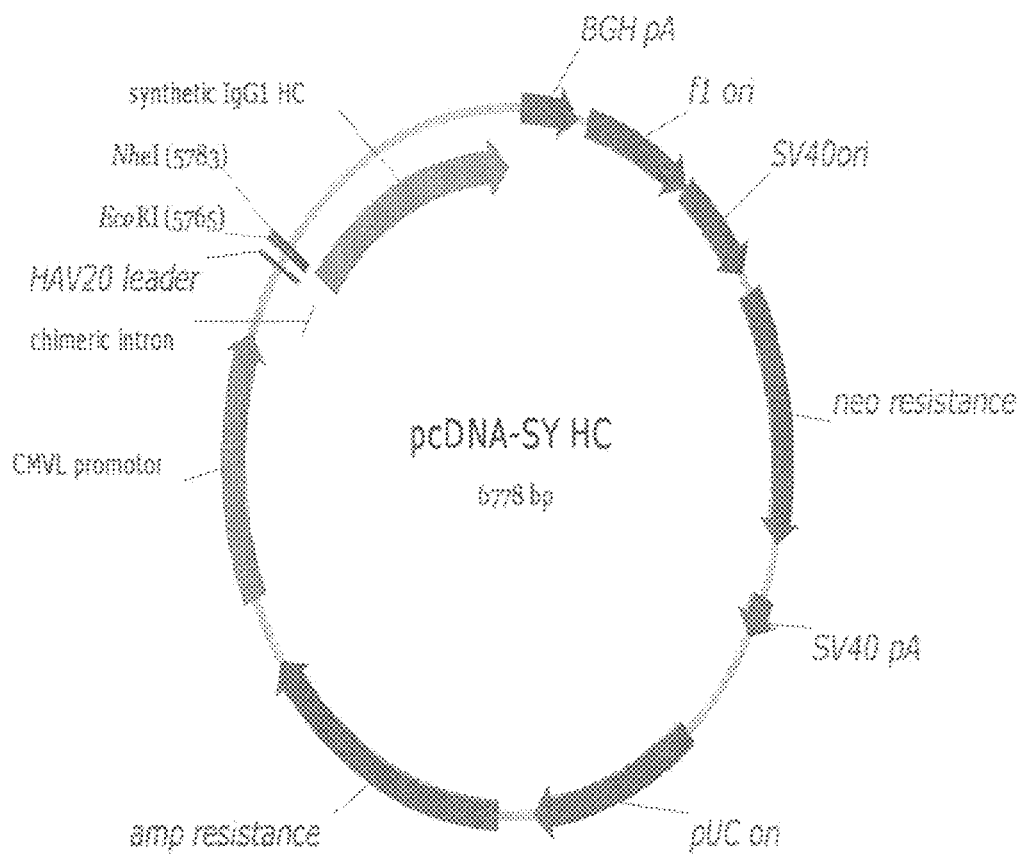
FIG. 8: The expression vector pcDNA-SY-HC.
Figure 9:
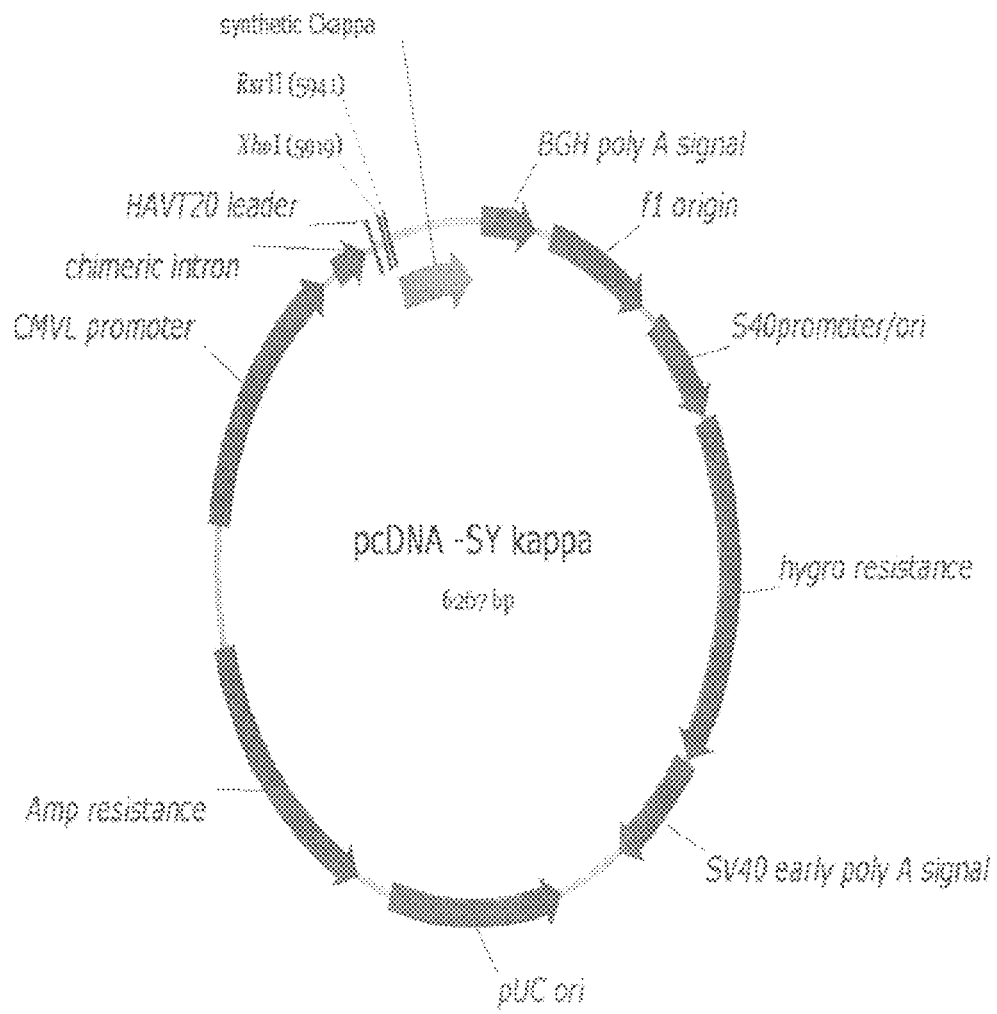
FIG. 9: The expression vector pcDNA-SY-κ.

Heavy- and light chain variable regions of the scFvs SC02-357, SC02-378 and SC02-161 were PCR-amplified using oligonucleotides to append restriction sites and/or sequences for expression in the IgG expression vectors pcDNA-SY-HC (see, FIG. 8; SEQ ID No:24) en pcDNA-SY-κ (see, FIG. 9; SEQ ID NO:25). The VL gene shared between these scFvs was amplified using oligonucleotides 5K-1 (SEQ ID NO:26) and sy3K-C (SEQ ID NO:27) (see, below). The PCR products were cloned into vector pcDNA-SY-κ and the nucleotide sequences were verified according to standard techniques known to the skilled artisan. VH genes were amplified using oligonucleotides 5H-F (SEQ ID NO:28) and sy3H-A (SEQ ID NO:29). Thereafter, the PCR products were cloned into vector pcDNA-SY-HC and nucleotide sequences were verified according to standard techniques known to the skilled person in the art.

```
5H-F
                                      (SEQ ID NO: 28)
acctgtcttgaattctccatggcccaggtgcagctgcaggagtccgg
ccc sy3H-A
                                      (SEQ ID NO: 29)
gcccttggtgctagcgctggagacggtcaccagggtgccctggcccc 5K-I
                                      (SEQ ID NO: 26)
acctgtctcgagttttccatggctgacatccagatgacccagtctcc
atcctcc sy3K-C
                                      (SEQ ID NO: 27)
gggaccaaggtggagatcaaacggaccgtggccgccccagc
```

Figure 10:
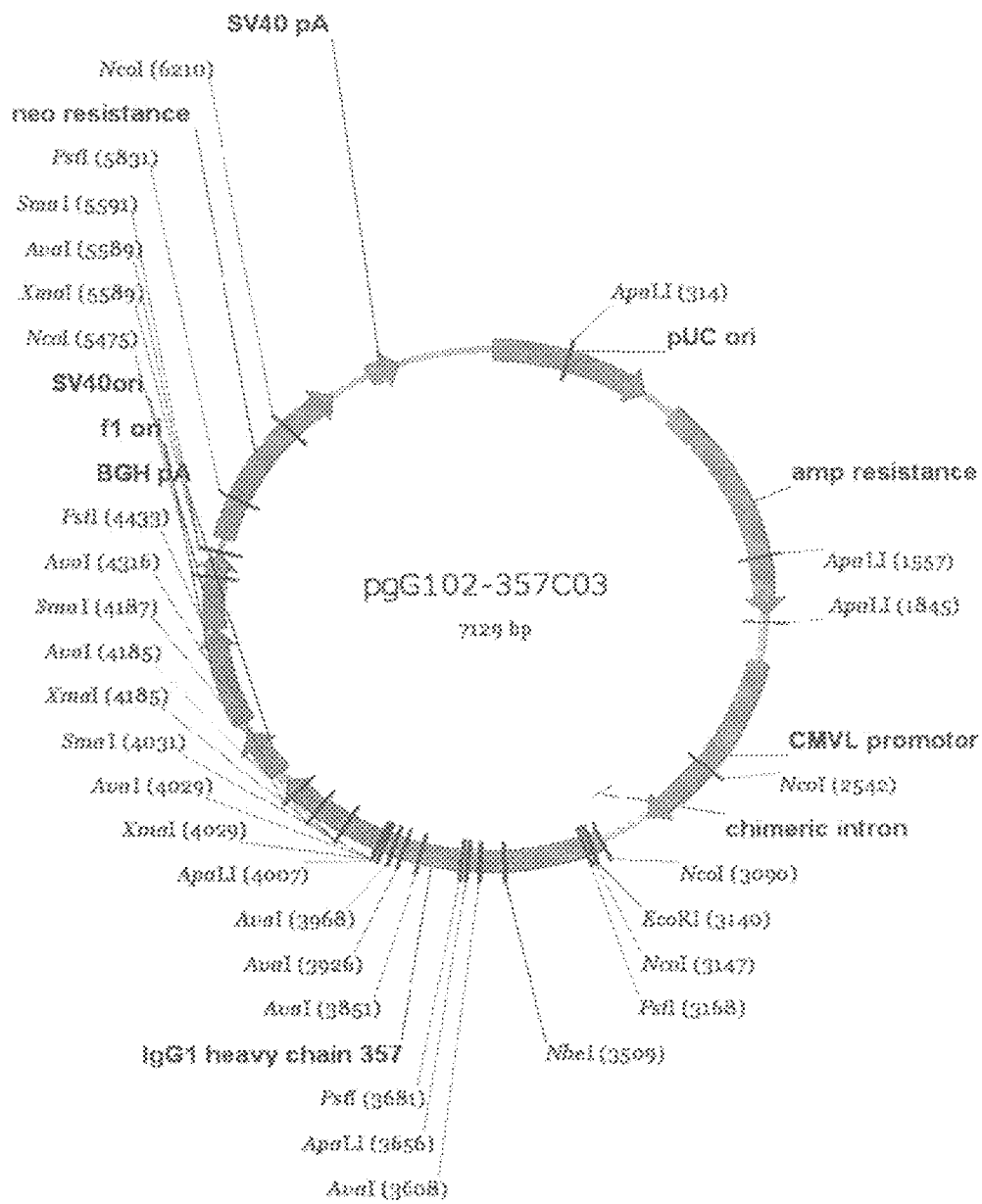
FIG. 10: The expression construct pgG102-357C03 (also called pcDNA-SY-HC357).
Figure 11:
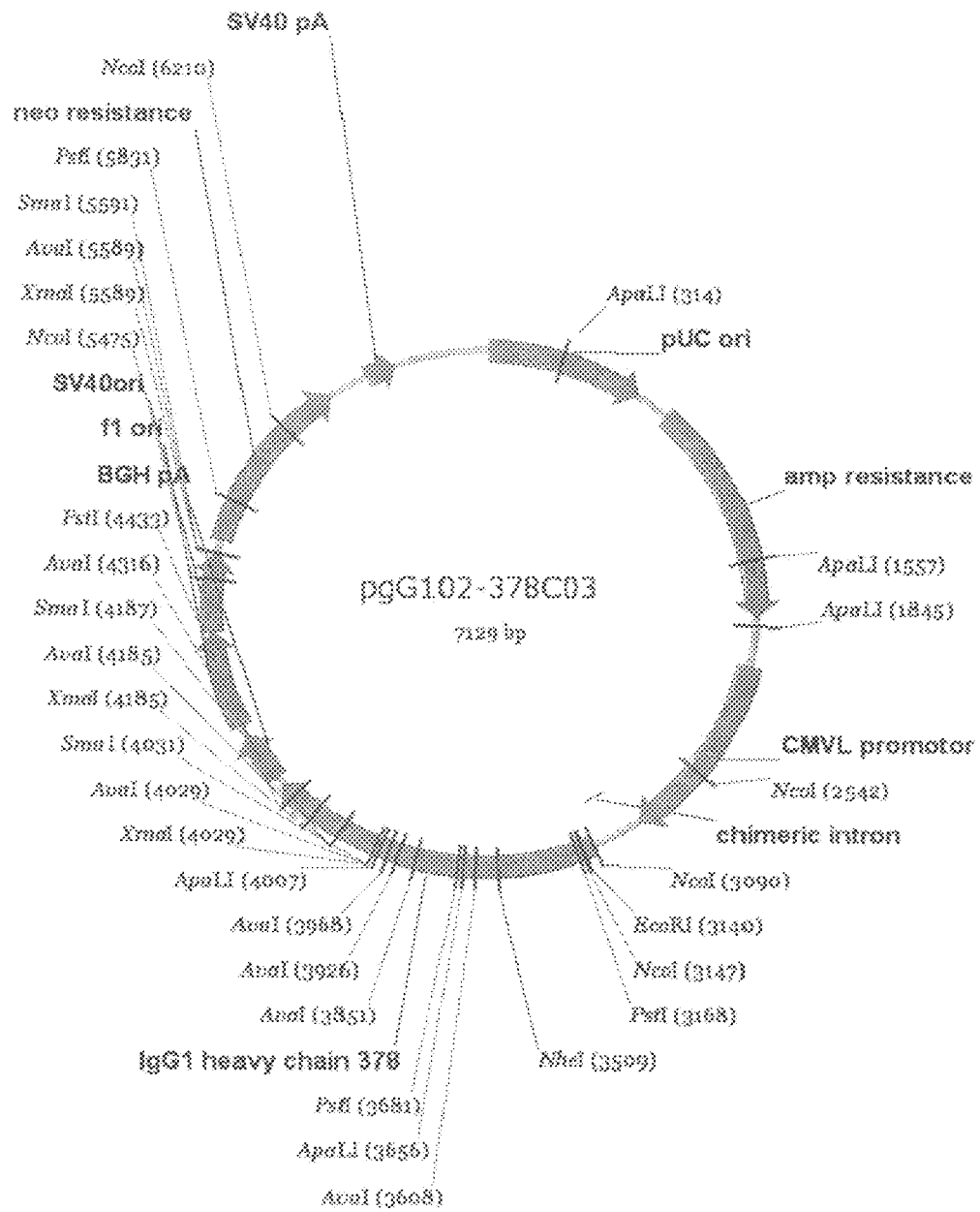
FIG. 11: The expression construct pgG102-378C03 (also called pcDNA-SY-HC378).
Figure 12:
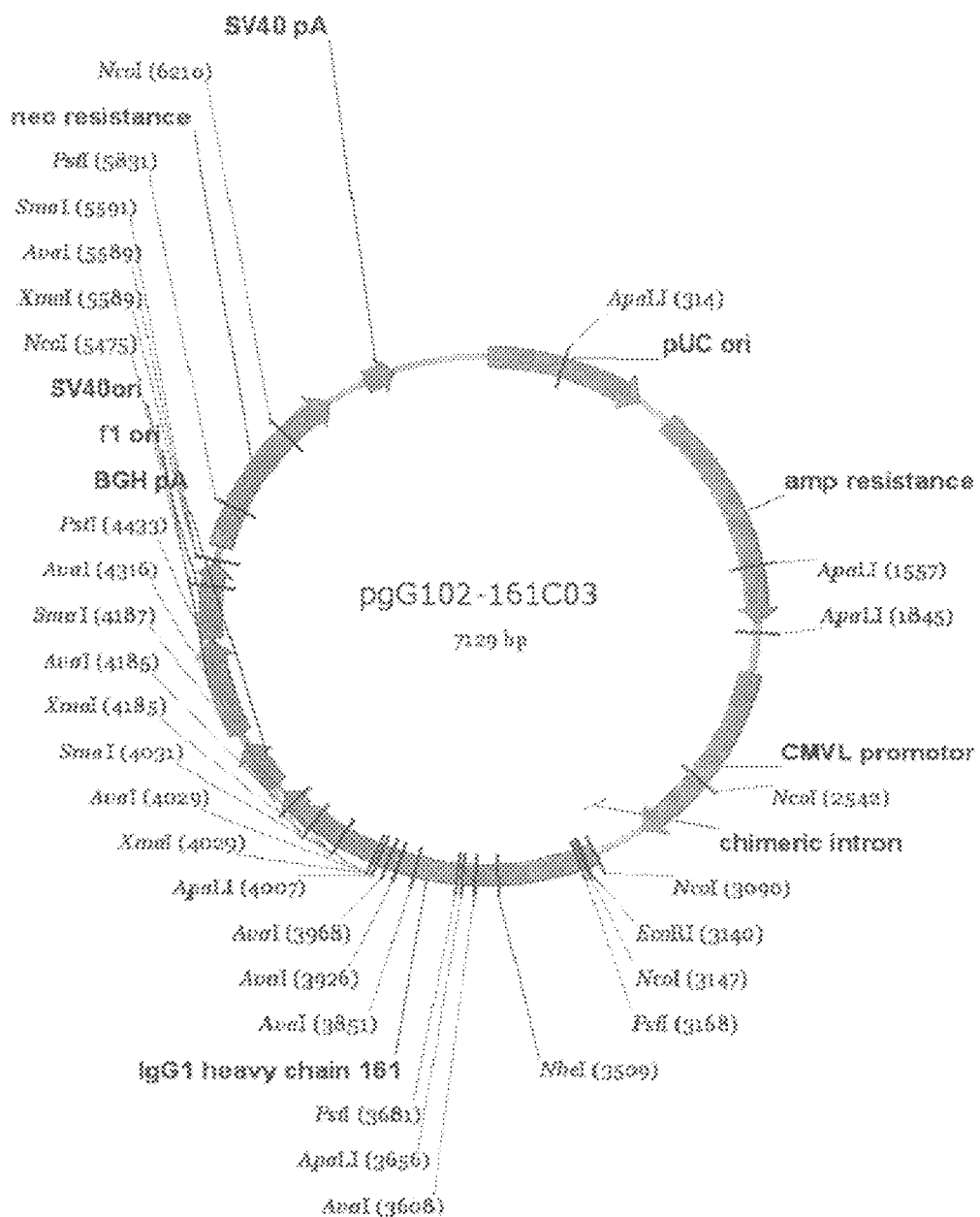
FIG. 12: The expression construct pgG102-161C03 (also called pcDNA-SY-HC161).
Figure 13:
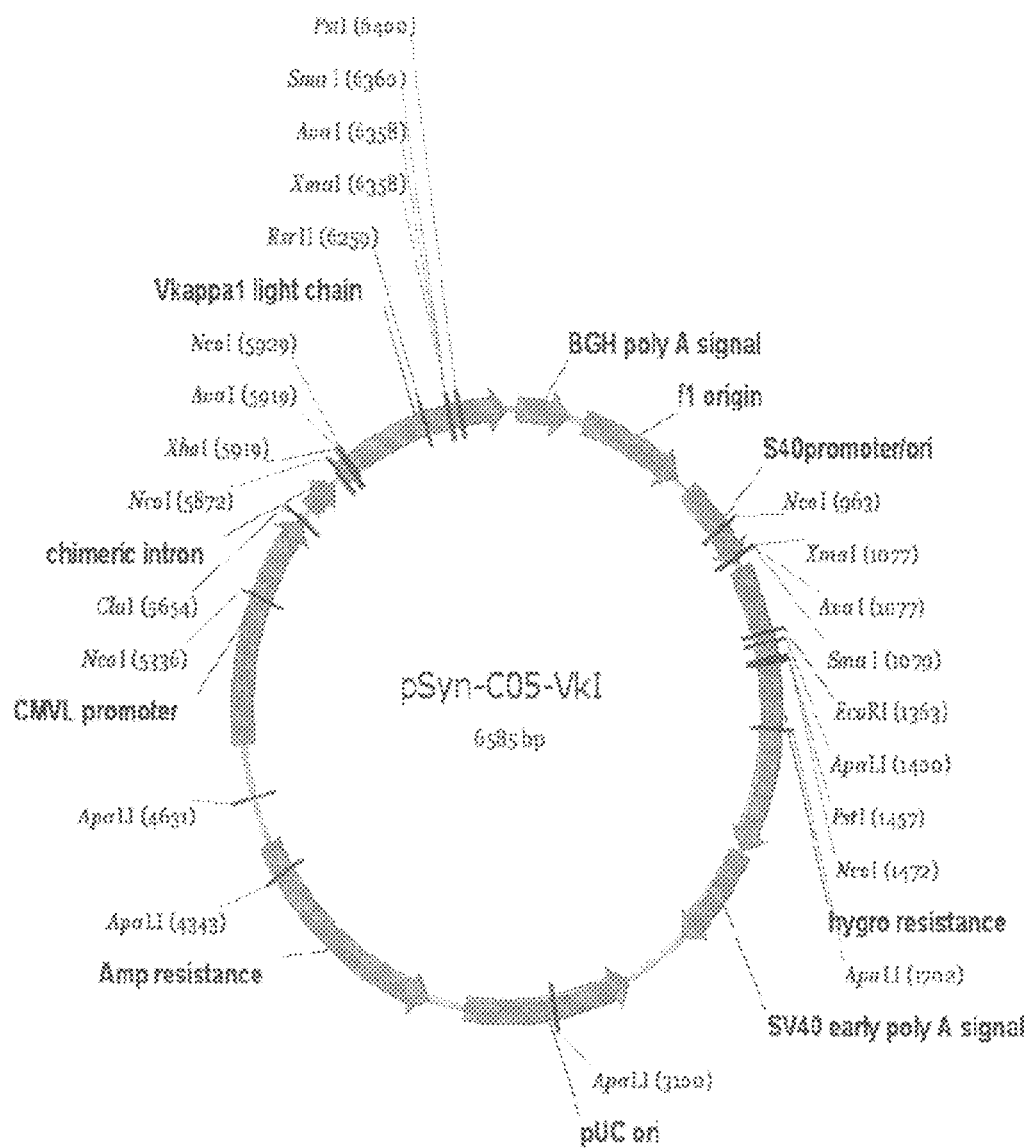
FIG. 13: The expression construct pSyn-C05-VkI (also called pcDNA-SY-LC-Vκ1).

The resulting expression constructs pcDNA-SY-HC357 (see, FIG. 10, wherein this expression construct is called pgG102-357C03), pcDNA-SY-HC378 (see, FIG. 11, wherein this expression construct is called pgG102-378C03), and pcDNA-SY-HC161 (see, FIG. 12, wherein this expression construct is called pgG102-161C03) encoding the human anti-human C-type lectin IgG1 heavy chains were transiently expressed in combination with the pcDNA-SY-Vκ1-Cκ construct (see, FIG. 13, wherein this expression construct is called pSyn-C05-VkI) encoding the shared light chain in 293T cells and supernatants containing IgG1 antibodies were obtained. The nucleotide sequences of the heavy chains of the antibodies called 357, 378 and 161 are shown in SEQ ID NOS:6, 8 and 10, respectively. The amino acid sequences of the heavy chains of the antibodies called 357, 378 and 161 are shown in SEQ ID NOS:7, 9 and 11, respectively.

The nucleotide sequences of the shared light chain of the antibodies is shown in SEQ ID NO:12. The amino acid sequences of the shared light is shown in SEQ ID NO:13. Subsequently, the antibodies were purified over size-exclusion columns and protein-A columns using standard purification methods used generally for immunoglobulins (see, for instance, WO 00/63403).

Figure 14:
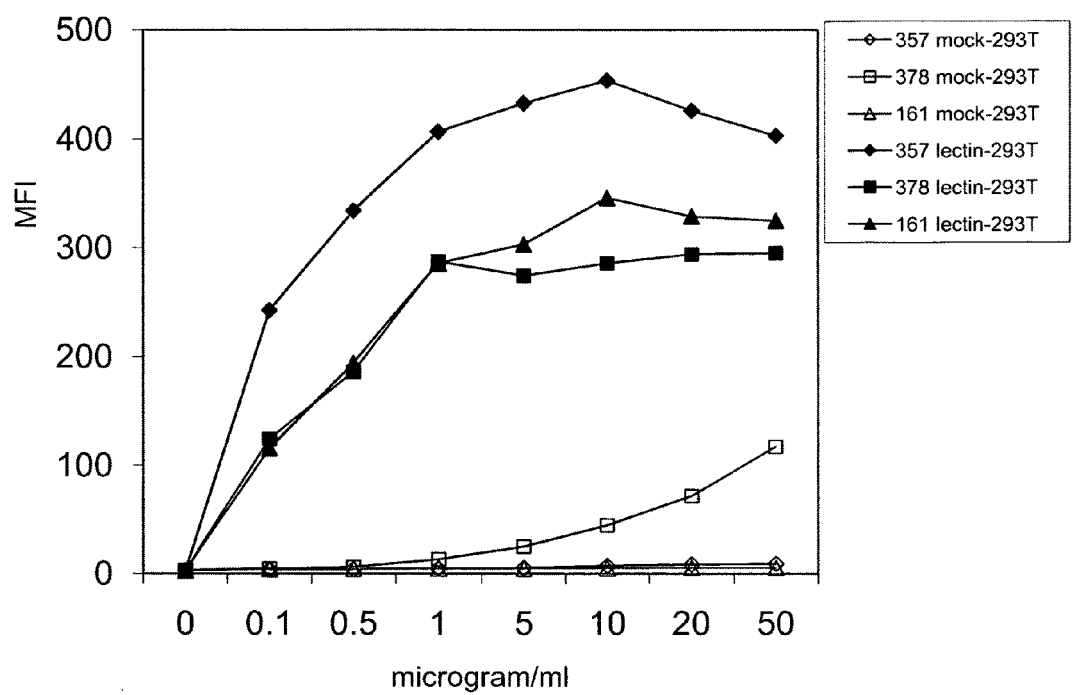
FIG. 14: Analysis of the binding of the antibodies called 357, 378 and 161 to 293T cells transfected with the human C-type lectin and 293T cells transfected with an irrelevant cDNA. On the Y-axis the mean fluorescence intensity is shown and on the X-axis the amount of antibody in μg/ml is shown.

The anti-human C-type lectin IgG1 antibodies were validated for their ability to bind to 293T cells transfected with the human C-type lectin. To this purpose $2*10^5$ 293T cells transfected with the human C-type lectin were stained with IgG1 antibodies at concentrations ranging from 0 to 50 μg/ml at 4° C. Binding of the antibodies called 357, 378 and 161 was visualized using biotinylated goat-anti-human IgG (Fc specific, Caltag) followed by streptavidin-phycoerythrin (Caltag). The stained cells were analyzed by flow cytometry. As shown in FIG. 14, all anti-human C-type lectin IgG1 antibodies specifically stained the 293T cells transfected with the human C-type lectin whereas 293T cells transfected with an irrelevant cDNA were not recognized. To allow direct analysis of cell surface expressed human C-type lectin in further experiments the anti-human C-type lectin antibody 357 was directly labeled with phycoerythrin (IQ Products, Groningen, the Netherlands).

Example 7

Expression of the Human C-Type Lectin in Human Tissues

For use in immunohistochemistry, bivalent scFv, produced by *Pichia pastoris*, were generated. Bivalent scFv were generated for the anti-human C-type lectin scFv called SC02-357 and for a positive control scFv recognizing CD46.

Figure 15A:
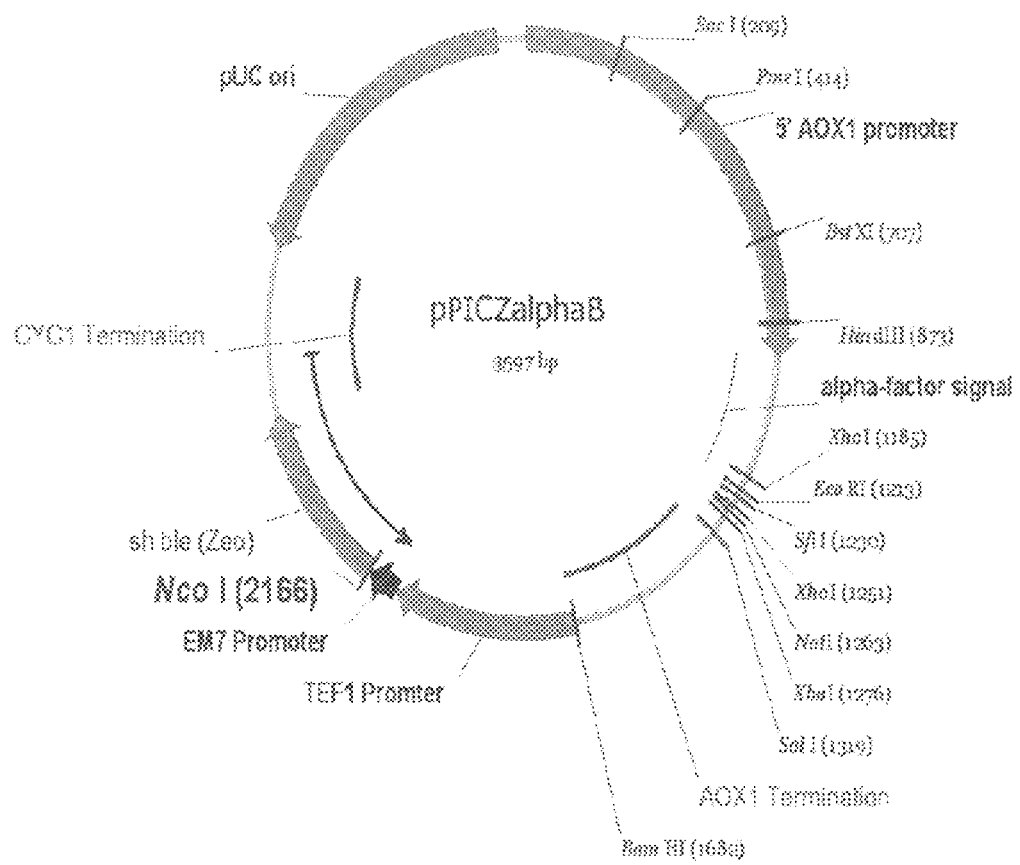
In FIG. 15A, the vector pPICZαB is shown and in FIG. 15B the bivalent scFv expression vector pPicZbiFVH is shown.
Figure 15B:
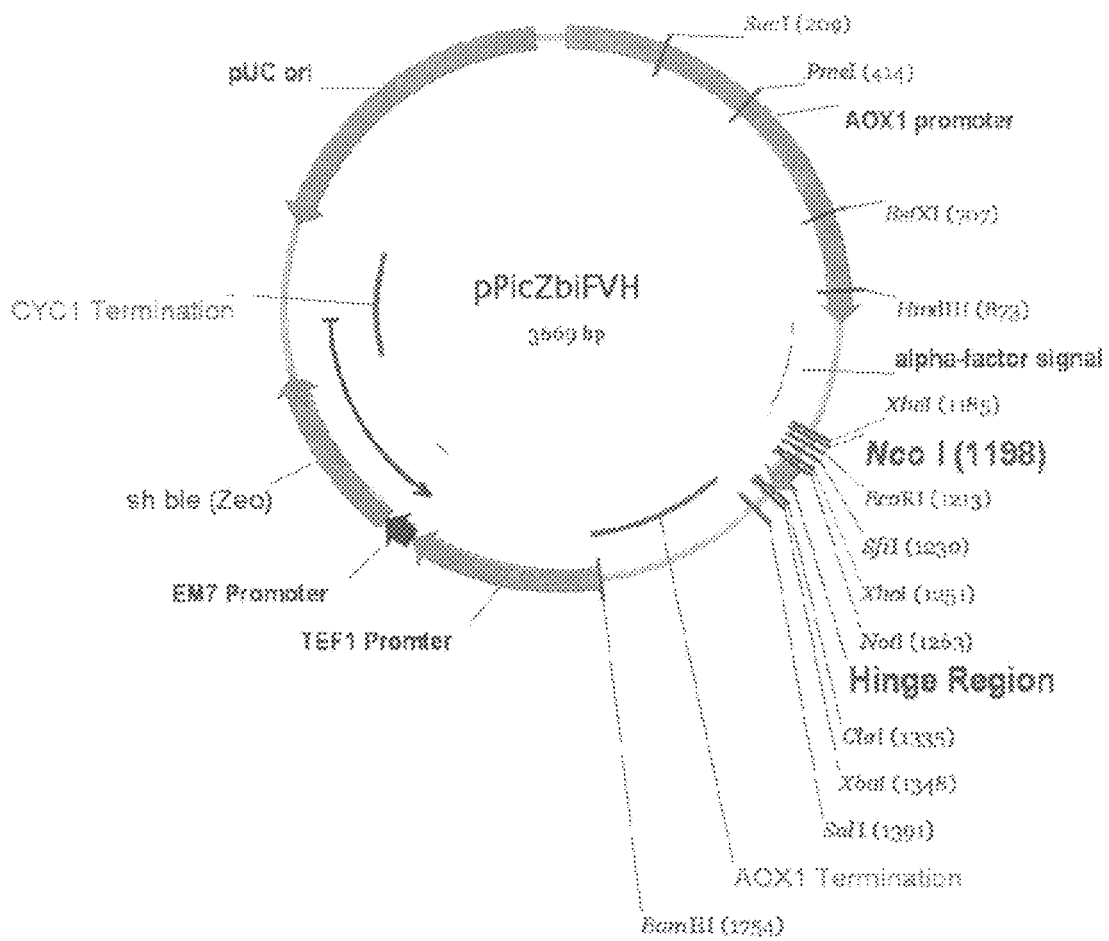
FIG. 15.
FIG. 15C shows the cloning strategy of scFvs into pPicZbiFVH (SEQ ID NOS:36-41, respectively, from top to bottom of FIG. 15C).
Figure 16:
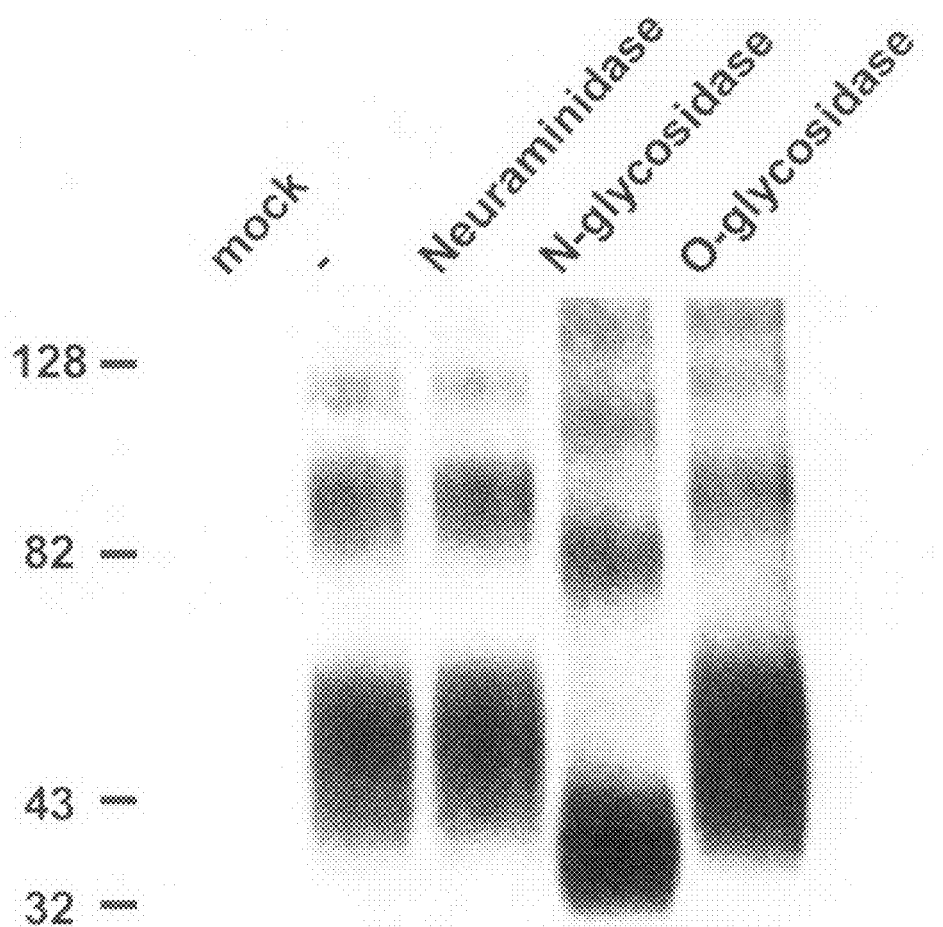
FIG. 16: Immunoprecipitation of 293T cells transfected with the human C-type lectin treated with or without neuramidase, N-glycosidase or O-glycosidase.

Methods for the cloning and expression of bivalent scFv fragments in the *Pichia pastoris* system are based on protocols provided by the supplier (Invitrogen) in "A Manual of Methods for Expression of Recombinant Proteins Using pPICZ and pPICZα in *Pichia pastoris* (Version F)." The bivalent scFv expression vector pPicZbiFVH (see, FIG. 15B) was constructed from the vector pPICZαB (see, FIG. 15A) (Invitrogen) following standard molecular biology techniques known to a person skilled in the art. Three modifications were introduced in the pPICZαB (see, FIG. 15C):
1. A restriction site (NcoI) was introduced by PCR-generated point mutation directly after the KEK2 cleavage site of the signal peptide to facilitate cloning into the vector.
2. A second NcoI restriction site was removed by PCR generated point mutation inside the coding region of the sh ble gene.
3. A synthetic fragment comprising the hinge region of murine IgG3 and a linker fragment was introduced between the restriction sites Nod and)(bal.

All modifications were confirmed by sequencing. ScFvs were cloned into pPicZbiFVH from the phage display expression vector by directional cloning using the restriction sites NcoI and NotI. The *Pichia pastoris* strain SMD1168 kek1:suc1 (ATCC #204414) was transformed with 5-10 μg of linearized construct cDNA by electroporation according to the manufacturer's protocols (supra). The transformed cells were plated on YPDS agar containing 250 Zeocin and incubated at 30° C. for three to four days. High producing clones were selected by colony lift immunoblot screening, as follows. Pre-wet nitrocellulose membranes were layered over the transformation plates and a fraction of each colony was lifted onto the membrane. The membrane was then placed colony side up on YPD agar containing 0.5% methanol and incubated overnight at 30° C. The membranes were then washed repeatedly with Tris buffered saline containing 0.5% Tween-20 (TBST) to remove colonies, then blocked for 30 minutes with TBST and 4% non-fat milk powder. The membranes were then placed in TBST containing 4% non-fat milk powder and horseradish peroxidase conjugated anti-c-myc antibody (Roche) for one hour. Finally, the membranes were washed extensively in TBST followed by a PBS washing step and scFv-secreting colonies were revealed by a chemofluorescence detection system (Apbiochem). Selected high producers were purified by streaking on YPD plates and were subsequently used for bivalent scFv expression. Small-scale expression cultures were carried out in shaker flasks essentially as described by the manufacturer's protocols (supra). BMGY medium was used for the cell expansion phase, while BMMY medium was used during the bivalent scFv expression phase. After 48 hours of induction, supernatants were clarified by repeated centrifugation. The supernatant was conditioned for purification by the addition of 1 M $Na_2HPO_4$ pH 8 to a concentration of 20 mM, 0.5 M Imidazole to a concentration of 10 mM, 5 M NaCl to a concentration of 500 mM. Hereafter, the samples were purified by immobilized metal affinity chromatography followed by anion exchange chromatography on an AKTAprime FPLC-system (Pharmacia). A 5 ml HiTrap chelating column (Pharmacia) was charged with $NiSO_4$ and equilibrated according to the manufacturer's instructions. Conditioned supernatant was loaded directly onto the column and washed extensively in equilibration buffer (20 mM $Na_2PO_4$ pH 8, 10 mM imidazole). Bivalent scFv were eluted directly off the column on to a 1 ml sepharose Q HP column (Pharmacia) in the presence of 250 mM imidazole pH 8.5. The column was then washed in 20 mM Tris-HCl pH 8, then briefly in 20 mM $Na_2PO_4$ pH 7.3, and bivalent scFvs were eluted off the column over a gradient of 0-0.5 M NaCl in seven column volumes. Fractions were then measured for protein content and were analyzed for activity and purity.

The anti-human C-type lectin bivalent scFv SC02-357 was analyzed for its ability to bind to normal tissues by immunoperoxidase staining. To this purpose, frozen sections of the following normal tissues: adrenal gland; bladder; brain (cerebellum and cerebrum); blood vessels (aorta and coronary artery); fallopian tube; esophagus; stomach (antrum and body); duodenum; ileum; colon; heart; kidney; liver; lung; lymph node; ovary; pancreas; parathyroid; peripheral nerve; pituitary gland; placenta; prostate; salivary gland; skin; spinal cord; spleen; striated muscle; testis; tonsil; thyroid; ureter and uterus (cervix and endometrium) were cut, mounted on glass slides and were dried at room temperature. The sections were blocked with 50 mM sodiumazide containing 0.035% $H_2O_2$ for 20 minutes, followed by blocking with PBS containing 4% BSA prior to incubation with the anti-human C-type lectin bivalent scFv for 60 minutes at room temperature. Hereafter, the sections were fixed with 4% formaldehyde for 30 minutes. Bound bivalent scFv were visualized using the 9E10 anti-myc mAb hybridoma supernatant followed by Envision anti-mouse IgG amplification reagent (Dako) and incubation with diaminobenzene (DAB). The sections were counterstained with hematoxylin, dehydrated and mounted. As controls, all sections were stained with no bivalent scFv and with a bivalent scFv recognizing human CD46 (positive control), respectively.

Among all the tissue types analyzed, specific human C-type lectin staining was only observed in spleen (see, Table 3). The human C-type lectin expression within spleen was detected in tissue granulocytes, a finding that is consistent with the observed tissue distribution of the human C-type lectin at the mRNA level.

Example 8

Affinity Measurement with Anti-Human C-Type Lectin Immunoglobulin Molecules

For affinity measurement purposes a recombinant soluble human C-type lectin molecule is produced in *P. pastoris*. For this purpose, a cDNA construct is generated in the pPICZα vector that allows the expression of the soluble extracellular domain of the human C-type lectin molecule in *Pichia pastoris* following standard molecular biology techniques known to a person skilled in the art.

Methods for cloning and expressing soluble human C-type lectin molecule in the *P. pastoris* system are based on protocols provided by the manufacturer (Invitrogen) in "A Manual of Methods for Expression of Recombinant Proteins Using pPICZ in *Pichia pastoris* (Version F)." The integrity of the pPicZsolhumanC-typelectin construct is confirmed by sequencing. The *P. pastoris* strain SMD1168 kek1:suc1 (ATCC #204414) is transformed with 5 to 10 µg of linearized construct cDNA by electroporation according to the manufacturer's protocols (supra). The transformed cells are plated on YPDS agar containing 250 µg/ml zeocin and incubated at 30° C. for three to four days. High producing clones are selected by colony lift immunoblot screening, as follows. Pre-wet nitrocellulose membranes are layered over the transformation plates and a fraction of each colony was lifted onto the membrane. The membrane is then placed colony side up on YPD agar containing 0.5% methanol and incubated overnight at 30° C. The membranes are then washed repeatedly with Tris buffered saline containing 0.5% Tween 20 (TBST) to remove colonies and are then blocked for 30 minutes with TBST containing 4% non-fat milk powder. The membranes are then placed in TBST containing 4% non-fat milk powder and horseradish peroxidase conjugated anti-c-myc antibody (Roche) for one hour. Finally, the membranes are washed extensively in TBST followed by a PBS washing step and human C-type lectin-secreting colonies are revealed by a chemofluorescence detection system (Apbiochem). Selected high producers are purified by streaking on YPD plates and are subsequently used for expression of the soluble human C-type lectin protein. Small-scale expression cultures are carried out in shaker flasks essentially as described by the manufacturer's protocols (supra). BMGY medium is used for the cell expansion phase, while BMMY medium is used during the protein expression phase. After 48 hours of induction, supernatants are clarified by repeated centrifugation. The supernatant is conditioned for purification by the addition of 1 M $Na_2HPO_4$ pH 8 to a concentration of 20 mM, 0.5 M imidazole to a concentration of 10 mM, 5 M NaCl to a concentration of 500 mM. Hereafter, the samples are purified by immobilized metal affinity chromatography followed by anion exchange chromatography on an AKTAprime FPLC system (Pharmacia). A 5 ml HiTrap chelating column (Pharmacia) is charged with $NiSO_4$ and equilibrated according to the manufacturer's instructions. Conditioned supernatant is loaded directly on to the column and washed extensively in equilibration buffer (20 mM $Na_2PO_4$ pH 8, 10 mM Imidazole). Soluble human C-type lectin protein is eluted directly off the column on to a 1 ml sepharose Q-HP column (Pharmacia) in the presence of 250 mM imidazole pH 8.5. The column is washed in 20 mM Tris-HCl pH 8, then briefly in 20 mM $Na_2PO_4$ pH 7.3, and human C-type lectin is eluted off the column over a gradient of 0 to 0.5 M NaCl in seven column volumes. Fractions are then measured for protein content and are analyzed for activity and purity.

The affinities of the human anti-human C-type lectin IgGs called 357, 378, and 161 are determined using Biacore 2000. For $K_{off}$-ranking, the purified human IgG1 antibodies are applied directly to NTA sensor chips coupled with 10,000 resonance units (RU) of purified human C-type lectin. Antibody affinity data are based on measuring several different preparations of antibody at seven concentrations on sensor chips coated with different concentrations (500 to 4000 RU) of human C-type lectin.

Example 9

Biochemical Characterization of the Human C-Type Lectin

To characterize the human C-type lectin, the cell surfaces of $10^8$ 293T cells transfected with human C-type lectin as well as mock-transfected 293T cells were biotinylated during one hour at room temperature with 2 mg sulfo-NHS-LC-LC-biotin in physiological buffer (0.2 M phosphate buffer containing 0.12 M NaCl, pH 7.4). Subsequently, the remaining free biotin was blocked during a 30 minute incubation at room temperature with 10 mM glycine in physiological buffer. After labeling, the cells were washed with cold physiological buffer and solubilized for 30 minutes at 4° C. at a concentration of $3\times10^7$ cells/ml in Triton X-100 lysis buffer (1% Triton X-100, 150 mM NaCl, 50 mM Tris pH 7.4, protease inhibitors (Roche)). The unsoluble material was removed by centrifugation for 30 minutes at 4° C. at 20,000*g. Hereafter, the biotinylated solubilized lysates were pre-cleared with protein-A beads for two hours at 4° C. During two hours at room temperature, 4 mg of 357 IgG antibody was coupled to protein-A beads. As a control, an irrelevant human IgG1 antibody was used. The pre-cleared samples were next incubated with the IgGs coupled to sepharose-A beads for two hours at 4° C. The protein-A beads were washed four times with 1 ml of Triton X-100 lysis buffer and bound complexes were eluted by the addition of sample loading buffer. The samples were subjected to SDS-PAGE under non-reducing and reducing conditions. After blotting on PVDF membranes, the biotinylated proteins were detected with streptavidin-HRP (Amersham) and enhanced chemoluminescence (Amersham).

To analyze the glycosylation status of the human C-type lectin protein the same procedure was followed as described supra, except that the human C-type lectin proteins were eluted from the protein-A beads by incubation for 15 minutes in elution buffer (1% Triton X-100, 150 mM NaCl, 100 mM Glycine pH 2.7, protease inhibitors). To the eluted biotinylated human C-type lectin proteins ⅕ volume of 1 M $Na_2PO_4$ was added for neutralization. Subsequently, 1/10 volume of 1% NP-40 was added, and the purified human C-type lectin was digested with 50 units of neuraminidase (Roche) for one hour at 37° C. Subsequently, one part of the desialylated samples was incubated with 16 units of O-glycosidase (Roche), while the other part was incubated with 4 units of N-glycosidase (Roche) for 19 hours at 37° C. The samples were subjected to SDS-PAGE under non-reducing and reducing conditions and Western blotting as described supra. Immunoprecipitation of 293T cells transfected with human C-type lectin using the human anti-human C-type lectin antibody revealed a prominent band of approximately 45 kD (FIG. 16). An additional band was observed that migrated around 90 kD, suggesting that the human C-type lectin molecule might form homodimers. However, this is unlikely since this banding pattern is identical under both non-reducing and reducing conditions (data not shown). Deglycosylation of the immunoprecipitated human C-type lectin protein using neuraminidase and N-glycosidase treatment resulted in a size reduction of the main band to approximately 35 kD, indicating that at least some of the potential N-linked glycosilation sites were glycosylated in the expressed protein.

Example 10

Expression of the Human C-Type Lectin in AML

The expression of human C-type lectin in a large set of AML samples was analyzed by flow cytometry using the PE-conjugated anti-human C-type lectin antibody called 357. For this, primary AML samples were thawed and $2-4\times10^5$ cells were preincubated with 50 mg/ml rabbit IgG1 (DAKO) for 30 minutes on ice. Conjugated monoclonal antibodies were added and incubated with the cells for another 30 minutes. The following antibody combination was used: CD45-PerCP, anti-human C-type lectin-PE, CD33-APC. The cells were washed twice with PBS/1% BSA and resuspended in binding buffer for annexin V conjugates (Caltag) supplemented with annexin V-FITC for exclusion of dead and apoptotic cells. Cells were analyzed on a FACS calibur (BD) using CellQuest software. For final analysis, blasts cells were gated based on low side scatter versus CD45 expression. A sample was considered positive if more than 20% of the cells expressed the antigen of interest (compared to the control). The relative mean fluorescence intensity (MFI) was calculated by dividing the MFI of the specific antibody by the MFI of the isotype control sample.

As summarized in Table 4, the human C-type lectin antigen was expressed on more than 20% of blast cells in 92% of 74 AML samples and was effective for the detection of AML samples throughout the different FAB subtypes analyzed. The currently analyzed sample set included 12 CD33-negative AML samples of which 66.7% displayed human C-type lectin expression (see, Table 5). Of the samples negative for the human C-type lectin 33% (n=6) was reactive with the anti-CD33 antibody.

The analysis of the expression of the human C-type lectin on CD34+ stem cells within normal human bone marrow clearly showed that the antigen is not expressed on the CD34+ CD38– fraction which is thought to contain the non-committed stem cells with self-renewal capacity (see, Example 3). Upon acquisition of higher CD38 expression levels the CD34+ cells also gained expression of the human C-type lectin. The human C-type lectin+CD34+ cells co-expressed CD38 as well as CD33 (see, FIG. 4).

To further investigate the role of the human C-type lectin as a marker or therapeutic agent in AML, expression of the human C-type lectin in subpopulations of the AML samples was analyzed. Summarized, 69% of the AML samples were CD34+ (a sample was considered positive if more than 5% of the cells within the blast population expressed CD34). 96% of the CD34+ AML samples were positive for the human C-type lectin. 88% of the CD34+ AML samples contained a CD38-subpopulation and 90% of the CD34+CD38– cells were positive for the human C-type lectin. All CD34– AML samples were positive for the human C-type lectin. It is known that in AML positive for CD34, the CD34+CD38– subpopulation is responsible for the development of leukemia. As the human C-type lectin is expressed on the CD34+CD38– subpopulation in AML, but not on the CD34+CD38– fraction within normal human bone marrow, the human C-type lectin may function as a marker differentiating between leukemic and normal CD34+CD38– stem cells as well as have potential as a therapeutic agent for treatment of AML.

In AML having no CD34+CD38– fraction due to the absence of either CD34-positive cells and/or CD38-negative cells it is still unknown in which immunophenotypically defined subpopulation the leukemic stem cells can be found. In view of the above results the human C-type lectin may be a suitable marker and/or therapeutic agent for such AML cases.

Many patients with acute myeloid leukemia in complete remission will eventually relapse due to the persistence of minimal numbers of residual tumor cells-minimal residual disease (MRD). Currently, detection of MRD in patients with AML is based on the fact that leukemic cells frequently display aberrant phenotypic features that allow their distinction from normal cells. However, in MRD the CD34+CD38– subpopulation is difficult to detect due to its low frequency and, if detectable, distinction between leukemic and normal CD34+CD38– subpopulations is difficult to accomplish. In view thereof, the human C-type lectin might be a suitable marker for diagnosing and monitoring MRD and may be suitable as a tool to predict the outcome for patients with MRD. Additionally, the human C-type lectin may be suitable as a therapeutic agent in MRD.

Example 11

Density of the Human C-Type Lectin

Figure 17:
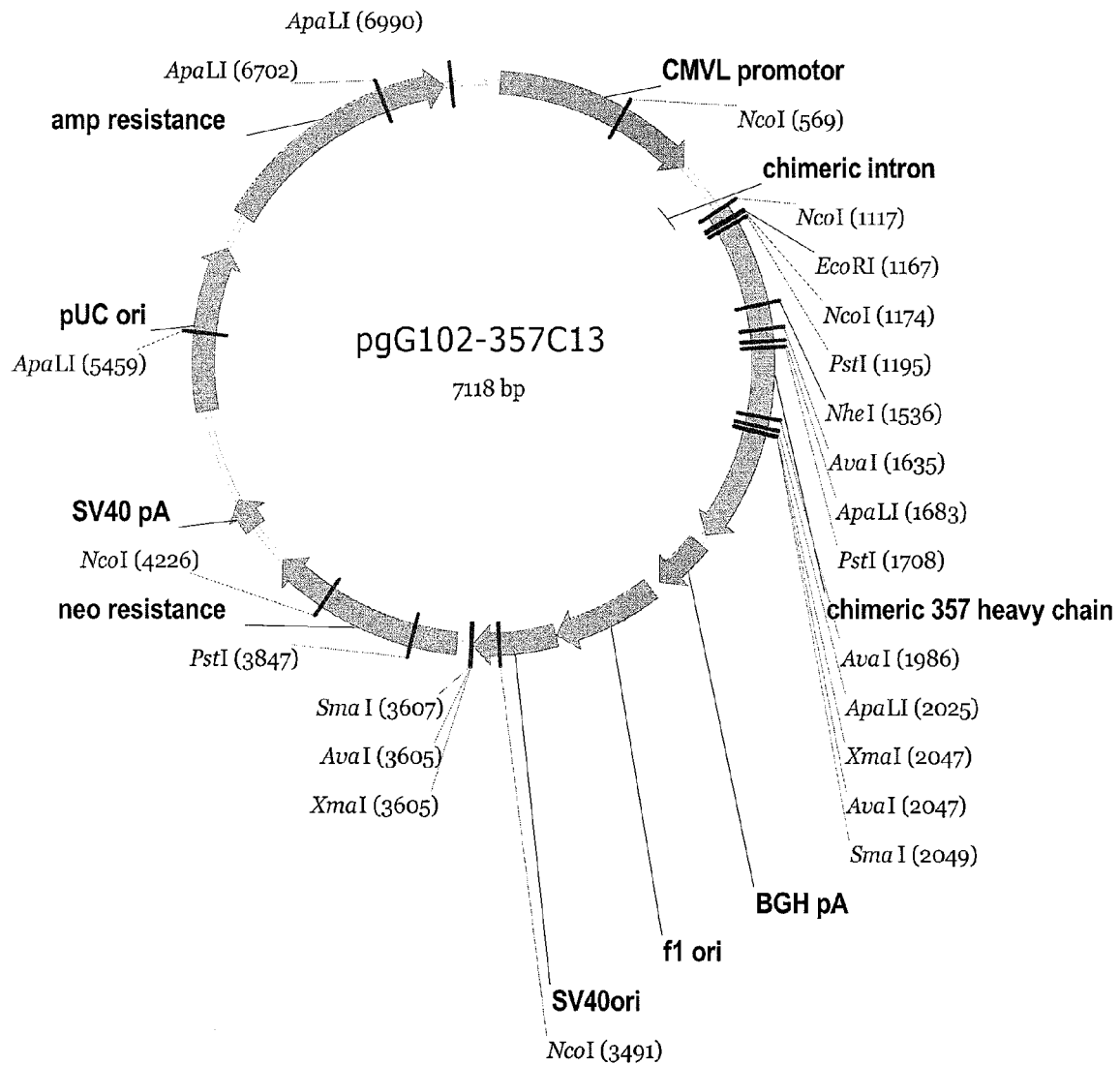
FIG. 17: The expression construct pgG102-357C13.

The cell surface density of the human C-type lectin was analyzed by quantitative flow cytometry (Qifikit, DAKO). To this purpose a chimeric anti-human C-type lectin antibody with a mouse IgG1 constant region was generated. A chimeric heavy chain expression vector was constructed by replacing the human CH2 and CH3 domains of pcDNA-SY-HC357 with the CH2 and CH3 domains of a mouse IgG1cDNA according to molecular biology techniques known to a skilled artisan. The nucleotide sequence and amino acid of the chimeric antibody 357 are shown in SEQ ID NOS:31 and 32, respectively. The resulting chimeric construct pcDNA-SY-HC357mouseCH2CH3 (see, FIG. 17 in which the construct is named pgG102-357C13) was transiently expressed in 293T cells in combination with the light chain encoding construct pcDNA-SY-Vκ1-Cκ and supernatants containing IgG1 antibodies were obtained and purified as described supra.

Cells to be analyzed were preincubated with 50 μg/ml rabbit IgG1 for 30 minutes on ice. Hereafter, saturating amounts of the purified chimeric anti-human C-type lectin antibody, a mouse IgG1 control antibody or a mouse CD33 antibody were used to stain myeloid leukemic cell lines, peripheral blood leukocytes or AML patient samples, followed by goat-anti-mouse-IgG FITC as a secondary reagent (DAKO). A set of microbeads having different calibrated densities of mouse IgG1 molecules on their surface was used for standarization prior to acquisition of the samples. The beads were incubated with the identical secondary reagent that was used on the patient samples. The beads and patient samples were measured on a FACScalibur flow cytometer and the data were analyzed using CellQuest software according to the Qifikit instructions.

Analysis of the density of the human C-type lectin antigen using this assay showed that approximately $6-17\times10^3$ human C-type lectin molecules per cell were present on the myeloid leukemic cell lines HL-60, U937 and THP-1, while peripheral blood monocytes and granulocytes expressed on average $10\times10^3$ and $4\times10^3$ molecules/cell, respectively (see, Table 6). Primary AML samples expressed on average $7\times10^3$ molecules/cell (n=27). No clear differences were observed in human C-type lectin expression in the different FAB subtypes analyzed. From the combined data of Tables 4 and 6, the expression levels of both the human C-type lectin and CD33 appear to be equal among the different FAB-subtypes with the exception of FAB M0 and M3. In the relatively undifferentiated M0 subtype the human C-type lectin expression appears to be higher as compared to CD33 while in the M3 subtype (acute promyelocytic leukemia) the opposite appears to be the case.

Example 12

Internalization of the Human C-Type Lectin

To analyze whether antibody-mediated cross-linking of the human C-type lectin on the cell surface could result in internalization of the antigen, in vitro studies were performed using myeloid leukemic cell lines. To this purpose, U937 cells were preincubated with 50 µg/ml rabbit IgG1 on ice for 30 minutes and were subsequently loaded with the phycoerythrin-labeled anti-human C-type lectin IgG1 antibody 357 or with a FITC-labeled anti-CD44 antibody (negative control). Unbound antibody was removed by two washes with ice-cold medium. Subsequently, aliquots of the cells were resuspended in 50 µl of medium and incubated at either 4° C. (no internalization) or 37° C. for different time points to allow internalization of the antibodies. Following three washes with ice-cold PBS, cell surface-bound antibodies were stripped off the cells using 50 µl Qiagen protease (Qiagen) at 7.5 AU/ml for one hour at 4° C. Cells were washed twice with ice-cold PBS-1% BSA and samples were analyzed by flow cytometry. The fluorescence at t=0 in the absence of protease treatment was normalized to 100%.

Figure 18:
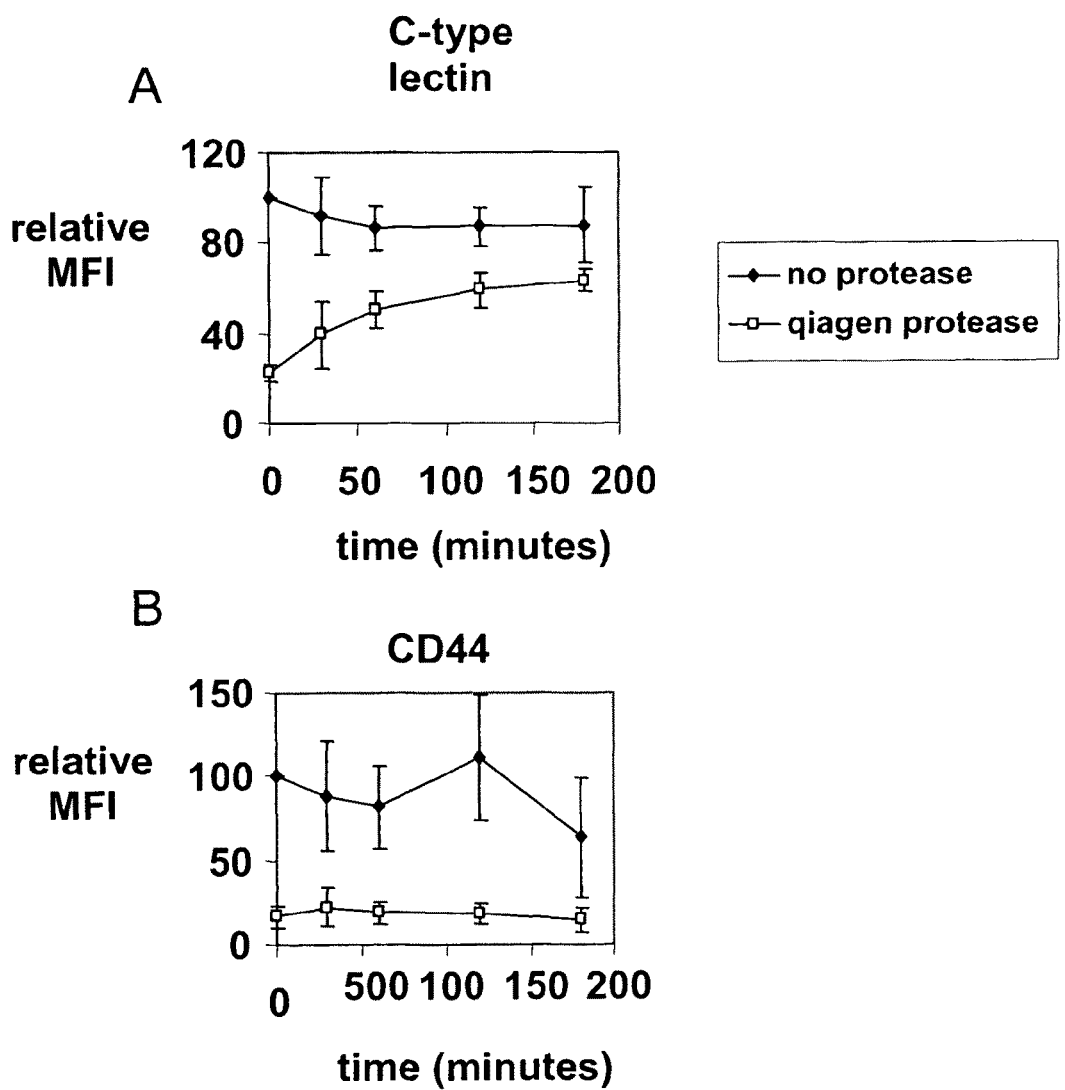
FIG. 18: Analysis of internalization of the anti-human C-type lectin antibody 357 (FIG. 18A) and an anti-CD44 antibody (FIG. 18B). On the Y-axis, the relative mean fluorescence intensity is shown and, on the X-axis, the incubation time in minutes is shown.

Antibody binding assays at 37° C. showed that the fluorescent labeled anti-human C-type lectin antibody 357 became associated with U937 cells over time in a protease resistant compartment, i.e., not on the cell surface (see, FIG. 18A). After three hours of incubation approximately 50% of the fluorescent anti-human C-type lectin antibody was internalized, while a control antibody that recognized CD44 remained protease sensitive during this period (see, FIG. 18B).

Table 1: Nucleotide and amino acid sequence of the scFvs and VH and VL gene identity.

TABLE 2

Analysis of tumor cell lines of hematopoetic and non-hematopoetic origin for reactivity with SC02-357.

| Cell line | Origin | SC02-357 reactivity |
|---|---|---|
| KG1 | Acute Myeloid Leukemia | − |
| HL-60 | Acute Myeloid Leukemia | + |
| NB4 | Acute Promyelocytic Leukemia | − |
| U937 | Histiocytic Lymphoma | + |
| THP-1 | Acute Monocytic Leukemia | + |
| K562 | Erythroid Leukemia | − |
| 293T | Embryonal Kidney | − |
| PerC6 | Embryonal Retina | − |
| LS174T | Colon Adenocarcinoma | − |

TABLE 3

Analysis of expression of human C-type lectin in human tissues.

| Tissue | Human C-type lectin | CD46 (positive control) |
|---|---|---|
| Adrenal gland | − | + |
| Aorta | − | + |
| Bladder | − | + |
| Cerebellum | − | + |
| Cerebrum | − | + |
| Cervix | − | + |
| Colon | − | + |
| Coronary artery | − | + |
| Duodenum | − | + |
| Endometrium | − | + |
| Esophagus | − | + |
| Fallopian tube | − | + |
| Heart | − | + |
| Ileum | − | + |
| Kidney | − | + |
| Liver | − | + |
| Lung | − | + |
| Lymph node | − | + |
| Ovary | − | + |
| Pancreas | − | + |
| Parathyroid | − | + |
| Peripheral nerve | − | + |
| Pituitary gland | − | + |
| Placenta | − | + |
| Prostate | − | + |
| Salivary gland | − | + |
| Skin | − | + |
| Spinal cord | − | + |
| Spleen | ±* | + |
| Stomach | − | + |
| Testis | − | + |
| Thyroid | − | + |

TABLE 1

Nucleotide and amino acid sequence of the scFvs and VH and VL gene identity.

| scFv | SEQ ID NO of nucleotide sequence | SEQ ID NO of amino acid sequence | CDR3 | VH-germline | VL-germline |
|---|---|---|---|---|---|
| SC02-357 | SEQ ID NO:14 | SEQ ID NO: 15 | VSTGGFFDY (SEQ ID NO: 3) | VH4 DP69 | VKI |
| SC02-378 | SEQ ID NO: 16 | SEQ ID NO: 17 | SSSGGFFDY (SEQ ID NO: 4) | VH4 DP69 | VKI |
| SC02-161 | SEQ ID NO: 18 | SEQ ID NO: 19 | QTTAGSFDY (SEQ ID NO: 5) | VH4 DP69 | VKI |

TABLE 3-continued

Analysis of expression of human C-type lectin in human tissues.

| Tissue | Human C-type lectin | CD46 (positive control) |
|---|---|---|
| Tonsil | − | + |
| Ureter | − | + |

*Scattered human C-type lectin+ granulocytes were observed

TABLE 4

Flow cytometry analysis of expression of human C-type lectin in AML samples.

| | Human C-type lectin | | | CD33 | | |
|---|---|---|---|---|---|---|
| FAB | % positive cases | % positive blasts$ | relative MFI§ | % positive cases | % positive blasts | relative MFI |
| M0 | 75.0 (3#/4*) | 95.0 ± 7.5 | 48.8 ± 35.7 | 75/0 (3/4) | 79.8 ± 20.5 | 9.3 ± 7.0 |
| M1 | 81.8 (9/11) | 80.1 ± 17.9 | 24.6 ± 14.2 | 81.8 (9/11) | 65.9 ± 29.9 | 31.0 ± 37.8 |
| M2 | 91.7 (11/12) | 73.5 ± 17.8 | 24.9 ± 19.1 | 83.3 (10/12) | 78.3 ± 27.6 | 34.9 ± 53.8 |
| M3 | 100 (2/2) | 86.4 | 14.4 | 100 (2/2) | 99.9 | 97.9 |
| M4 | 100 (8/8) | 80.3 ± 23.6 | 74.1 ± 47.0 | 100 (8/8) | 80.1 ± 22.9 | 63.9 ± 77.8 |
| M4eo | 100 (2/2) | 66.4 | 18.2 | 100 (2/2) | 84.5 | 24.7 |
| M5 | 100 (9/9) | 81.7 ± 20.7 | 74.1 ± 68.1 | 88.9 (8/9) | 96.8 ± 4.4 | 51.9 ± 85.2 |
| M5a | 100 (8/8) | 83.3 ± 21.2 | 29.8 ± 15.8 | 100 (8/8) | 71.9 ± 33.7 | 15.9 ± 7.8 |
| M5b | 100 (5/5) | 89.8 ± 8.0 | 52.8 ± 22.2 | 100 (5/5) | 96.1 ± 4.5 | 34.6 ± 9.9 |
| M6 | 66.7 (2/3) | 66.7 | 35.6 | 66.7 (2/3) | 92.9 | 91.8 |
| raeb | 100 (2/2) | 40.6 | 21.1 | 0 (0/2) | NA | NA |
| Unclassified | 87.5 (7/8) | 76.3 ± 27.6 | 33.2 ± 18.2 | 62.5 (5/8) | 73.6 ± 25.9 | 99.8 ± 178.2 |
| total AML | 91.9 (68/74) | 74.4 ± 27.2 | 39.4 ± 37.7 | 83.7 (62/74) | 81.4 ± 24.3 | 50.5 ± 72.6 | number of positive cases; a sample was considered positive if more than 20% of the blast population stained with the anti-human C-type lectin antibody or anti-CD33 antibody.
*number of cases tested.
$average ± SD of % blast cells in positive samples.
§MFI of positive blasts cells divided by MFI control sample.

TABLE 5

Further analysis of CD33-positive and -negative and human C-type lectin-positive and -negative samples.

| AML | CD33+ | CD33− | Total amount |
|---|---|---|---|
| Human C-type lectin+ | 60 | 8 | 68 |
| Human C-type lectin− | 2 | 4 | 6 |
| Total amount | 62 | 12 | 74 |

+positive
−negative

TABLE 6

Analysis of density of human C-type lectin and CD33 on different cell types.

| | Human C-type lectin | | CD33 | |
|---|---|---|---|---|
| cell type | n | antigen density* | n | antigen density* |
| AML M0 | 1 | 4143 | 1 | 1457 |
| AML M1 | 4 | 3753 ± 2179 | 4 | 5352 ± 5113 |
| AML M2 | 4 | 5234 ± 3871 | 4 | 2822 ± 1023 |
| AML M3 | 1 | 6130 | 1 | 28413 |
| AML M4 | 5 | 8887 ± 2503 | 5 | 5655 ± 2427 |
| AML M5 | 4 | 11092 ± 3913 | 4 | 9794 ± 5559 |
| AML M5a | 3 | 7842 ± 4363 | 2 | 9016 |
| AML M5b | 1 | 10188 | 1 | 6531 |
| AML unclassified | 4 | 8384 ± 3651 | 4 | 11361 ± 12863 |
| AML total | 27 | 7491 ± 3773 | 26 | 7148 ± 6332 |
| HL60 | 4 | 6041 ± 3239 | 2 | 32549 |
| U937 | 4 | 17314 ± 3292 | 2 | 20110 |

TABLE 6-continued

Analysis of density of human C-type lectin and CD33 on different cell types.

| cell type | Human C-type lectin | | CD33 | |
|---|---|---|---|---|
| | n | antigen density* | n | antigen density* |
| THP1 | 2 | 5926 | 1 | 57990 |
| monocytes | 2 | 9874 | 2 | 8127 |
| granulocytes | 2 | 4305 | 2 | 1313 |

*Mean number of molecules per cell ± SD

REFERENCES

Aruffo A. and B. Seed (1987), Molecular cloning of a CD28 cDNA by a high-efficiency COS cell expression system. *Proc. Natl. Acad. Sci. USA* 84:8573-8577.

Boel E., S. Verlaan, M. J. Poppelier, N. A. Westerdaal, J. A. Van Strijp and T. Logtenberg (2000), Functional human monoclonal antibodies of all isotypes constructed from phage display library-derived single-chain Fv antibody fragments. *J. Immunol. Methods* 239:153-166.

Burton D. R. and C. F. Barbas (1994), Human antibodies from combinatorial libraries. *Adv. Immunol.* 57:191-280.

Chuang E., M. L. Alegre, C. S. Duckett, P. J. Noel, M. G. Van der Heiden and C. B. Thompson (1997), Interaction of CTLA-4 with the clathrin-associated protein AP50 results in ligand-independent endocytosis that limits cell surface expression. *J. Immunol.* 159:144-151.

Colonna M., J. Samaridis and L. Angman (2000), Molecular characterization of two novel C-type lectin-like receptors, one of which is selectively expressed in human dendritic cells. *Eur. J. Immunol.* 30:697-704.

De Kruif J., L. Terstappen, E. Boel and T. Logtenberg (1995a), Rapid selection of cell subpopulation-specific human monoclonal antibodies from a synthetic phage antibody library. *Proc. Natl. Acad. Sci. USA* 92:3938.

De Kruif J., E. Boel and T. Logtenberg (1995b), Selection and application of human single chain Fv antibody fragments from a semi-synthetic phage antibody display library with designed CDR3 regions. *J. Mol. Biol.* 248:97.

Hamann P. R., L. M. Hinman, I. Hollander, C. F. Beyer, D. Lindh, R. Holcomb, W. Hallett, H. R. Tsou, J. Upeslacis, D. Shochat, A. Mountain, D. A. Flowers and I. Bernstein (2002), Gemtuzumab ozogamicin, a potent and selective anti-CD33 antibody-calicheamicin conjugate for treatment of acute myeloid leukemia. *Bioconjug. Chem.* 13:47-58.

Huls G., I. J. Heijnen, E. Cuomo, J. van der Linden, E. Boel, J. van de Winkel and T. Logtenberg (1999), Antitumor immune effector mechanisms recruited by phage display-derived fully human IgG1 and IgA1 monoclonal antibodies. *Cancer Res.* 59:5778-5784.

Lanier L. L., C. Chang and J. H. Phillips (1994), Human NKR-P1A. A disulfide-linked homodimer of the C-type lectin superfamily expressed by a subset of NK and T lymphocytes. *J. Immunol.* 153:2417-2428.

Wu H., D. A. Windmiller, L. Wang and J. M. Backer (2003), YXXM motifs in the PDGF-beta receptor serve dual roles as phosphoinositide 3-kinase binding motifs and tyrosine-based endocytic sorting signals. *J. Biol. Chem.* 278:40425-40428.

---

What is claimed is:

1. An isolated human C-type lectin protein comprising the amino acid sequence of SEQ ID NO: 2.

2. A recombinant human C-type lectin protein comprising the amino acid sequence of SEQ ID NO:2.

3. A composition comprising: the human C-type lectin protein of claim 1, and at least one pharmaceutically acceptable excipient.

* * * * *

SEQUENCE LISTING

```
<160> NUMBER OF SEQ ID NOS: 44

<210> SEQ ID NO 1
<211> LENGTH: 1492
<212> TYPE: DNA
<213> ORGANISM: Homo sapiens
<220> FEATURE:
<221> NAME/KEY: CDS
<222> LOCATION: (32)..(859)
<223> OTHER INFORMATION: human c-type lectin

<400> SEQUENCE: 1
ggaagaacag cctttcaaat ttgacttctg c atg tgg ata gat ttc ttt aca        52
                                   Met Trp Ile Asp Phe Phe Thr
                                   1               5 tat tca tca atg tct gaa gaa gtt act tat gca gat ctt caa ttc cag      100
Tyr Ser Ser Met Ser Glu Glu Val Thr Tyr Ala Asp Leu Gln Phe Gln
        10                  15                  20 aac tcc agt gag atg gaa aaa atc cca gaa att ggc aaa ttt ggg gaa      148
Asn Ser Ser Glu Met Glu Lys Ile Pro Glu Ile Gly Lys Phe Gly Glu
    25                  30                  35 aaa gca cct cca gct ccc tct cat gta tgg cgt cca gca gcc ttg ttt      196
Lys Ala Pro Pro Ala Pro Ser His Val Trp Arg Pro Ala Ala Leu Phe
40                  45                  50                  55 ctg act ctt ctg tgc ctt ctg ttg ctc att gga ttg gga gtc ttg gca      244
Leu Thr Leu Leu Cys Leu Leu Leu Leu Ile Gly Leu Gly Val Leu Ala
                60                  65                  70 agc atg ttt cac gta act ttg aag ata gaa atg aaa aaa atg aac aaa      292
Ser Met Phe His Val Thr Leu Lys Ile Glu Met Lys Lys Met Asn Lys
            75                  80                  85
```

| | | | | | | | | | | | | | |
|---|---|---|---|---|---|---|---|---|---|---|---|---|---|
| cta | caa | aac | atc | agt | gaa | gag | ctc | cag | aga | aat | att | tct | cta | caa | ctg | 340 |
| Leu | Gln | Asn | Ile | Ser | Glu | Glu | Leu | Gln | Arg | Asn | Ile | Ser | Leu | Gln | Leu |
| | | | 90 | | | | 95 | | | | 100 | | | | |
| atg | agt | aac | atg | aat | atc | tcc | aac | aag | atc | agg | aac | ctc | tcc | acc | aca | 388 |
| Met | Ser | Asn | Met | Asn | Ile | Ser | Asn | Lys | Ile | Arg | Asn | Leu | Ser | Thr | Thr |
| 105 | | | | | 110 | | | | | 115 | | | | | |
| ctg | caa | aca | ata | gcc | acc | aaa | tta | tgt | cgt | gag | cta | tat | agc | aaa | gaa | 436 |
| Leu | Gln | Thr | Ile | Ala | Thr | Lys | Leu | Cys | Arg | Glu | Leu | Tyr | Ser | Lys | Glu |
| 120 | | | | | 125 | | | | | 130 | | | | | 135 |
| caa | gag | cac | aaa | tgt | aag | cct | tgt | cca | agg | aga | tgg | att | tgg | cat | aag | 484 |
| Gln | Glu | His | Lys | Cys | Lys | Pro | Cys | Pro | Arg | Arg | Trp | Ile | Trp | His | Lys |
| | | | | 140 | | | | | 145 | | | | | 150 | |
| gac | agc | tgt | tat | ttc | cta | agt | gat | gat | gtc | caa | aca | tgg | cag | gag | agt | 532 |
| Asp | Ser | Cys | Tyr | Phe | Leu | Ser | Asp | Asp | Val | Gln | Thr | Trp | Gln | Glu | Ser |
| | | | 155 | | | | | 160 | | | | | 165 | | |
| aaa | atg | gcc | tgt | gct | gct | cag | aat | gcc | agc | ctg | ttg | aag | ata | aac | aac | 580 |
| Lys | Met | Ala | Cys | Ala | Ala | Gln | Asn | Ala | Ser | Leu | Leu | Lys | Ile | Asn | Asn |
| | | 170 | | | | | 175 | | | | | 180 | | | |
| aaa | aat | gca | ttg | gaa | ttt | ata | aaa | tcc | cag | agt | aga | tca | tat | gac | tat | 628 |
| Lys | Asn | Ala | Leu | Glu | Phe | Ile | Lys | Ser | Gln | Ser | Arg | Ser | Tyr | Asp | Tyr |
| | 185 | | | | | 190 | | | | | 195 | | | | |
| tgg | ctg | gga | tta | tct | cct | gaa | gaa | gat | tcc | act | cgt | ggt | atg | aga | gtg | 676 |
| Trp | Leu | Gly | Leu | Ser | Pro | Glu | Glu | Asp | Ser | Thr | Arg | Gly | Met | Arg | Val |
| 200 | | | | | 205 | | | | | 210 | | | | | 215 |
| gat | aat | ata | atc | aac | tcc | tct | gcc | tgg | gtt | ata | aga | aac | gca | cct | gac | 724 |
| Asp | Asn | Ile | Ile | Asn | Ser | Ser | Ala | Trp | Val | Ile | Arg | Asn | Ala | Pro | Asp |
| | | | | 220 | | | | | 225 | | | | | 230 | |
| tta | aat | aac | atg | tat | tgt | gga | tat | ata | aat | aga | cta | tat | gtt | caa | tat | 772 |
| Leu | Asn | Asn | Met | Tyr | Cys | Gly | Tyr | Ile | Asn | Arg | Leu | Tyr | Val | Gln | Tyr |
| | | | 235 | | | | | 240 | | | | | 245 | | |
| tat | cac | tgc | act | tat | aaa | aaa | aga | atg | ata | tgt | gag | aag | atg | gcc | aat | 820 |
| Tyr | His | Cys | Thr | Tyr | Lys | Lys | Arg | Met | Ile | Cys | Glu | Lys | Met | Ala | Asn |
| | | 250 | | | | | 255 | | | | | 260 | | | |
| cca | gtg | cag | ctt | ggt | tct | aca | tat | ttt | agg | gag | gca | tga | ggcatcaatc | | | 869 |
| Pro | Val | Gln | Leu | Gly | Ser | Thr | Tyr | Phe | Arg | Glu | Ala | | | | |
| | 265 | | | | | 270 | | | | | 275 | | | | |

| | | |
|---|---|---|
| aaatacattt aaggagtgta gggggtgggg gttctaggct ataggtaaat ttaaatattt | 929 |
| tctggttgac aattagttga gtttgtctga agacctggga ttttatcatg cagatgaaac | 989 |
| atccaggtag caagcttcag agagaataga ctgtgaatgt taatgccaga gaggtataat | 1049 |
| gaagcatgtc ccacctccca ctttccatca tggcctgaac cctggaggaa gaggaagtcc | 1109 |
| attcagatag ttgtgggggg ccttcgaatt ttcatttca tttacgttct tccccttctg | 1169 |
| gccaagattt gccagaggca acatcaaaaa ccagcaaatt ttaattttgt cccacagcgt | 1229 |
| tgctagggtg gcatggctcc ccatctcggg tccatcctat acttccatgg gactccctat | 1289 |
| ggctgaaggc cttatgagtc aaaggactta tagccaattg attgttctag gccaggtaag | 1349 |
| aatggatatg gacatgcatt tattacctct taaaattatt attttaagta aaagccaata | 1409 |
| aacaaaaacg aaaaggcaaa aaaaaaaaaa aaaaaaaaaa aaaaaaaaaa aaaaaaaaaa | 1469 |
| aaaaaaaaaa aaaaaaaaaa aaa | 1492 |

<210> SEQ ID NO 2
<211> LENGTH: 275
<212> TYPE: PRT
<213> ORGANISM: Homo sapiens

<400> SEQUENCE: 2

Met Trp Ile Asp Phe Phe Thr Tyr Ser Ser Met Ser Glu Glu Val Thr

-continued

```
                1               5                  10                 15
Tyr Ala Asp Leu Gln Phe Gln Asn Ser Ser Glu Met Glu Lys Ile Pro
                    20                  25                  30

Glu Ile Gly Lys Phe Gly Glu Lys Ala Pro Pro Ala Pro Ser His Val
                    35                  40                  45

Trp Arg Pro Ala Ala Leu Phe Leu Thr Leu Leu Cys Leu Leu Leu Leu
50                  55                  60

Ile Gly Leu Gly Val Leu Ala Ser Met Phe His Val Thr Leu Lys Ile
65                  70                  75                  80

Glu Met Lys Lys Met Asn Lys Leu Gln Asn Ile Ser Glu Glu Leu Gln
                    85                  90                  95

Arg Asn Ile Ser Leu Gln Leu Met Ser Asn Met Asn Ile Ser Asn Lys
                    100                 105                 110

Ile Arg Asn Leu Ser Thr Thr Leu Gln Thr Ile Ala Thr Lys Leu Cys
                    115                 120                 125

Arg Glu Leu Tyr Ser Lys Glu Gln Glu His Lys Cys Lys Pro Cys Pro
                    130                 135                 140

Arg Arg Trp Ile Trp His Lys Asp Ser Cys Tyr Phe Leu Ser Asp Asp
145                 150                 155                 160

Val Gln Thr Trp Gln Glu Ser Lys Met Ala Cys Ala Ala Gln Asn Ala
                    165                 170                 175

Ser Leu Leu Lys Ile Asn Asn Lys Asn Ala Leu Glu Phe Ile Lys Ser
                    180                 185                 190

Gln Ser Arg Ser Tyr Asp Tyr Trp Leu Gly Leu Ser Pro Glu Glu Asp
                    195                 200                 205

Ser Thr Arg Gly Met Arg Val Asp Asn Ile Ile Asn Ser Ser Ala Trp
210                 215                 220

Val Ile Arg Asn Ala Pro Asp Leu Asn Asn Met Tyr Cys Gly Tyr Ile
225                 230                 235                 240

Asn Arg Leu Tyr Val Gln Tyr Tyr His Cys Thr Tyr Lys Lys Arg Met
                    245                 250                 255

Ile Cys Glu Lys Met Ala Asn Pro Val Gln Leu Gly Ser Thr Tyr Phe
                    260                 265                 270

Arg Glu Ala
        275

<210> SEQ ID NO 3
<211> LENGTH: 9
<212> TYPE: PRT
<213> ORGANISM: Artificial sequence
<220> FEATURE:
<223> OTHER INFORMATION: CDR3 of SC02-357, synthetic

<400> SEQUENCE: 3

Val Ser Thr Gly Gly Phe Phe Asp Tyr
1               5

<210> SEQ ID NO 4
<211> LENGTH: 9
<212> TYPE: PRT
<213> ORGANISM: Artificial sequence
<220> FEATURE:
<223> OTHER INFORMATION: CDR3 of SC02-378, synthetic

<400> SEQUENCE: 4

Ser Ser Ser Gly Gly Phe Phe Asp Tyr
1               5
```

-continued

```
<210> SEQ ID NO 5
<211> LENGTH: 9
<212> TYPE: PRT
<213> ORGANISM: Artificial sequence
<220> FEATURE:
<223> OTHER INFORMATION: CDR3 of SC02-161, synthetic

<400> SEQUENCE: 5

Gln Thr Thr Ala Gly Ser Phe Asp Tyr
1               5

<210> SEQ ID NO 6
<211> LENGTH: 1410
<212> TYPE: DNA
<213> ORGANISM: Artificial sequence
<220> FEATURE:
<223> OTHER INFORMATION: Nucleotide sequence of heavy chain of 357,
      synthetic

<400> SEQUENCE: 6
atggcctgcc ccggcttcct gtgggccctg gtgatcagca cctgcctgga attctccatg      60
gcccaggtgc agctgcagga gtccggccca ggactggtga agccttcgga ccctgtcc      120 ctcacctgcg ttgtctctgg tggctccatc agcagtagta ctggtggag ctgggtccgc     180 cagcccccag ggaaggggct ggagtggatt gggaaatct atcatagtgg gagccccgac     240
tacaacccgt ccctcaagag tcgagtcacc atatcagtag acaagtccag gaaccagttc     300
tccctgaagc tgagctctgt gaccgccgcg gacacggccg tgtattactg caaaggtt      360 agtactggtg gtttctttga ctactggggc cagggcaccc tggtgaccgt ctccagcgct     420
agcaccaagg gcccagcgt gttccccctg gccccagca gcaagagcac cagcggcggc      480
acagccgccc tgggctgcct ggtgaaggac tacttcccg agcccgtgac cgtgagctgg     540
aacagcggcg ccttgaccag cggcgtgcac accttcccg ccgtgctgca gagcagcggc     600
ctgtacagcc tgagcagcgt ggtgaccgtg cccagcagca gctgggcac ccagacctac     660 atctgcaacg tgaaccacaa gcccagcaac accaaggtgg acaaacgcgt ggagcccaag     720
agctgcgaca gacccacac ctgccccccc tgccctgccc cgagctgct gggcggaccc      780 tccgtgttcc tgttcccccc caagcccaag gacaccctca tgatcagccg gaccccgag      840 gtgacctgcg tggtggtgga cgtgagccac gaggacccg aggtgaagtt caactggtac     900
gtggacggcg tggaggtgca caacgccaag accaagcccc gggaggagca gtacaacagc     960
acctaccggg tggtgagcgt gctcaccgtg ctgcaccagg actggctgaa cggcaaggag    1020
tacaagtgca aggtgagcaa caaggccctg cctgccccca tcgagaagac catcagcaag    1080
gccaagggcc agccccggga gccccaggtg tacaccctgc ccccagccg ggaggagatg     1140 accaagaacc aggtgtccct cacctgtctg gtgaagggct ctacccag cgacatcgcc     1200 gtggagtggg agagcaacgg ccagcccgag aacaactaca agaccacccc cctgtgctg     1260 gacagcgacg gcagcttctt cctgtacagc aagctcaccg tggacaagag ccggtggcag    1320
cagggcaacg tgttcagctg cagcgtgatg cacgaggccc tgcacaacca ctacacccag    1380
aagagcctga gcctgagccc cggcaagtga                                     1410

<210> SEQ ID NO 7
<211> LENGTH: 448
<212> TYPE: PRT
<213> ORGANISM: Artificial sequence
<220> FEATURE:
<223> OTHER INFORMATION: Amino acid sequence of heavy chain of 357,
      synthetic
```

```
<400> SEQUENCE: 7

Gln Val Gln Leu Gln Glu Ser Gly Pro Gly Leu Val Lys Pro Ser Glu
  1               5                  10                  15

Thr Leu Ser Leu Thr Cys Val Val Ser Gly Gly Ser Ile Ser Ser Ser
             20                  25                  30

Asn Trp Trp Ser Trp Val Arg Gln Pro Pro Gly Lys Gly Leu Glu Trp
         35                  40                  45

Ile Gly Glu Ile Tyr His Ser Gly Ser Pro Asp Tyr Asn Pro Ser Leu
 50                  55                  60

Lys Ser Arg Val Thr Ile Ser Val Asp Lys Ser Arg Asn Gln Phe Ser
 65                  70                  75                  80

Leu Lys Leu Ser Ser Val Thr Ala Ala Asp Thr Ala Val Tyr Tyr Cys
             85                  90                  95

Ala Lys Val Ser Thr Gly Gly Phe Phe Asp Tyr Trp Gly Gln Gly Thr
            100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
            290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
            355                 360                 365

Leu Val Lys Gly Phe Tyr Pro Ser Asp Ile Ala Val Glu Trp Glu Ser
370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415
```

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
        435                 440                 445

<210> SEQ ID NO 8
<211> LENGTH: 1410
<212> TYPE: DNA
<213> ORGANISM: Artificial sequence
<220> FEATURE:
<223> OTHER INFORMATION: Nucleotide sequence of heavy chain of 378,
      synthetic

<400> SEQUENCE: 8

| | |
|---|---|
| atggcctgcc ccggcttcct gtgggccctg gtgatcagca cctgcctgga attctccatg | 60 |
| gcccaggtgc agctgcagga gtccggccca ggactggtga agccttcgga gaccctgtcc | 120 |
| ctcacctgcg ttgtctctgg tggctccatc agcagtagta actggtggag ctgggtccgc | 180 |
| cagcccccag ggaaggggct ggagtggatt ggggaaatct atcatagtgg gagccccaac | 240 |
| tacaacccgt ccctcaagag tcgagtcacc atatcagtag acaagtccaa gaaccagttc | 300 |
| tccctgaagc tgagctctgt gaccgccgcg gacacggccg tgtattactg tgcaaggtcg | 360 |
| tcttctggtg gtttctttga ctactggggc cagggcaccc tggtgaccgt ctccagcgct | 420 |
| agcaccaagg gcccagcgt gttccccctg gcccccagca gcaagagcac cagcggcggc | 480 |
| acagccgccc tgggctgcct ggtgaaggac tacttccccg agcccgtgac cgtgagctgg | 540 |
| aacagcggcg ccttgaccag cggcgtgcac accttccccg ccgtgctgca gagcagcggc | 600 |
| ctgtacagcc tgagcagcgt ggtgaccgtg cccagcagca gcctgggcac ccagacctac | 660 |
| atctgcaacg tgaaccacaa gcccagcaac accaaggtgg acaaacgcgt ggagcccaag | 720 |
| agctgcgaca agacccacac ctgcccccc tgccctgccc ccgagctgct gggcggaccc | 780 |
| tccgtgttcc tgttcccccc caagcccaag gacaccctca tgatcagccg gacccccgag | 840 |
| gtgacctgcg tggtggtgga cgtgagccac gaggaccccg aggtgaagtt caactggtac | 900 |
| gtggacggcg tggaggtgca caacgccaag accaagcccc gggaggagca gtacaacagc | 960 |
| acctaccggg tggtgagcgt gctcaccgtg ctgcaccagg actggctgaa cggcaaggag | 1020 |
| tacaagtgca aggtgagcaa caaggccctg cctgccccca tcgagaagac catcagcaag | 1080 |
| gccaagggcc agccccggga gccccaggtg tacaccctgc ccccagccg ggaggagatg | 1140 |
| accaagaacc aggtgtccct cacctgtctg gtgaagggct tctacccag cgacatcgcc | 1200 |
| gtggagtggg agagcaacgg ccagcccgag aacaactaca agaccacccc cctgtgctg | 1260 |
| gacagcgacg gcagcttctt cctgtacagc aagctcaccg tggacaagag ccggtggcag | 1320 |
| cagggcaacg tgttcagctg cagcgtgatg cacgaggccc tgcacaacca ctacacccag | 1380 |
| aagagcctga gcctgagccc cggcaagtga | 1410 |

<210> SEQ ID NO 9
<211> LENGTH: 448
<212> TYPE: PRT
<213> ORGANISM: Artificial sequence
<220> FEATURE:
<223> OTHER INFORMATION: Amino acid sequence of heavy chain of 378,
      synthetic

<400> SEQUENCE: 9

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser

-continued

```
             20                  25                  30
Asn Trp Trp Ser Trp Val Arg Gln Pro Pro Gly Lys Gly Leu Glu Trp
             35                  40                  45
Ile Gly Glu Ile Tyr His Ser Gly Ser Pro Asn Tyr Asn Pro Ser Leu
 50                  55                  60
Lys Ser Arg Val Thr Ile Ser Val Asp Lys Ser Lys Asn Gln Phe Ser
 65                  70                  75                  80
Leu Lys Leu Ser Ser Val Thr Ala Ala Asp Thr Ala Val Tyr Tyr Cys
                 85                  90                  95
Ala Arg Ser Ser Ser Gly Gly Phe Phe Asp Tyr Trp Gly Gln Gly Thr
                100                 105                 110
Leu Val Thr Val Ser Ser Ala Ser Thr Lys Gly Pro Ser Val Phe Pro
            115                 120                 125
Leu Ala Pro Ser Ser Lys Ser Thr Ser Gly Gly Thr Ala Ala Leu Gly
        130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Arg Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Glu Glu Met Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 10
<211> LENGTH: 1410
<212> TYPE: DNA
<213> ORGANISM: Artificial sequence
<220> FEATURE:
<223> OTHER INFORMATION: Nucleotide sequence of heavy chain of 161, synthetic

<400> SEQUENCE: 10

```
atggcctgcc ccggcttcct gtgggccctg gtgatcagca cctgcctgga attctccatg      60
gcccaggtgc agctgcagga gtccggccca ggactggtga agccttcgga gaccctgtcc     120
ctcacctgcg ttgtctctgg tggctccatc agcagtagta ctggtggag ctgggtccgc      180
cagcccccag ggaaggggct ggagtggatt ggggaaatct atcatagtgg gagccccaac     240
tacaacccgt ccctcaagag tcgagtcacc atatcagtag acaagtccaa gaaccagttc     300
tccctgaagc tgagctctgt gaccgccgcg gacacggccg tgtattactg tgcaaggcag     360
actactgctg gtcctttga ctactggggc cagggcaccc tggtgaccgt ctccagcgct      420
agcaccaagg gcccagcgt gttccccctg gcccccagca gcaagagcac cagcggcggc      480
acagccgccc tgggctgcct ggtgaaggac tacttccccg agcccgtgac cgtgagctgg     540
aacagcggcg ccttgaccag cggcgtgcac accttccccg ccgtgctgca gagcagcggc     600
ctgtacagcc tgagcagcgt ggtgaccgtg cccagcagca gcctgggcac ccagacctac     660
atctgcaacg tgaaccacaa gcccagcaac accaaggtgg acaaacgcgt ggagcccaag     720
agctgcgaca gacccacac ctgccccccc tgccctgccc ccgagctgct gggcggaccc      780
tccgtgttcc tgttccccc caagcccaag gacacccctca tgatcagccg accccccgag    840
gtgacctgcg tggtggtgga cgtgagccac gaggacccc aggtgaagtt caactggtac      900
gtggacggcg tggaggtgca caacgccaag accaagcccc gggaggagca gtacaacagc     960
acctaccggg tggtgagcgt gctcaccgtg ctgcaccagg actggctgaa cggcaaggag    1020
tacaagtgca aggtgagcaa caaggccctg cctgccccca tcgagaagac catcagcaag    1080
gccaagggcc agccccggga gccccaggtg tacaccctgc cccccagccg ggaggagatg    1140
accaagaacc aggtgtccct cacctgtctg gtgaagggct tctacccag cgacatcgcc    1200
gtggagtggg agagcaacgg ccagcccgag aacaactaca agaccacccc cctgtgctg     1260
gacagcgacg gcagcttctt cctgtacagc aagctcaccg tggacaagag ccggtggcag    1320
cagggcaacg tgttcagctg cagcgtgatg cacgaggccc tgcacaacca ctacacccag    1380
aagagcctga gcctgagccc cggcaagtga                                     1410
```

<210> SEQ ID NO 11
<211> LENGTH: 448
<212> TYPE: PRT
<213> ORGANISM: Artificial sequence
<220> FEATURE:
<223> OTHER INFORMATION: Amino acid sequence of heavy chain of 161, synthetic

<400> SEQUENCE: 11

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asn Tyr Asn Pro Ser Leu

```
            50                  55                  60
Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                 85                  90                  95

Ala Arg Gln Thr Thr Ala Gly Ser Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Arg Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Glu Glu Met Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 12
<211> LENGTH: 708
<212> TYPE: DNA
<213> ORGANISM: Artificial sequence
<220> FEATURE:
```

```
<223> OTHER INFORMATION: Nucleotide sequence of light chain of 357, 378
      and 161, synthetic

<400> SEQUENCE: 12
atggcctgcc ccggcttcct gtgggccctg gtgatcagca cctgcctcga gttttccatg      60
gctgacattc agatgaccca gtctccatcc tccctgtctg catctgtagg agacagagtc     120
accatcactt gccgggcaag tcagagcatt agcagctact taaattggta tcagcagaaa     180
ccagggaaag cccctaagct cctgatctat gctgcatcca gtttgcaaag tggggtccca     240
tcaaggttca gtggcagtgg atctgggaca gatttcactc tcaccatcag cagtctgcaa     300
cctgaagatt ttgcaactta ctactgtcaa cagagttaca gtacccctcc aacgttcggc     360
caagggacca aggtggagat caaacggacc gtggccgctc ccagcgtgtt catcttcccc     420
ccctccgacg agcagctgaa gagcggcacc gccagcgtgg tgtgcctgct gaacaacttc     480 taccccggg aggccaaggt gcagtggaag gtggacaacg ccctgcagag cggcaacagc     540
caggagagcg tgaccgagca ggacagcaag gactccacct acagcctgag cagcacccttc    600 accctgagca aggccgacta cgagaagcac aaggtgtacg cctgcgaggt gacccaccag     660
ggcctgagca gccccgtgac caagagcttc aaccggggcg agtgttaa                  708

<210> SEQ ID NO 13
<211> LENGTH: 214
<212> TYPE: PRT
<213> ORGANISM: Artificial sequence
<220> FEATURE:
<223> OTHER INFORMATION: Amino acid sequence of light chain of 357, 378
      and 161, synthetic

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Pro
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
```

<210> SEQ ID NO 14
<211> LENGTH: 720
<212> TYPE: DNA
<213> ORGANISM: Artificial sequence
<220> FEATURE:
<223> OTHER INFORMATION: Nucleotide sequence of SC02-357, synthetic

<400> SEQUENCE: 14

```
caggtgcagc tgcaggagtc gggggccagga ctggtgaagc cttcggagac cctgtccctc    60
acctgcgttg tctctggtgg ctccatcagc agtagtaact ggtggagctg ggtccgccag   120
cccccaggga aggggctgga gtggattggg gaaatctatc atagtgggag ccccgactac   180
aacccgtccc tcaagagtcg agtcaccata tcagtagaca gtccaggaa ccagttctcc    240
ctgaagctga gctctgtgac cgccgcggac acggccgtgt attactgtgc aaaggttagt   300
actggtggtt tctttgacta ctggggccaa ggtaccctgg tcaccgtctc gagtggtgga   360
ggcggttcag gcggaggtgg ctctggcggt ggcggatcgg aaattgagct cacccagtct   420
ccatcctccc tgtctgcatc tgtaggagac agagtcacca tcacttgccg ggcaagtcag   480
agcattagca gctacttaaa ttggtatcag cagaaaccag ggaaagcccc taagctcctg   540
atctatgctg catccagttt gcaaagtggg gtcccatcaa ggttcagtgg cagtggatct   600
gggacagatt tcactctcac catcagcagt ctgcaacctg aagattttgc aacttactac   660
tgtcaacaga gttacagtac ccctccaacg ttcggcccag ggaccaaggt ggagatcaaa   720
```

<210> SEQ ID NO 15
<211> LENGTH: 240
<212> TYPE: PRT
<213> ORGANISM: Artificial sequence
<220> FEATURE:
<223> OTHER INFORMATION: Amino acid sequence of SC02-357, synthetic

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asp Tyr Asn Pro Ser Leu
    50                  55                  60

Lys Ser Arg Val Thr Ile Ser Val Asp Lys Ser Arg Asn Gln Phe Ser
65                  70                  75                  80

Leu Lys Leu Ser Ser Val Thr Ala Ala Asp Thr Ala Val Tyr Tyr Cys
                85                  90                  95

Ala Lys Val Ser Thr Gly Gly Phe Phe Asp Tyr Trp Gly Gln Gly Thr
            100                 105                 110

Leu Val Thr Val Ser Ser Gly Gly Gly Gly Ser Gly Gly Gly Gly Ser
        115                 120                 125

Gly Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro

```
                    180                 185                 190
Ser Arg Phe Ser Gly Ser Gly Ser Gly Thr Asp Phe Thr Leu Thr Ile
            195                 200                 205

Ser Ser Leu Gln Pro Glu Asp Phe Ala Thr Tyr Tyr Cys Gln Gln Ser
        210                 215                 220

Tyr Ser Thr Pro Pro Thr Phe Gly Pro Gly Thr Lys Val Glu Ile Lys
225                 230                 235                 240
```

<210> SEQ ID NO 16
<211> LENGTH: 720
<212> TYPE: DNA
<213> ORGANISM: Artificial sequence
<220> FEATURE:
<223> OTHER INFORMATION: Nucleotide sequence of SC02-378, synthetic

<400> SEQUENCE: 16

```
caggtgcagc tgcaggagtc gggcccagga ctggtgaagc cttcggagac cctgtccctc    60
acctgcgttg tctctggtgg ctccatcagc agtagtaact ggtggagctg ggtccgccag   120
cccccaggga aggggctgga gtggattggg gaaatctatc atagtgggag ccccaactac   180
aacccgtccc tcaagagtcg agtcaccata tcagtagaca gtccaagaa ccagttctcc    240
ctgaagctga gctctgtgac cgccgcggac acggccgtgt attactgtgc aaggtcgtct   300
tctggtggtt tctttgacta ctggggccaa ggtaccctgg tcaccgtctc gagtggtgga   360
ggcggttcag gcggaggtgg ctctggcggt ggcggatcgg aaattgagct cacccagtct   420
ccatcctccc tgtctgcatc tgtaggagac agagtcacca tcacttgccg ggcaagtcag   480
agcattagca gctacttaaa ttggtatcag cagaaaccag ggaaagcccc taagctcctg   540
atctatgctg catccagttt gcaaagtggg gtcccatcaa ggttcagtgg cagtggatct   600
gggacagatt tcactctcac catcagcagt ctgcaacctg aagattttgc aacttactac   660
tgtcaacaga gttacagtac ccctccaacg ttcggccaag ggaccaaggt ggagatcaaa   720
```

<210> SEQ ID NO 17
<211> LENGTH: 244
<212> TYPE: PRT
<213> ORGANISM: Artificial sequence
<220> FEATURE:
<223> OTHER INFORMATION: Amino acid sequence of SC02-378, synthetic

<400> SEQUENCE: 17

```
Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
            20                  25                  30

Asn Trp Trp Ser Trp Val Arg Gln Pro Gly Lys Gly Leu Glu Trp
        35                  40                  45

Ile Gly Glu Ile Tyr His Ser Gly Ser Pro Asn Tyr Asn Pro Ser Leu
    50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Ser Ser Gly Gly Phe Phe Asp Tyr Trp Gly Gln Gly Thr
                100                 105                 110

Leu Val Thr Val Ser Ser Gly Gly Gly Gly Ser Gly Gly Gly Gly Ser
            115                 120                 125

Gly Gly Gly Gly Ser Glu Ile Glu Leu Thr Gln Ser Pro Ser Ser Leu
```

```
                        130                 135                 140
Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
    210                 215                 220

Tyr Ser Thr Pro Pro Thr Phe Gly Gln Gly Thr Lys Val Glu Ile Lys
225                 230                 235                 240

Arg Ala Ala Ala

<210> SEQ ID NO 18
<211> LENGTH: 720
<212> TYPE: DNA
<213> ORGANISM: Artificial sequence
<220> FEATURE:
<223> OTHER INFORMATION: Nucleotide sequence of SC02-161, synthetic

<400> SEQUENCE: 18
caggtgcagc tgcaggagtc gggcccagga ctggtgaagc cttcggagac cctgtccctc     60
acctgcgttg tctctggtgg ctccatcagc agtagtaact ggtggagctg ggtccgccag    120
cccccaggga aggggctgga gtggattggg gaaatctatc atagtgggag ccccaactac    180
aacccgtccc tcaagagtcg agtcaccata tcagtagaca gtccaagaa ccagttctcc    240 ctgaagctga gctctgtgac cgccgcggac acggccgtgt attactgtgc aaggcagact    300
actgctgggt cctttgacta ctggggccaa ggtaccctgg tcaccgtctc gagtggtgga    360
ggcggttcag gcggaggtgg ctctggcggt ggcggatcgg aaattgagct cacccagtct    420
ccatcctccc tgtctgcatc tgtaggagac agagtcacca tcacttgccg ggcaagtcag    480
agcattagca gctacttaaa ttggtatcag cagaaaccag ggaaagcccc taagctcctg    540
atctatgctg catccagttt gcaaagtggg gtcccatcaa ggttcagtgg cagtggatct    600
gggacagatt tcactctcac catcagcagt ctgcaacctg aagattttgc aacttactac    660
tgtcaacaga gttacagtac ccctccaacg ttcggccaag gaccaaggt ggagatcaaa    720

<210> SEQ ID NO 19
<211> LENGTH: 244
<212> TYPE: PRT
<213> ORGANISM: Artificial sequence
<220> FEATURE:
<223> OTHER INFORMATION: Amino acid sequence of SC02-161, synthetic

<400> SEQUENCE: 19

Gln Val Gln Leu Gln Glu Ser Gly Pro Gly Leu Val Lys Pro Ser Glu
1               5                   10                  15

Thr Leu Ser Leu Thr Cys Val Val Ser Gly Gly Ser Ile Ser Ser Ser
                20                  25                  30

Asn Trp Trp Ser Trp Val Arg Gln Pro Pro Gly Lys Gly Leu Glu Trp
            35                  40                  45

Ile Gly Glu Ile Tyr His Ser Gly Ser Pro Asn Tyr Asn Pro Ser Leu
        50                  55                  60

Lys Ser Arg Val Thr Ile Ser Val Asp Lys Ser Lys Asn Gln Phe Ser
65                  70                  75                  80
```

```
Leu Lys Leu Ser Ser Val Thr Ala Ala Asp Thr Ala Val Tyr Tyr Cys
                 85                  90                  95

Ala Arg Gln Thr Thr Ala Gly Ser Phe Asp Tyr Trp Gly Gln Gly Thr
            100                 105                 110

Leu Val Thr Val Ser Ser Gly Gly Gly Gly Ser Gly Gly Gly Gly Ser
                115                 120                 125

Gly Gly Gly Gly Ser Glu Ile Glu Leu Thr Gln Ser Pro Ser Ser Leu
    130                 135                 140

Ser Ala Ser Val Gly Asp Arg Val Thr Ile Thr Cys Arg Ala Ser Gln
145                 150                 155                 160

Ser Ile Ser Ser Tyr Leu Asn Trp Tyr Gln Gln Lys Pro Gly Lys Ala
                165                 170                 175

Pro Lys Leu Leu Ile Tyr Ala Ala Ser Ser Leu Gln Ser Gly Val Pro
            180                 185                 190

Ser Arg Phe Ser Gly Ser Gly Ser Gly Thr Asp Phe Thr Leu Thr Ile
        195                 200                 205

Ser Ser Leu Gln Pro Glu Asp Phe Ala Thr Tyr Tyr Cys Gln Gln Ser
    210                 215                 220

Tyr Ser Thr Pro Pro Thr Phe Gly Gln Gly Thr Lys Val Glu Ile Lys
225                 230                 235                 240

Arg Ala Ala Ala

<210> SEQ ID NO 20
<211> LENGTH: 21
<212> TYPE: DNA
<213> ORGANISM: Artificial sequence
<220> FEATURE:
<223> OTHER INFORMATION: Forward primer for human C-type lectin,
      synthetic

<400> SEQUENCE: 20
gtgatgatgt ccaaacatgg c                                           21

<210> SEQ ID NO 21
<211> LENGTH: 20
<212> TYPE: DNA
<213> ORGANISM: Artificial sequence
<220> FEATURE:
<223> OTHER INFORMATION: Reverse primer for human C-type lectin,
      synthetic

<400> SEQUENCE: 21
gattgatgcc tcatgcctcc                                             20

<210> SEQ ID NO 22
<211> LENGTH: 19
<212> TYPE: DNA
<213> ORGANISM: Artificial sequence
<220> FEATURE:
<223> OTHER INFORMATION: Forward primer for beta-actin, synthetic

<400> SEQUENCE: 22
ggcatcgtga tggactccg                                              19

<210> SEQ ID NO 23
<211> LENGTH: 19
<212> TYPE: DNA
<213> ORGANISM: Artificial sequence
<220> FEATURE:
<223> OTHER INFORMATION: Reverse primer for beta-actin, synthetic

<400> SEQUENCE: 23
```

```
gctggaaggt ggacagcga                                                  19

<210> SEQ ID NO 24
<211> LENGTH: 6778
<212> TYPE: DNA
<213> ORGANISM: Artificial sequence
<220> FEATURE:
<223> OTHER INFORMATION: Expression vector pcDNA-SY-HC, synthetic

<400> SEQUENCE: 24
ctagagggcc cgtttaaacc cgctgatcag cctcgactgt gccttctagt tgccagccat      60
ctgttgtttg cccctccccc gtgccttcct tgaccctgga aggtgccact cccactgtcc     120
tttcctaata aaatgaggaa attgcatcgc attgtctgag taggtgtcat tctattctgg     180
ggggtggggt ggggcaggac agcaaggggg aggattggga agacaatagc aggcatgctg     240
gggatgcggt gggctctatg gcttctgagg cggaaagaac cagctggggc tctaggggt      300 atccccacgc gccctgtagc ggcgcattaa gcgcggcggg tgtggtggtt acgcgcagcg     360
tgaccgctac acttgccagc gccctagcgc ccgctccttt cgctttcttc ccttcctttc     420
tcgccacgtt cgccggcttt ccccgtcaag ctctaaatcg gggctccct ttagggttcc      480 gatttagtgc tttacggcac ctcgacccca aaaaacttga ttagggtgat ggttcacgta     540
gtgggccatc gccctgatag acggtttttc gccctttgac gttggagtcc acgttcttta     600
atagtggact cttgttccaa actggaacaa cactcaaccc tatctcggtc tattcttttg     660
atttataagg gattttgccg atttcggcct attggttaaa aaatgagctg atttaacaaa     720
aatttaacgc gaattaattc tgtggaatgt gtgtcagtta gggtgtggaa agtccccagg     780
ctccccagca ggcagaagta tgcaaagcat gcatctcaat tagtcagcaa ccaggtgtgg     840
aaagtcccca ggctccccag caggcagaag tatgcaaagc atgcatctca attagtcagc     900
aaccatagtc cgcccctaa ctccgcccat cccgccccta actccgccca gttccgccca      960
ttctccgccc catggctgac taatttttt tatttatgca gaggccgagg ccgcctctgc     1020
ctctgagcta ttccagaagt agtgaggagg ctttttttgga ggcctaggct tttgcaaaaa    1080
gctcccggga gcttgtatat ccattttcgg atctgatcaa gagacaggat gaggatcgtt    1140
tcgcatgatt gaacaagatg gattgcacgc aggttctccg gccgcttggg tggagaggct    1200
attcggctat gactgggcac aacagacaat cggctgctct gatgccgccg tgttccggct    1260
gtcagcgcag gggcgcccgg ttcttttttgt caagaccgac ctgtccggtg ccctgaatga    1320
actgcaggac gaggcagcgc ggctatcgtg gctggccacg acgggcgttc cttgcgcagc    1380
tgtgctcgac gttgtcactg aagcgggaag ggactggctg ctattgggcg aagtgccggg    1440
gcaggatctc ctgtcatctc accttgctcc tgccgagaaa gtatccatca tggctgatgc    1500
aatgcggcgg ctgcatacgc ttgatccggc tacctgccca ttcgaccacc aagcgaaaca    1560
tcgcatcgag cgagcacgta ctcggatgga agccggtctt gtcgatcagg atgatctgga    1620
cgaagagcat caggggctcg cgccagccga actgttcgcc aggctcaagg cgcgcatgcc    1680
cgacggcgag gatctcgtcg tgacccatgg cgatgcctgc ttgccgaata tcatggtgga    1740
aaatggccgc ttttctggat tcatcgactg tggccggctg ggtgtggcgg atcgctatca    1800
ggacatagcg ttggctaccc gtgatattgc tgaagagctt ggcggcgaat gggctgaccg    1860
cttcctcgtg ctttacggta tcgccgctcc cgattcgcag cgcatcgcct tctatcgcct    1920
tcttgacgag ttcttctgag cgggactctg gggttcgaaa tgaccgacca agcgacgccc    1980
aacctgccat cacgagattt cgattccacc gccgccttct atgaaaggtt gggcttcgga    2040
```

```
atcgttttcc gggacgccgg ctggatgatc ctccagcgcg gggatctcat gctggagttc    2100
ttcgcccacc ccaacttgtt tattgcagct tataatggtt acaaataaag caatagcatc    2160
acaaatttca caaataaagc attttttttca ctgcattcta gttgtggttt gtccaaactc   2220
atcaatgtat cttatcatgt ctgtataccg tcgacctcta gctagagctt ggcgtaatca    2280
tggtcatagc tgtttcctgt gtgaaattgt tatccgctca caattccaca acatacga     2340 gccggaagca taaagtgtaa agcctggggt gcctaatgag tgagctaact cacattaatt    2400
gcgttgcgct cactgcccgc tttccagtcg ggaaacctgt cgtgccagct gcattaatga    2460
atcggccaac gcgcgggag aggcggtttg cgtattgggc gctcttccgc ttcctcgctc     2520
actgactcgc tgcgctcggt cgttcggctg cggcgagcgg tatcagctca ctcaaaggcg    2580
gtaatacggt tatccacaga atcagggga taacgcagga agaacatgtg agcaaaaggc    2640
cagcaaaagg ccaggaaccg taaaaaggcc gcgttgctgg cgtttttcca taggctccgc    2700 cccctgacg agcatcacaa aaatcgacgc tcaagtcaga ggtggcgaaa cccgacagga    2760
ctataaagat accaggcgtt tccccctgga agctccctcg tgcgctctcc tgttccgacc    2820
ctgccgctta ccggatacct gtccgccttt ctcccttcgg gaagcgtggc gctttctcat    2880
agctcacgct gtaggtatct cagttcggtg taggtcgttc gctccaagct gggctgtgtg    2940
cacgaacccc ccgttcagcc cgaccgctgc gccttatccg gtaactatcg tcttgagtcc    3000
aacccggtaa gacacgactt atcgccactg gcagcagcca ctggtaacag gattagcaga    3060
gcgaggtatg taggcggtgc tacagagttc ttgaagtggt ggcctaacta cggctacact    3120
agaagaacag tatttggtat ctgcgctctg ctgaagccag ttaccttcgg aaaaagagtt    3180
ggtagctctt gatccggcaa acaaaccacc gctggtagcg gtttttttgt ttgcaagcag    3240
cagattacgc gcagaaaaaa aggatctcaa gaagatcctt tgatcttttc tacggggtct    3300
gacgctcagt ggaacgaaaa ctcacgttaa gggattttgg tcatgagatt atcaaaaagg    3360
atcttcacct agatcctttt aaattaaaaa tgaagtttta atcaatcta aagtatatat     3420 gagtaaactt ggtctgacag ttaccaatgc ttaatcagtg aggcacctat ctcagcgatc    3480
tgtctatttc gttcatccat agttgcctga ctccccgtcg tgtagataac tacgatacgg    3540
gagggcttac catctggccc cagtgctgca atgataccgc gagacccacg ctcaccggct    3600
ccagatttat cagcaataaa ccagccagcc ggaagggccg agcgcagaag tggtcctgca    3660
actttatccg cctccatcca gtctattaat tgttgccggg aagctagagt aagtagttcg    3720
ccagttaata gtttgcgcaa cgttgttgcc attgctacag gcatcgtggt gtcacgctcg    3780
tcgtttggta tggcttcatt cagctccggt tcccaacgat caaggcgagt tacatgatcc    3840
cccatgttgt gcaaaaaagc ggttagctcc ttcggtcctc cgatcgttgt cagaagtaag    3900
ttggccgcag tgttatcact catggttatg gcagcactgc ataattctct tactgtcatg    3960
ccatccgtaa gatgcttttc tgtgactggt gagtactcaa ccaagtcatt ctgagaatag    4020
tgtatgcggc gaccgagttg ctcttgcccg gcgtcaatac gggataatac cgcgccacat    4080
agcagaactt taaaagtgct catcattgga aaacgttctt cggggcgaaa actctcaagg    4140
atcttaccgc tgttgagatc cagttcgatg taacccactc gtgcacccaa ctgatcttca    4200
gcatctttta ctttcaccag cgtttctggg tgagcaaaaa caggaaggca aaatgccgca    4260
aaaaagggaa taagggcgac acggaaatgt tgaatactca tactcttcct ttttcaatat    4320
tattgaagca tttatcaggg ttattgtctc atgagcggat acatatttga atgtatttag    4380
aaaaataaac aaataggggt tccgcgcaca tttccccgaa aagtgccacc tgacgtcgac    4440
```

```
ggatcgggag atctcccgat cccctatggt gcactctcag tacaatctgc tctgatgccg   4500
catagttaag ccagtatctg ctccctgctt gtgtgttgga ggtcgctgag tagtgcgcga   4560
gcaaaattta agctacaaca aggcaaggct tgaccgacaa ttgcatgaag aatctgctta   4620
gggttaggcg ttttgcgctg cttcgctagg tggtcaatat tggccattag ccatattatt   4680
cattggttat atagcataaa tcaatattgg ctattggcca ttgcatacgt tgtatccata   4740
tcataatatg tacatttata ttggctcatg tccaacatta ccgccatgtt gacattgatt   4800
attgactagt tattaatagt aatcaattac ggggtcatta gttcatagcc catatatgga   4860
gttccgcgtt acataactta cggtaaatgg cccgcctggc tgaccgccca acgaccccg    4920 cccattgacg tcaataatga cgtatgttcc catagtaacg ccaatagggactttccattg   4980 acgtcaatgg gtggagtatt tacggtaaac tgcccacttg gcagtacatc aagtgtatca   5040
tatgccaagt acgcccccta ttgacgtcaa tgacggtaaa tggcccgcct ggcattatgc   5100
ccagtacatg accttatggg actttcctac ttggcagtac atctacgtat tagtcatcgc   5160
tattaccatg gtgatgcggt tttggcagta catcaatggg cgtggatagc ggtttgactc   5220
acggggattt ccaagtctcc accccattga cgtcaatggg agtttgtttt ggcaccaaaa   5280
tcaacgggac tttccaaaat gtcgtaacaa ctccgcccca ttgacgcaaa tgggcggtag   5340
gcgtgtacgg tgggaggtct atataagcag agctcgttta gtgaaccgtc agatcgcctg   5400
gagacgccat ccacgctgtt ttgacctcca tagaagacac cgggaccgat ccagcctccg   5460
cggccgggaa cggtgcattg gaagctggcc tggatggcct gactctctta ggtagccttg   5520
cagaagttgg tcgtgaggca ctgggcaggt aagtatcaag gttacaagac aggtttaagg   5580
agatcaatag aaactgggct tgtcgagaca gagaagactc ttgcgtttct gataggcacc   5640
tattggtctt actgacatcc actttgcctt tctctccaca ggtgtccact cccagttcaa   5700
ttacagctcg ccaccatggc ctgccccggc ttcctgtggg ccctggtgat cagcacctgc   5760
ctggaattca gcatgagcag cgctagcacc aagggcccca gcgtgttccc cctggccccc   5820
agcagcaaga gcaccagcgg cggcacagcc gccctgggct gcctggtgaa ggactacttc   5880
cccgagcccg tgaccgtgag ctggaacagc ggcgccttga ccagcggcgt gcacaccttc   5940
cccgccgtgc tgcagagcag cggcctgtac agcctgagca gcgtggtgac cgtgcccagc   6000
agcagcctgg gcacccagac ctacatctgc aacgtgaacc acaagcccag caacaccaag   6060
gtggacaaac gcgtggagcc caagagctgc gacaagaccc acacctgccc ccctgccct    6120 gccccgagc tgctgggcgg accctccgtg ttcctgttcc ccccaagcc caaggacacc    6180 ctcatgatca gccggacccc cgaggtgacc tgcgtggtgg tggacgtgag ccacgaggac   6240
cccgaggtga agttcaactg gtacgtggac ggcgtggagg tgcacaacgc caagaccaag   6300
ccccgggagg agcagtacaa cagcacctac cgggtggtga gcgtgctcac cgtgctgcac   6360
caggactggc tgaacggcaa ggagtacaag tgcaaggtga gcaacaaggc cctgcctgcc   6420
cccatcgaga agaccatcag caaggccaag ggccagcccc gggagcccca ggtgtacacc   6480
ctgcccccca gccgggagga gatgaccaag aaccaggtgt ccctcacctg tctggtgaag   6540
ggcttctacc ccagcgacat cgccgtggag tgggagagca cggccagcc cgagaacaac   6600 tacaagacca ccccccctgt gctggacagc gacggcagct tcttcctgta cagcaagctc   6660
accgtggaca gagccggtg gcagcaggc aacgtgttca gctgcagcgt gatgcacgag   6720
gccctgcaca accactacac ccagaagagc ctgagcctga gccccggcaa gtgataat     6778
```

<210> SEQ ID NO 25
<211> LENGTH: 6267
<212> TYPE: DNA
<213> ORGANISM: Artificial sequence
<220> FEATURE:
<223> OTHER INFORMATION: Expression vector pcDNA-SY-kappa, synthetic

<400> SEQUENCE: 25

| | | | | | |
|---|---|---|---|---|---|
| ttaagtttaa | accgctgatc | agcctcgact | gtgccttcta | gttgccagcc | atctgttgtt | 60 |
| tgcccctccc | ccgtgccttc | cttgaccctg | gaaggtgcca | ctcccactgt | cctttcctaa | 120 |
| taaaatgagg | aaattgcatc | gcattgtctg | agtaggtgtc | attctattct | ggggggtggg | 180 |
| gtggggcagg | acagcaaggg | ggaggattgg | gaagacaata | gcaggcatgc | tggggatgcg | 240 |
| gtgggctcta | tggcttctga | ggcggaaaga | accagctggg | gctctagggg | gtatccccac | 300 |
| gcgccctgta | gcggcgcatt | aagcgcggcg | ggtgtggtgg | ttacgcgcag | cgtgaccgct | 360 |
| acacttgcca | gcgccctagc | gcccgctcct | ttcgctttct | tcccttcctt | tctcgccacg | 420 |
| ttcgccggct | ttccccgtca | agctctaaat | cgggggctcc | ctttagggtt | ccgatttagt | 480 |
| gctttacggc | acctcgaccc | caaaaaactt | gattagggtg | atggttcacg | tagtgggcca | 540 |
| tcgccctgat | agacggtttt | tcgccctttg | acgttggagt | ccacgttctt | taatagtgga | 600 |
| ctcttgttcc | aaactggaac | aacactcaac | cctatctcgg | tctattcttt | tgatttataa | 660 |
| gggattttgg | ccattttcggc | ctattggtta | aaaaatgagc | tgatttaaca | aaaatttaac | 720 |
| gcgaattaat | tctgtggaat | gtgtgtcagt | tagggtgtgg | aaagtcccca | ggctccccag | 780 |
| caggcagaag | tatgcaaagc | atgcatctca | attagtcagc | aaccaggtgt | ggaaagtccc | 840 |
| caggctcccc | agcaggcaga | agtatgcaaa | gcatgcatct | caattagtca | gcaaccatag | 900 |
| tcccgcccct | aactccgccc | atcccgcccc | taactccgcc | cagttccgcc | cattctccgc | 960 |
| cccatggctg | actaattttt | tttatttatg | cagaggccga | ggccgcctct | gcctctgagc | 1020 |
| tattccagaa | gtagtgagga | ggcttttttg | gaggcctagg | cttttgcaaa | aagctcccgg | 1080 |
| gagcttgtat | atccattttc | ggatctgatc | agcacgtgat | gaaaaagcct | gaactcaccg | 1140 |
| cgacgtctgt | cgagaagttt | ctgatcgaaa | agttcgacag | cgtctccgac | ctgatgcagc | 1200 |
| tctcggaggg | cgaagaatct | cgtgctttca | gcttcgatgt | aggagggcgt | ggatatgtcc | 1260 |
| tgcgggtaaa | tagctgcgcc | gatggtttct | acaaagatcg | ttatgtttat | cggcactttg | 1320 |
| catcggccgc | gctcccgatt | ccggaagtgc | ttgacattgg | ggaattcagc | gagagcctga | 1380 |
| cctattgcat | ctcccgccgt | gcacagggtg | tcacgttgca | agacctgcct | gaaaccgaac | 1440 |
| tgcccgctgt | tctgcagccg | gtcgcggagg | ccatggatgc | gatcgctgcg | gccgatctta | 1500 |
| gccagacgag | cgggttcggc | ccattcggac | cacaaggaat | cggtcaatac | actacatggc | 1560 |
| gtgatttcat | atgcgcgatt | gctgatcccc | atgtgtatca | ctggcaaact | gtgatggacg | 1620 |
| acaccgtcag | tgcgtccgtc | gcgcaggctc | tcgatgagct | gatgctttgg | gccgaggact | 1680 |
| gccccgaagt | ccggcacctc | gtgcacgcgg | atttcggctc | caacaatgtc | ctgacggaca | 1740 |
| atggccgcat | aacagcggtc | attgactgga | gcgaggcgat | gttcggggat | tcccaatacg | 1800 |
| aggtcgccaa | catcttcttc | tggaggccgt | ggttggcttg | tatggagcag | cagacgcgct | 1860 |
| acttcgagcg | gaggcatccg | gagcttgcag | gatcgccgcg | gctccgggcg | tatatgctcc | 1920 |
| gcattggtct | tgaccaactc | tatcagagct | tggttgacgg | caatttcgat | gatgcagctt | 1980 |
| gggcgcaggg | tcgatgcgac | gcaatcgtcc | gatccggagc | cgggactgtc | gggcgtacac | 2040 |
| aaatcgcccg | cagaagcgcg | gccgtctgga | ccgatggctg | tgtagaagta | ctcgccgata | 2100 |
| gtggaaaccg | acgccccagc | actcgtccga | gggcaaagga | atagcacgtg | ctacgagatt | 2160 |

```
tcgattccac cgccgccttc tatgaaaggt tgggcttcgg aatcgttttc cgggacgccg    2220
gctggatgat cctccagcgc ggggatctca tgctggagtt cttcgcccac cccaacttgt    2280
ttattgcagc ttataatggt tacaaataaa gcaatagcat cacaaatttc acaaataaag    2340
catttttttc actgcattct agttgtggtt tgtccaaact catcaatgta tcttatcatg    2400
tctgtatacc gtcgacctct agctagagct tggcgtaatc atggtcatag ctgtttcctg    2460
tgtgaaattg ttatccgctc acaattccac acaacatacg agccgaagc ataaagtgta    2520 aagcctgggg tgcctaatga gtgagctaac tcacattaat tgcgttgcgc tcactgcccg    2580
ctttccagtc gggaaacctg tcgtgccagc tgcattaatg aatcggccaa cgcgcgggga    2640
gaggcggttt gcgtattggg cgctcttccg cttcctcgct cactgactcg ctgcgctcgg    2700
tcgttcggct gcggcgagcg gtatcagctc actcaaaggc ggtaatacgg ttatccacag    2760
aatcagggga taacgcagga agaacatgt gagcaaaagg ccagcaaaag gccaggaacc    2820
gtaaaaaggc cgcgttgctg gcgttttttcc ataggctccg ccccctgac gagcatcaca    2880 aaaatcgacg ctcaagtcag aggtggcgaa acccgacagg actataaaga taccaggcgt    2940
ttccccctgg aagctccctc gtgcgctctc ctgttccgac cctgccgctt accggatacc    3000
tgtccgcctt tctcccttcg ggaagcgtgg cgctttctca tagctcacgc tgtaggtatc    3060
tcagttcggt gtaggtcgtt cgctccaagc tgggctgtgt gcacgaaccc cccgttcagc    3120
ccgaccgctg cgccttatcc ggtaactatc gtcttgagtc aacccggta agacacgact    3180 tatcgccact ggcagcagcc actggtaaca ggattagcag agcgaggtat gtaggcggtg    3240
ctacagagtt cttgaagtgg tggcctaact acggctacac tagaagaaca gtatttggta    3300
tctgcgctct gctgaagcca gttaccttcg aaaaagagt tggtagctct tgatccggca    3360
aacaaaccac cgctggtagc ggttttttg tttgcaagca gcagattacg cgcagaaaaa    3420
aaggatctca agaagatcct ttgatctttt ctacggggtc tgacgctcag tggaacgaaa    3480
actcacgtta agggatttg gtcatgagat tatcaaaaag gatcttcacc tagatccttt    3540
taaattaaaa atgaagtttt aaatcaatct aaagtatata tgagtaaact tggtctgaca    3600
gttaccaatg cttaatcagt gaggcaccta tctcagcgat ctgtctattt cgttcatcca    3660
tagttgcctg actccccgtc gtgtagataa ctacgatacg ggagggctta ccatctggcc    3720
ccagtgctgc aatgataccg cgagacccac gctcaccggc tccagattta tcagcaataa    3780
accagccagc cggaagggcc gagcgcagaa gtggtcctgc aactttatcc gcctccatcc    3840
agtctattaa ttgttgccgg gaagctagag taagtagttc gccagttaat agtttgcgca    3900
acgttgttgc cattgctaca ggcatcgtgg tgtcacgctc gtcgtttggt atggcttcat    3960
tcagctccgg ttcccaacga tcaaggcgag ttacatgatc ccccatgttg tgcaaaaaag    4020
cggttagctc cttcggtcct ccgatcgttg tcagaagtaa gttggccgca gtgttatcac    4080
tcatggttat ggcagcactg cataattctc ttactgtcat gccatccgta agatgctttt    4140
ctgtgactgg tgagtactca accaagtcat tctgagaata gtgtatgcgg cgaccgagtt    4200
gctcttgccc ggcgtcaata cgggataata ccgcgccaca tagcagaact ttaaaagtgc    4260
tcatcattgg aaaacgttct tcggggcgaa aactctcaag gatcttaccg ctgttgagat    4320
ccagttcgat gtaaccccact cgtgcaccca actgatcttc agcatctttt actttcacca    4380
gcgtttctgg gtgagcaaaa acaggaaggc aaaatgccgc aaaaaaggga taagggcga    4440 cacgaaaatg ttgaatactc atactcttcc tttttcaata ttattgaagc atttatcagg    4500
gttattgtct catgagcgga tacatatttg aatgtattta gaaaaataaa caaatagggg    4560
```

```
ttccgcgcac atttccccga aaagtgccac ctgacgtcga cggatcggga gatctcccga    4620 tccccctatgg tgcactctca gtacaatctg ctctgatgcc gcatagttaa gccagtatct    4680
gctccctgct tgtgtgttgg aggtcgctga gtagtgcgcg agcaaaattt aagctacaac    4740
aaggcaaggc ttgaccgaca attgttaatt aacatgaaga atctgcttag ggttaggcgt    4800
tttgcgctgc ttcgctaggt ggtcaatatt ggccattagc catattattc attggttata    4860
tagcataaat caatattggc tattggccat tgcatacgtt gtatccatat cataatatgt    4920
acatttatat tggctcatgt ccaacattac cgccatgttg acattgatta ttgactagtt    4980
attaatagta atcaattacg gggtcattag ttcatagccc atatatggag ttccgcgtta    5040
cataacttac ggtaaatggc ccgcctggct gaccgcccaa cgaccccgc ccattgacgt     5100 caataatgac gtatgttccc atagtaacgc caatagggac tttccattga cgtcaatggg    5160
tggagtattt acggtaaact gcccacttgg cagtacatca agtgtatcat atgccaagta    5220
cgccccctat tgacgtcaat gacggtaaat ggcccgcctg gcattatgcc cagtacatga    5280
ccttatggga ctttcctact tggcagtaca tctacgtatt agtcatcgct attaccatgg    5340
tgatgcggtt ttggcagtac atcaatgggc gtggatagcg gtttgactca cggggatttc    5400
caagtctcca ccccattgac gtcaatggga gtttgttttg gcaccaaaat caacgggact    5460
ttccaaaatg tcgtaacaac tccgccccat tgacgcaaat gggcggtagg cgtgtacggt    5520
gggaggtcta taagcaga gctcgtttag tgaaccgtca gatcgcctgg agacgccatc     5580
cacgctgttt tgacctccat agaagacacc gggaccgatc cagcctccgc ggccgggaac    5640
ggtgcattgg aatcgatgac tctcttaggt agccttgcag aagttggtcg tgaggcactg    5700
ggcaggtaag tatcaaggtt acaagacagg tttaaggaga tcaatagaaa ctgggcttgt    5760
cgagacagag aagactcttg cgtttctgat aggcacctat tggtcttact gacatccact    5820 ttgccttct ctccacaggt gtccactccc agttcaatta cagctcgcca ccatggcctg    5880
ccccggcttc ctgtgggccc tggtgatcag cacctgcctc gagttcagcg ccctaagcg     5940 gaccgtggcc gctcccagcg tgttcatctt ccccccctcc gacgagcagc tgaagagcgg    6000
caccgccagc gtggtgtgcc tgctgaacaa cttctacccc cgggaggcca aggtgcagtg    6060
gaaggtggac aacgccctgc agagcggcaa cagccaggag agcgtgaccg agcaggacag    6120
caaggactcc acctacagcc tgagcagcac cctcaccctg agcaaggccg actacgagaa    6180
gcacaaggtg tacgcctgcg aggtgaccca ccagggcctg agcagccccg tgaccaagag    6240
cttcaaccgg ggcgagtgtt aatagac                                        6267
```

<210> SEQ ID NO 26
<211> LENGTH: 54
<212> TYPE: DNA
<213> ORGANISM: Artificial sequence
<220> FEATURE:
<223> OTHER INFORMATION: Oligonucleotide, synthetic

<400> SEQUENCE: 26
acctgtctcg agttttccat ggctgacatc cagatgaccc agtctccatc ctcc          54

<210> SEQ ID NO 27
<211> LENGTH: 42
<212> TYPE: DNA
<213> ORGANISM: Artificial sequence
<220> FEATURE:
<223> OTHER INFORMATION: Oligonucleotide, synthetic

<400> SEQUENCE: 27

```
gggaccaagg tggagatcaa acggaccgtg ccgccccca gc                42
```

<210> SEQ ID NO 28
<211> LENGTH: 50
<212> TYPE: DNA
<213> ORGANISM: Artificial sequence
<220> FEATURE:
<223> OTHER INFORMATION: Oligonucleotide, synthetic

<400> SEQUENCE: 28

```
acctgtcttg aattctccat ggcccaggtg cagctgcagg agtccggccc       50
```

<210> SEQ ID NO 29
<211> LENGTH: 47
<212> TYPE: DNA
<213> ORGANISM: Artificial sequence
<220> FEATURE:
<223> OTHER INFORMATION: Oligonucleotide, synthetic

<400> SEQUENCE: 29

```
gcccttggtg ctagcgctgg agacggtcac cagggtgccc tggcccc         47
```

<210> SEQ ID NO 30
<211> LENGTH: 3597
<212> TYPE: DNA
<213> ORGANISM: Artificial sequence
<220> FEATURE:
<223> OTHER INFORMATION: Vector pPICZalphaB, synthetic

<400> SEQUENCE: 30

```
agatctaaca tccaaagacg aaaggttgaa tgaaacctttt ttgccatccg acatccacag    60
gtccattctc acacataagt gccaaacgca acaggagggg atacactagc agcagaccgt   120
tgcaaacgca ggacctccac tcctcttctc ctcaacaccc acttttgcca tcgaaaaacc   180
agcccagtta tttgggcttga ttggagctcg ctcattccaa ttccttctat taggctacta   240
acaccatgac tttattagcc tgtctatcct ggccccctg gcgaggttca tgtttgttta    300
tttccgaatg caacaagctc cgcattacac ccgaacatca ctccagatga gggctttctg   360
agtgtggggt caaatagttt catgttcccc aaatggccca aaactgacag tttaaacgct   420
gtcttggaac ctaatatgac aaaagcgtga tctcatccaa gatgaactaa gtttggttcg   480
ttgaaatgct aacggccagt tggtcaaaaa gaaacttcca aaagtcggca taccgtttgt   540
cttgtttggt attgattgac gaatgctcaa aaataatctc attaatgctt agcgcagtct   600
ctctatcgct tctgaaccce ggtgcacctg tgccgaaacg caaatgggga acacccgct   660
ttttggatga ttatgcattg tctccacatt gtatgcttcc aagattctgg tgggaatact   720
gctgatagcc taacgttcat gatcaaaatt taactgttct aaccccctact tgacagcaat   780
atataaacag aaggaagctg ccctgtctta aaccttttttt tttatcatca ttattagctt   840
actttcataa ttgcgactgg ttccaattga caagcttttg attttaacga cttttaacga   900
caacttgaga agatcaaaaa acaactaatt attcgaaacg atgagatttc cttcaatttt  960
tactgctgtt ttattcgcag catcctccgc attagctgct ccagtcaaca ctacaacaga  1020
agatgaaacg gcacaaattc cggctgaagc tgtcatcggt tactcagatt tagaagggga  1080
tttcgatgtt gctgttttgc cattttccaa cagcacaaat aacgggttat tgtttataaa  1140
tactactatt gccagcattg ctgctaaaga agaagggggta tctctcgaga aaagagaggc  1200
tgaagctgca ggaattcacg tggcccagcc ggccgtctcg gatcggtacc tcgagccgcg  1260
gcggccgcca gctttctaga acaaaaactc atctcagaag aggatctgaa tagcgccgtc  1320
```

```
gaccatcatc atcatcatca ttgagtttgt agccttagac atgactgttc ctcagttcaa   1380
gttgggcact tacgagaaga ccggtcttgc tagattctaa tcaagaggat gtcagaatgc   1440
catttgcctg agagatgcag gcttcatttt tgatactttt ttatttgtaa cctatatagt   1500
ataggatttt ttttgtcatt ttgtttcttc tcgtacgagc ttgctcctga tcagcctatc   1560
tcgcagctga tgaatatctt gtggtagggg tttgggaaaa tcattcgagt ttgatgtttt   1620
tcttggtatt tcccactcct cttcagagta cagaagatta agtgagacct tcgtttgtgc   1680
ggatccccca cacaccatag cttcaaaatg tttctactcc tttttttactc ttccagatt   1740
tctcggactc cgcgcatcgc cgtaccactt caaaacaccc aagcacagca tactaaattt   1800
tccctcttc ttcctctagg gtgtcgttaa ttacccgtac taaaggtttg gaaaagaaaa    1860
aagagaccgc ctcgtttctt tttcttcgtc gaaaaaggca ataaaaattt ttatcacgtt   1920
tcttttctt gaaattttt tttttagttt ttttctcttt cagtgacctc cattgatatt    1980
taagttaata aacggtcttc aatttctcaa gtttcagttt catttttctt gttctattac   2040
aactttttt acttcttgtt cattagaaag aaagcatagc aatctaatct aaggggcggt    2100
gttgacaatt aatcatcggc atagtatatc ggcatagtat aatacgacaa ggtgaggaac   2160
taaaccatgg ccaagttgac cagtgccgtt ccggtgctca ccgcgcgcga cgtcgccgga   2220
gcggtcgagt tctggaccga ccggctcggg ttctcccggg acttcgtgga ggacgacttc   2280
gccggtgtgg tccgggacga cgtgaccctg ttcatcagcg cggtccagga ccaggtggtg   2340
ccggacaaca ccctggcctg ggtgtgggtg cgcggcctgg acgagctgta cgccgagtgg   2400
tcggaggtcg tgtccacgaa cttccgggac gcctccgggc cggccatgac cgagatcggc   2460
gagcagccgt ggggggcggga gttcgccctg cgcgacccgg ccggcaactg cgtgcacttc   2520
gtggccgagg agcaggactg acacgtccga cggcggccca cgggtcccag gcctcggaga   2580
tccgtccccc ttttccttg tcgatatcat gtaattagtt atgtcacgct tacattcacg    2640
ccctcccccc acatccgctc taaccgaaaa ggaaggagtt agacaacctg aagtctaggt   2700
ccctatttat ttttttatag ttatgttagt attaagaacg ttatttatat ttcaaatttt   2760
tcttttttt ctgtacagac gcgtgtacgc atgtaacatt atactgaaaa ccttgcttga   2820
gaaggttttg ggacgctcga aggctttaat ttgcaagctg gagaccaaca tgtgagcaaa   2880
aggccagcaa aaggccagga accgtaaaaa ggccgcgttg ctggcgtttt tccataggct   2940
ccgcccccct gacgagcatc acaaaaatcg acgctcaagt cagaggtggc gaaacccgac   3000
aggactataa agataccagg cgtttccccc tggaagctcc ctcgtgcgct ctcctgttcc   3060
gaccctgccg cttaccggat acctgtccgc ctttctccct tcgggaagcg tggcgctttc   3120
tcaatgctca cgctgtaggt atctcagttc ggtgtaggtc gttcgctcca agctgggctg   3180
tgtgcacgaa ccccccgttc agcccgaccg ctgcgcctta ccggtaact atcgtcttga    3240
gtccaacccg gtaagacacg acttatcgcc actggcagca gccactggta acaggattag   3300
cagagcgagg tatgtaggcg gtgctacaga gttcttgaag tggtggccta actacggcta   3360
cactagaagg acagtatttg gtatctgcgc tctgctgaag ccagttacct tcggaaaaag   3420
agttggtagc tcttgatccg gcaaacaaac caccgctggt agcggtggtt ttttgtttg    3480
caagcagcag attacgcgca gaaaaaaagg atctcaagaa gatcctttga tcttttctac   3540
ggggtctgac gctcagtgga acgaaaactc acgttaaggg attttggtca tgagatc      3597
```

<210> SEQ ID NO 31
<211> LENGTH: 1401

<212> TYPE: DNA
<213> ORGANISM: Artificial sequence
<220> FEATURE:
<221> NAME/KEY: CDS
<222> LOCATION: (64)..(1401)
<223> OTHER INFORMATION: Chimeric 357, synthetic

<400> SEQUENCE: 31

```
atggcctgcc ccggcttcct gtgggccctg gtgatcagca cctgcctgga attctccatg      60 gcc cag gtg cag ctg cag gag tcc ggc cca gga ctg gtg aag cct tcg     108
    Gln Val Gln Leu Gln Glu Ser Gly Pro Gly Leu Val Lys Pro Ser
    1               5                   10                  15 gag acc ctg tcc ctc acc tgc gtt gtc tct ggt ggc tcc atc agc agt     156
Glu Thr Leu Ser Leu Thr Cys Val Val Ser Gly Gly Ser Ile Ser Ser
                20                  25                  30 agt aac tgg tgg agc tgg gtc cgc cag ccc cca ggg aag ggg ctg gag     204
Ser Asn Trp Trp Ser Trp Val Arg Gln Pro Pro Gly Lys Gly Leu Glu
            35                  40                  45 tgg att ggg gaa atc tat cat agt ggg agc ccc gac tac aac ccg tcc     252
Trp Ile Gly Glu Ile Tyr His Ser Gly Ser Pro Asp Tyr Asn Pro Ser
        50                  55                  60 ctc aag agt cga gtc acc ata tca gta gac aag tcc agg aac cag ttc     300
Leu Lys Ser Arg Val Thr Ile Ser Val Asp Lys Ser Arg Asn Gln Phe
    65                  70                  75 tcc ctg aag ctg agc tct gtg acc gcc gcg gac acg gcc gtg tat tac     348
Ser Leu Lys Leu Ser Ser Val Thr Ala Ala Asp Thr Ala Val Tyr Tyr
80                  85                  90                  95 tgt gca aag gtt agt act ggt ggt ttc ttt gac tac tgg ggc cag ggc     396
Cys Ala Lys Val Ser Thr Gly Gly Phe Phe Asp Tyr Trp Gly Gln Gly
                100                 105                 110 acc ctg gtg acc gtc tcc agc gct agc acc aag ggc ccc agc gtg ttc     444
Thr Leu Val Thr Val Ser Ser Ala Ser Thr Lys Gly Pro Ser Val Phe
            115                 120                 125 ccc ctg gcc ccc agc agc aag agc acc agc ggc ggc aca gcc gcc ctg     492
Pro Leu Ala Pro Ser Ser Lys Ser Thr Ser Gly Gly Thr Ala Ala Leu
        130                 135                 140 ggc tgc ctg gtg aag gac tac ttc ccc gag ccc gtg acc gtg agc tgg     540
Gly Cys Leu Val Lys Asp Tyr Phe Pro Glu Pro Val Thr Val Ser Trp
    145                 150                 155 aac agc ggc gcc ttg acc agc ggc gtg cac acc ttc ccc gcc gtg ctg     588
Asn Ser Gly Ala Leu Thr Ser Gly Val His Thr Phe Pro Ala Val Leu
160                 165                 170                 175 cag agc agc ggc ctg tac agc ctg agc agc gtg gtg acc gtg ccc agc     636
Gln Ser Ser Gly Leu Tyr Ser Leu Ser Ser Val Val Thr Val Pro Ser
                180                 185                 190 agc agc ctg ggc acc cag acc tac atc tgc aac gtg aac cac aag ccc     684
Ser Ser Leu Gly Thr Gln Thr Tyr Ile Cys Asn Val Asn His Lys Pro
            195                 200                 205 agc aac acc aag gtg gac aaa cgc gtg gag ccc aag agc tgc gac aag     732
Ser Asn Thr Lys Val Asp Lys Arg Val Glu Pro Lys Ser Cys Asp Lys
        210                 215                 220 acc cac acc tgc ccc ccc tgc ccg gta cca gaa gta tca tct gtc ttc     780
Thr His Thr Cys Pro Pro Cys Pro Val Pro Glu Val Ser Ser Val Phe
    225                 230                 235 atc ttc ccc cca aag ccc aag gat gtg ctc acc att act ctg act cct     828
Ile Phe Pro Pro Lys Pro Lys Asp Val Leu Thr Ile Thr Leu Thr Pro
240                 245                 250                 255 aag gtc acg tgt gtt gtg gta gac atc agc aag gat gat ccc gag gtc     876
Lys Val Thr Cys Val Val Val Asp Ile Ser Lys Asp Asp Pro Glu Val
                260                 265                 270 cag ttc agc tgg ttt gta gat gat gtg gag gtg cac aca gct cag acg     924
Gln Phe Ser Trp Phe Val Asp Asp Val Glu Val His Thr Ala Gln Thr
```

```
caa ccc cgg gag gag cag ttc aac agc act ttc cgc tca gtc agt gaa    972
Gln Pro Arg Glu Glu Gln Phe Asn Ser Thr Phe Arg Ser Val Ser Glu
        290                 295                 300 ctt ccc atc atg cac cag gac tgg ctc aat ggc aag gag ttc aaa tgc   1020
Leu Pro Ile Met His Gln Asp Trp Leu Asn Gly Lys Glu Phe Lys Cys
305                 310                 315 agg gtc aac agt gca gct ttc cct gcc ccc atc gag aaa acc atc tcc   1068
Arg Val Asn Ser Ala Ala Phe Pro Ala Pro Ile Glu Lys Thr Ile Ser
320                 325                 330                 335 aaa acc aaa ggc aga ccg aag gct cca cag gtg tac acc att cca cct   1116
Lys Thr Lys Gly Arg Pro Lys Ala Pro Gln Val Tyr Thr Ile Pro Pro
                340                 345                 350 ccc aag gag cag atg gcc aag gat aaa gtc agt ctg acc tgc atg ata   1164
Pro Lys Glu Gln Met Ala Lys Asp Lys Val Ser Leu Thr Cys Met Ile
            355                 360                 365 aca gac ttc ttc cct gaa gac att act gtg gag tgg cag tgg aat ggg   1212
Thr Asp Phe Phe Pro Glu Asp Ile Thr Val Glu Trp Gln Trp Asn Gly
        370                 375                 380 cag cca gcg gag aac tac aag aac act cag ccc atc atg gac aca gat   1260
Gln Pro Ala Glu Asn Tyr Lys Asn Thr Gln Pro Ile Met Asp Thr Asp
385                 390                 395 ggc tct tac ttc gtc tac agc aag ctc aat gtg cag aag agc aac tgg   1308
Gly Ser Tyr Phe Val Tyr Ser Lys Leu Asn Val Gln Lys Ser Asn Trp
400                 405                 410                 415 gag gca gga aat act ttc acc tgc tct gtg tta cat gag ggc ctg cac   1356
Glu Ala Gly Asn Thr Phe Thr Cys Ser Val Leu His Glu Gly Leu His
                420                 425                 430 aac cac cat act gag aag agc ctc tcc cac tct cct ggt aaa tga       1401
Asn His His Thr Glu Lys Ser Leu Ser His Ser Pro Gly Lys
            435                 440                 445

<210> SEQ ID NO 32
<211> LENGTH: 445
<212> TYPE: PRT
<213> ORGANISM: Artificial sequence
<220> FEATURE:
<223> OTHER INFORMATION: Chimeric 357, synthetic

<400> SEQUENCE: 32

Gln Val Gln Leu Gln Glu Ser Gly Pro Gly Leu Val Lys Pro Ser Glu
1               5                   10                  15

Thr Leu Ser Leu Thr Cys Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Ile Tyr His Ser Gly Ser Pro Asp Tyr Asn Pro Ser Leu
    50                  55                  60

Lys Ser Arg Val Thr Ile Ser Val Asp Lys Ser Arg Asn Gln Phe Ser
65                  70                  75                  80

Leu Lys Leu Ser Ser Val Thr Ala Ala Asp Thr Ala Val Tyr Tyr Cys
                85                  90                  95

Ala Lys Val Ser Thr Gly Gly Phe Phe Asp Tyr Trp Gly Gln Gly Thr
            100                 105                 110

Leu Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140
```

```
Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
            165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Arg Val Glu Pro Lys Ser Cys Asp Lys Thr
210                 215                 220

His Thr Cys Pro Pro Cys Pro Val Pro Glu Val Ser Ser Val Phe Ile
225                 230                 235                 240

Phe Pro Pro Lys Pro Lys Asp Val Leu Thr Ile Thr Leu Thr Pro Lys
            245                 250                 255

Val Thr Cys Val Val Val Asp Ile Ser Lys Asp Asp Pro Glu Val Gln
            260                 265                 270

Phe Ser Trp Phe Val Asp Asp Val Glu Val His Thr Ala Gln Thr Gln
            275                 280                 285

Pro Arg Glu Glu Gln Phe Asn Ser Thr Phe Arg Ser Val Ser Glu Leu
290                 295                 300

Pro Ile Met His Gln Asp Trp Leu Asn Gly Lys Glu Phe Lys Cys Arg
305                 310                 315                 320

Val Asn Ser Ala Ala Phe Pro Ala Pro Ile Glu Lys Thr Ile Ser Lys
            325                 330                 335

Thr Lys Gly Arg Pro Lys Ala Pro Gln Val Tyr Thr Ile Pro Pro Pro
            340                 345                 350

Lys Glu Gln Met Ala Lys Asp Lys Val Ser Leu Thr Cys Met Ile Thr
            355                 360                 365

Asp Phe Phe Pro Glu Asp Ile Thr Val Glu Trp Gln Trp Asn Gly Gln
370                 375                 380

Pro Ala Glu Asn Tyr Lys Asn Thr Gln Pro Ile Met Asp Thr Asp Gly
385                 390                 395                 400

Ser Tyr Phe Val Tyr Ser Lys Leu Asn Val Gln Lys Ser Asn Trp Glu
            405                 410                 415

Ala Gly Asn Thr Phe Thr Cys Ser Val Leu His Glu Gly Leu His Asn
            420                 425                 430

His His Thr Glu Lys Ser Leu Ser His Ser Pro Gly Lys
            435                 440                 445

<210> SEQ ID NO 33
<211> LENGTH: 4
<212> TYPE: PRT
<213> ORGANISM: Artificial sequence
<220> FEATURE:
<223> OTHER INFORMATION: Synthetic peptide
<220> FEATURE:
<221> NAME/KEY: BINDING
<222> LOCATION: (1)..(4)
<223> OTHER INFORMATION: Xaa is any amino acid

<400> SEQUENCE: 33

Tyr Xaa Xaa Met
1

<210> SEQ ID NO 34
<211> LENGTH: 6
<212> TYPE: PRT
<213> ORGANISM: Artificial sequence
<220> FEATURE:
```

-continued

<223> OTHER INFORMATION: Synthetic peptide
<220> FEATURE:
<221> NAME/KEY: SITE
<222> LOCATION: (1)..(6)
<223> OTHER INFORMATION: Xaa in position 1 is Ile or Val;
      Xaa in position 2, 4 or 5 is any amino acid

<400> SEQUENCE: 34

Xaa Xaa Tyr Xaa Xaa Leu
1               5

<210> SEQ ID NO 35
<211> LENGTH: 46
<212> TYPE: DNA
<213> ORGANISM: Homo sapiens

<400> SEQUENCE: 35
tgtgttttta cactttgtca agatttcttt acatattcat caatgt            46

<210> SEQ ID NO 36
<211> LENGTH: 55
<212> TYPE: DNA
<213> ORGANISM: Artificial Sequence
<220> FEATURE:
<223> OTHER INFORMATION: Synthetic Construct, cloning site of
      pPicZalphaB

<400> SEQUENCE: 36
tctctcgaga aaagagaggc tgaagctgca ggaattcacg tggcccagcc ggccg       55

<210> SEQ ID NO 37
<211> LENGTH: 55
<212> TYPE: DNA
<213> ORGANISM: Artificial Sequence
<220> FEATURE:
<223> OTHER INFORMATION: Synthetic Construct, cloning site of
      pPicZalphaB complimentary strand

<400> SEQUENCE: 37
cggccggctg ggccacgtga attcctgcag cttcagcctc tcttttctcg agaga       55

<210> SEQ ID NO 38
<211> LENGTH: 55
<212> TYPE: DNA
<213> ORGANISM: Artificial Sequence
<220> FEATURE:
<223> OTHER INFORMATION: Synthetic Construct, cloning site of pPicZFVH

<400> SEQUENCE: 38
tctctcgaga aaagagccat ggaagctgca ggaattcacg tggcccagcc ggccg       55

<210> SEQ ID NO 39
<211> LENGTH: 55
<212> TYPE: DNA
<213> ORGANISM: Artificial Sequence
<220> FEATURE:
<223> OTHER INFORMATION: Synthetic Construct, cloning site of pPicZFVH
      complimentary strand

<400> SEQUENCE: 39
cggccggctg ggccacgtga attcctgcag cttccatggc tcttttctcg agaga       55

<210> SEQ ID NO 40
<211> LENGTH: 92
<212> TYPE: DNA
<213> ORGANISM: Artificial Sequence
<220> FEATURE:
<223> OTHER INFORMATION: Synthetic Construct, synthetic hinge fragment

```
<400> SEQUENCE: 40
gcggccgcgc caaagccaag taccccacca ggttcttcat gtccaccatg tccaggctct    60
ggcggtgcgc caatcgatag cggctttcta ga                                  92

<210> SEQ ID NO 41
<211> LENGTH: 92
<212> TYPE: DNA
<213> ORGANISM: Artificial Sequence
<220> FEATURE:
<223> OTHER INFORMATION: Synthetic Construct, synthetic hinge fragment
      complimentary strand

<400> SEQUENCE: 41
tctagaaagc cgctatcgat tggcgcaccg ccagagcctg acatggtgg acatgaagaa     60 cctggtgggg tacttggctt tggcgcggcc gc                                  92

<210> SEQ ID NO 42
<211> LENGTH: 18
<212> TYPE: PRT
<213> ORGANISM: Artificial
<220> FEATURE:
<223> OTHER INFORMATION: Amino acid sequence corresponding to cloning
      site of pPicZalphaB

<400> SEQUENCE: 42

Ser Leu Glu Lys Arg Glu Ala Glu Ala Ala Gly Ile His Val Ala Gln
1               5                   10                  15
Pro Ala

<210> SEQ ID NO 43
<211> LENGTH: 18
<212> TYPE: PRT
<213> ORGANISM: Artificial
<220> FEATURE:
<223> OTHER INFORMATION: Amino acid sequence corresponding to cloning
      site of pPicZFVH

<400> SEQUENCE: 43

Ser Leu Glu Lys Arg Ala Met Glu Ala Ala Gly Ile His Val Ala Gln
1               5                   10                  15
Pro Ala

<210> SEQ ID NO 44
<211> LENGTH: 30
<212> TYPE: PRT
<213> ORGANISM: Artificial
<220> FEATURE:
<223> OTHER INFORMATION: Amino acid sequence corresponding to synthetic
      hinge fragment

<400> SEQUENCE: 44

Ala Ala Ala Pro Lys Pro Ser Thr Pro Pro Gly Ser Ser Cys Pro Pro
1               5                   10                  15
Cys Pro Gly Ser Gly Gly Ala Pro Ile Asp Ser Gly Phe Leu
                20                  25                  30
```